(12) United States Patent
Watanabe et al.

(10) Patent No.: US 9,764,046 B2
(45) Date of Patent: Sep. 19, 2017

(54) LABELING COMPOSITION FOR INTRAOCULAR TISSUE, LABELING METHOD OF INTRAOCULAR TISSUE, AND SCREENING METHOD

(71) Applicant: CANON KABUSHIKI KAISHA, Tokyo (JP)

(72) Inventors: Kohei Watanabe, Yokohama (JP); Taichi Shintou, Saitama (JP); Tsuyoshi Nomoto, Tokyo (JP); Takeshi Miyazaki, Yokohama (JP); Toshio Tanaka, Tsu (JP); Yuhei Nishimura, Tsu (JP); Yasuhito Shimada, Tsu (JP); Norihiro Nishimura, Tsu (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 77 days.

(21) Appl. No.: 14/601,480

(22) Filed: Jan. 21, 2015

(65) Prior Publication Data
US 2015/0139908 A1 May 21, 2015

Related U.S. Application Data

(62) Division of application No. 13/133,357, filed as application No. PCT/JP2009/071865 on Dec. 24, 2009, now abandoned.

(30) Foreign Application Priority Data

Dec. 25, 2008 (JP) .................................. 2008-330988

(51) Int. Cl.
| | | |
|---|---|---|
| A61K 49/00 | (2006.01) |
| C07D 221/18 | (2006.01) |
| C07D 235/02 | (2006.01) |
| C07D 277/08 | (2006.01) |
| C07D 277/62 | (2006.01) |
| C07D 263/54 | (2006.01) |
| C07D 209/70 | (2006.01) |
| C07D 209/96 | (2006.01) |
| C07D 215/00 | (2006.01) |
| C07D 221/14 | (2006.01) |
| C07D 277/34 | (2006.01) |
| C07D 277/36 | (2006.01) |
| C07D 277/64 | (2006.01) |
| C07D 311/82 | (2006.01) |
| C07D 311/86 | (2006.01) |
| C07D 405/04 | (2006.01) |
| C07D 405/06 | (2006.01) |

(Continued)

(52) U.S. Cl.
CPC ...... *A61K 49/0021* (2013.01); *A61K 49/0002* (2013.01); *A61K 49/006* (2013.01); *A61K 49/0039* (2013.01); *A61K 49/0041* (2013.01); *C07D 209/70* (2013.01); *C07D 209/96* (2013.01); *C07D 215/00* (2013.01); *C07D 221/14* (2013.01); *C07D 221/18* (2013.01); *C07D 263/54* (2013.01); *C07D 277/34* (2013.01); *C07D 277/36* (2013.01); *C07D 277/64* (2013.01); *C07D 311/82* (2013.01); *C07D 311/86* (2013.01); *C07D 405/04* (2013.01); *C07D 405/06* (2013.01); *C07D 413/04* (2013.01); *C07D 413/06* (2013.01); *C07D 417/04* (2013.01); *C07D 417/06* (2013.01); *C07D 417/14* (2013.01); *C07D 491/052* (2013.01); *C07D 491/12* (2013.01); *C07D 497/10* (2013.01); *G01N 33/5088* (2013.01); *G01N 33/582* (2013.01); *G01N 2333/4603* (2013.01)

(58) Field of Classification Search
None
See application file for complete search history.

(56) References Cited

U.S. PATENT DOCUMENTS

| 4,366,314 A | 12/1982 | Beecken |
| 6,696,430 B1 | 2/2004 | Melles |

(Continued)

FOREIGN PATENT DOCUMENTS

| JP | 63-028932 B | 6/1988 |
| JP | 2-084390 A | 3/1990 |

(Continued)

OTHER PUBLICATIONS

Anliker, R., P. Moser, and D. Poppinger. "Bioaccumulation of dyestuffs and organic pigments in fish. Relationships to hydrophobicity and steric factors." Chemosphere 17.8 (1988): 1631-1644.*

(Continued)

*Primary Examiner* — Nissa Westerberg
(74) *Attorney, Agent, or Firm* — Fitzpatrick, Cella, Harper & Scinto

(57) ABSTRACT

The invention provides a labeling composition for an intraocular tissue of a living individual, which specifically labels the intraocular tissue without need of an invasive operation such as exposure of an ocular tissue or injection of a staining agent into the ocular tissue or a nerve tissue linking to the ocular tissue, a method of noninvasively labeling an intraocular tissue of a living individual, and a screening method using the labeling composition for the intraocular tissues. The composition contains a compound capable of labeling at least a photoreceptor cell layer of a retina, wherein the compound is a staining compound having a particular structure as a partial structure thereof.

2 Claims, 4 Drawing Sheets

(51) Int. Cl.

| | | |
|---|---|---|
| C07D 413/04 | (2006.01) | |
| C07D 413/06 | (2006.01) | |
| C07D 417/04 | (2006.01) | |
| C07D 417/06 | (2006.01) | |
| C07D 417/14 | (2006.01) | |
| C07D 491/052 | (2006.01) | |
| C07D 491/12 | (2006.01) | |
| C07D 497/10 | (2006.01) | |
| G01N 33/50 | (2006.01) | |
| G01N 33/58 | (2006.01) | |

(56) References Cited

U.S. PATENT DOCUMENTS

| | | |
|---|---|---|
| 6,720,314 B1 | 4/2004 | Melles |
| 2003/0144247 A1 | 7/2003 | Kuwano et al. |
| 2004/0197268 A1 | 10/2004 | Augelli-Szafran et al. |
| 2004/0256002 A1 | 12/2004 | Horiuchi et al. |
| 2008/0007693 A1 | 1/2008 | Williams et al. |
| 2008/0090914 A1 | 4/2008 | Enaida et al. |
| 2008/0206149 A1 | 8/2008 | Haritoglou et al. |
| 2011/0182810 A1 | 7/2011 | Nomoto et al. |
| 2011/0189096 A1 | 8/2011 | Watanabe et al. |
| 2011/0243850 A1 | 10/2011 | Shintou et al. |
| 2015/0182518 A1 | 7/2015 | Shintou et al. |
| 2015/0274715 A1 | 10/2015 | Shintou et al. |

FOREIGN PATENT DOCUMENTS

| | | |
|---|---|---|
| JP | 3-144416 A | 6/1991 |
| JP | 11-265004 A | 9/1999 |
| JP | 2001-315437 A | 11/2001 |
| JP | 2002-514470 A | 5/2002 |
| JP | 2002-514471 A | 5/2002 |
| JP | 2005-508432 A | 3/2005 |
| JP | 2007-262078 A | 10/2007 |
| JP | 2008-094897 A | 4/2008 |
| JP | 2008-522953 A | 7/2008 |
| JP | 2008-297526 A | 12/2008 |
| JP | 2008-543395 A | 12/2008 |
| WO | 99/58159 A1 | 11/1999 |
| WO | 99/58160 A1 | 11/1999 |
| WO | 03/040242 A2 | 5/2003 |
| WO | 2006/133903 A2 | 12/2006 |

OTHER PUBLICATIONS

Kubota et al. Ecotoxicology and environmental safety (1979) vol. 3, p. 256-268.*

Communication under Article 94(3) EPC in European Application No. 09835113.3 (Jun. 27, 2016).

Extended European Search Report in European Application No. 09835113.3 (Aug. 3, 2015).

Alexander K. Ball et al., "Identification of Sulfur Groups in the Outer Plexiform Layer of the Newt Retina," 37 Exp. Eye Res. 199-208 (1983).

Dino J. Ravnic et al., "Vessel Painting of the Microcirulation Using Fluorescent Lipophilic Tracers," 70 Microvascular Research 90-96 (Aug. 2005).

Felipe Santos et al., "Lateral Line Hair Cell Maturation is a Determinant of Aminoglycoside Susceptibility in Zebrafish (*Danio rerio*)," 213 Hearing Research 25-33 (Feb. 2006).

K. Negishi et al., "Opposite Effects of Ammonia and Carbon Dioxide on Dye Coupling Between Horizontal Cells in the Carp Retina," 342 Brain Research 330-339 (1985).

Mark E. Fuller et al., "Development of a Vital Fluorescent Staining Method for Monitoring Bacterial Transport in Subsurface Environments," vol. 66, No. 10 Applied and Environmental Microbiolgy 4486-4496 (Oct. 2000).

Robert Guss et al., "Rhodamine B as a Test Molecule in Intraocular Dynamics," 25 Invest Ophthalmol Vis Sci 758-762 (1984).

Toshihiko Matsuo, "A Simple Method for Screening Photoelectric Dyes Towards Their Use for Retinal Prostheses," vol. 57, No. 5 Acta Med. Okayama 257-260 (2003).

Donald R. Korb, O. D., et al., "An Evaluation of the Efficacy of Fluorescein, Rose Bengal, Lissamine Green, and a New Dye Mixture for Ocular Surface Staining," 34(1) Eye & Contact Lens 61-64 (2008).

Paul N. Baird et al., "Analysis of the Y402H Variant of the Complement Factor H Gene in Age-Related Macular Degeneration," vol. 47, No. 10 Investigative Ophthalmology & Visual Science 4491-4198 (Oct. 2006).

Tamotsu Horiuchi et al., "Highly-efficient Metal-free Organic Dyes for Dye-sensitized Solar Cells," Chem. Commun. 3036-3037 (Nov. 3, 2003).

James M. Fadool et al., "Zebrafish: A Model System for the Study of Eye Genetics," 27 Progress in Retinal and Eye Res. 89-110 (2008).

Paul Goldsmith, "Zebrafish as a Pharmacological Tool: The How, Why and When," 4 Current Opinion in Pharmacology 504-512 (Jul. 2004).

Katsuhiko Fukui et al., "Simultaneous Fluorescein Angiography and Indocyanine Angiography with Heidelberg Retina Angiograph (HRA)," 23 Ophthalmologic Photograph 3-10 (2007).

Non-final Office Action in U.S. Appl. No. 13/084,997 (Oct. 12, 2012).

Ariane Jansma et al., "Automated Microflow NMR: Routine Analysis of Five-Microliter Samples," 77(19) Anal. Chem. 6509-6515 (Oct. 2005).

International Search Report in (with Written Opinion) International Application No. PCT/JP2009/071865 (Mar. 2010).

International Preliminary Report on Patentability (with Written Opinion) in International Application No. PCT/JP2009/071865 (Jul. 2011).

Daniel C. Gray et al., "In Vivo Imaging of the Fine Structure of Rhodamine-Labeled Macaque Retinal Ganglion Cells," 49(1) IOVS 467-473 (Jan. 2008) (XP055179577).

Paolo Bianchini et al., "Live Imaging of Mammalian Retina: Rod Outer Segments are Stained by Conventional Mitochondrial Dyes," 13(5) J. Biomed. Opt. 054017 (1-6) (Oct. 2008) (XP055179759).

Josh Morgan et al., "Imaging Techniques in Retinal Research," 80(3) Experimental Eye Research 297-306 (Mar. 2005) (XP004753513).

Claudia A.O. Stuermer, "Retinotopic Organization of the Developing Retinotectal Projection in the Zebrafish Embryo," 8 (12) J. Neurosci. 4513-4530 (Dec. 1988) (XP055179400).

S. S. Ramos et al., "1H and 13C NMR Spectra of Commercial Rhodamine Ester Derivatives," 38(6) Magn. Res. Chem. 475-478 (Jun. 2000) (XP002571785).

Supplemental Partial European Search Report in European Application No. 09835113.3 (dated Apr. 7, 2015).

U.S. Appl. No. 14/408,778, filed Dec. 17, 2014, Shintou et al.

* cited by examiner

LABELING COMPOSITION FOR INTRAOCULAR TISSUE, LABELING METHOD OF INTRAOCULAR TISSUE, AND SCREENING METHOD

CROSS-REFERENCE TO RELATED APPLICATIONS

This application is a divisional application of application Ser. No. 13/133,357, which was the National Stage of International Application No. PCT/JP2009/071865, filed Dec. 24, 2009, which claims the benefit of Japanese Patent Application No. 2008-330988, filed Dec. 25, 2008. All of these prior applications are incorporated herein by reference in their entirety.

TECHNICAL FIELD

The present invention relates a labeling composition for an intraocular tissue, which is used for noninvasively labeling an intraocular tissue of a living sample, a labeling method of the intraocular tissue, and a screening method.

BACKGROUND ART

In recent years, there has been a tendency to increase the number of patients suffering ophthalmic diseases with the progress of population aging. The progress of amblyopia by an ophthalmic disease leads to blindness in the worst case, and the patient is markedly impaired in the quality of life. Therefore, it is required to detect the disease in its early stage and take a measure to cure the disease or retard the progress thereof. Typical diseases forming a cause of halfway blindness include diabetic retinopathy, macular degeneration diseases and glaucoma, and the fundus retina is concerned with many of them. For diagnoses of these diseases, diagnoses by evaluation of visual function by inspection of visual field, and morphological evaluation of the fundus retina using a fundus camera, an optical coherence tomograph (OCT) and a scanning laser ophthalmoscope are conducted.

In a retinopathic disease, reduction of visual functions is caused by disorder of neurocytes. In recent years, it has become possible to visualize the condition of a layer structure of a reticular tissue by an OCT technique, and many new findings relating to a living body tissue of a retinal lesion have been obtained. However, a current OCT image is low in resolution, and so it has been unable to visualize the morphology of cells forming the retina.

As a visualization technique of an ocular tissue, a method of imaging and staining the ocular tissue using a staining compound has heretofore been known. For example, there is a method of visualizing a choroidal vessel and a retinal vessel using a fluorescent pigment such as indocyanine green or fluorescein (Ophthalmologic Photograph, 23, pp. 3-10(2007)). As a staining method of the cornea, a method of using rose Bengal or fluorescein is also known (EYE CONTACT LENS, 34, pages 61 to 64 (2008)).

On the other hand, as a visualization technique of intraocular tissues such as a vitreous body, retina and optic nerve, a method of administering a stain composition to a vitreous cavity mainly at surgical operation is disclosed. For example, there is a composition for staining a retinal membrane in a vitreous retina surgery (Japanese Patent No. 3469198). It is also disclosed that a transmission substance injected into the vitreous body remains in the retina (Japanese Patent Application Laid-Open No. 2007-262078). Besides, it is reported that in order to image retinal ganglion cells of a rat, a retrograde axonal transport tracer is injected into a superior colliculus of the midbrain linking to a retinal ganglion to observe it with a laser ophthalmoscope (Invest Ophthalmol Vis Sci, 47(10), p. 4198 (2006)). As described above, it has been necessary to directly administer the stain composition to the inside of an eye for visualizing the intraocular tissue.

Incidentally, a drug to act on the retina or retinal nerve tissue is administered by intravenous injection or orally. However, the quantity of the drug transferred to the retina is extremely small. On the other hand, drug administration to the vitreous cavity enables a large quantity of the drug transferred to the retinal tissue compared with the intravenous injection or oral administration. However, an advanced technique is required, and a burden on a patient is also great, and so it is extremely difficult to use it except for the case of surgery or curing, and such administration has been unable to be used for the morphological or functional evaluation of the fundus retina.

DISCLOSURE OF THE INVENTION

It is an object of the present invention to provide a labeling composition for an intraocular tissue, which can simply label an intraocular tissue of a living individual. In particular, the present invention provides a labeling composition, which can label the intraocular tissue in vivo. Another object of the present invention is to provide a method of noninvasively labeling an intraocular tissue of a living individual without need of an invasive operation such as exposure of an ocular tissue or needling into the ocular tissue or a nerve tissue linking to the ocular tissue. A further object of the present invention is to provide a screening method using the labeling composition for the intraocular tissue.

The present inventors have carried out an extensive investigation for achieving the above objects. As a result, a group of compounds, which provide new use of labeling an intraocular tissue of a living individual, has been found. In other words, the group of compounds, which can label the intraocular tissue of the living individual, has been found to succeed in providing a labeling composition for an intraocular tissue.

The present inventors have also established a method for noninvasively labeling the intraocular tissue. The present inventors have further developed an imaging method of the intraocular tissue using the labeling composition for the intraocular tissue according to the present invention, a screening method using the labeling composition for the intraocular tissue, which can label the intraocular tissue, and a diagnostic drug for the intraocular tissue, thus leading to completion of the present invention.

As shown in the following Comparative Examples, compounds for staining an intraocular tissue, which have been conventionally known, cannot stain an intraocular tissue of a living individual according to a conventional method.

The present invention is as follows.

The present invention provides a labeling composition for an intraocular tissue of a living individual, which comprises a compound capable of labeling at least a photoreceptor cell layer of a retina, wherein the compound is a staining compound having a structure represented by the following general formula (I) or general formula (II) as a partial structure thereof,

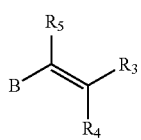
(II)

wherein in the general formula (I), $R_1$ and $R_2$ are, independently of each other, a hydrogen atom, an alkyl group or an aryl group, $R_1$ and $R_2$ may bond to each other to form a ring, and A is a structure represented by any one of the following general formulae (III) to (IX) and (VIII')

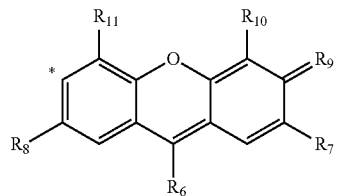
(III)

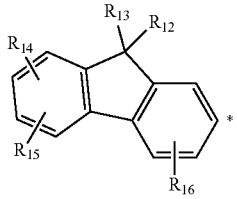
(IV)

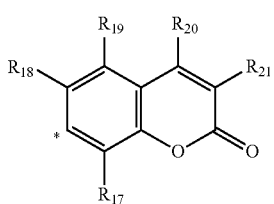
(V)

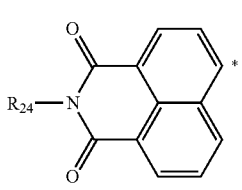
(VI)

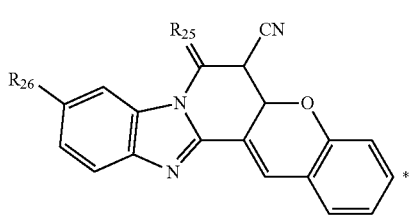
(VII)

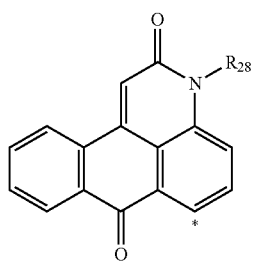
(VIII)

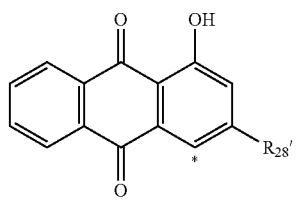
(VIII')

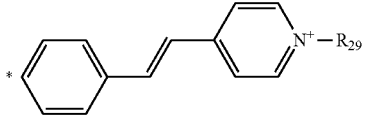
(IX)

wherein in the general formula (III), $R_6$ is an aryl group, $R_7$, $R_8$, $R_{10}$ and $R_{11}$ are, independently of one another, a hydrogen atom, an alkyl group, an aryl group or a halogen atom, and $R_9$ is an ammonium salt group having a counter anion, in the general formula (IV), $R_{12}$ and $R_{13}$ are, independently of each other, a hydrogen atom, an alkyl group, an aryl group or a heterocyclic group, and $R_{14}$ to $R_{16}$ are, independently of one another, a hydrogen atom, an alkyl group, an aryl group, a heterocyclic group, a halogen atom or an amino group, in the general formula (V), $R_{17}$ and $R_{18}$ are, independently of each other, a hydrogen atom, an alkyl group or an alkoxy group, $R_{19}$ and $R_{20}$ are, independently of each other, a hydrogen atom, an alkyl group, an alkoxy group, a hydroxyl group or a cyano group, $R_{21}$ is a heterocyclic group or —CH=C($R_{22}$)($R_{23}$), $R_{22}$ and $R_{23}$ are, independently of each other, a hydrogen atom, a cyano group, a heterocyclic group, a carboxyl group or a carboxylate group, and $R_1$ and $R_{17}$, $R_2$ and $R_{18}$, and $R_{22}$ and $R_{23}$ may, independently of one another, bond to each other to form a ring, in the general formula (VI), $R_{24}$ is a hydrogen atom, an alkyl group, an aryl group or a heterocyclic group, in the general formula (VII), $R_{25}$ is an oxygen atom, a sulfur atom or N($R_{27}$), $R_{26}$ is a hydrogen atom, an alkyl group, an alkoxy group or a sulfonic group, and $R_{27}$ is a hydrogen atom, an alkyl group or an aryl group, in the general formula (VIII), $R_{28}$ is a hydrogen atom, an alkyl group or an aryl group, in the general formula (VIII'), $R_{28}'$ is a halogen atom, an alkoxy group or an aryloxy group, and in the general formula (IX), $R_{29}$ is a hydrogen atom, an alkyl group or an aryl group; and wherein A is also a structure represented by the following general formula (X)

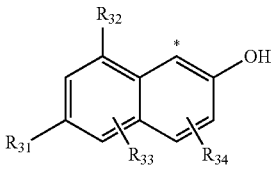
(X)

wherein in the general formula (X), $R_{31}$ and $R_{32}$ are individually a sulfonic group or a salt thereof, and $R_{33}$ and $R_{34}$ are individually a hydrogen atom, an alkyl group, an alkoxy group or a halogen atom, with the proviso that $R_1$ and $R_2$ in the general formula (I) bond to each other to form one substituent group =N—$R_{30}$, and $R_{30}$ is an aryl group or a heterocyclic group,
further wherein in the general formula (II), $R_3$ and $R_4$ are, independently of each other, a hydrogen atom, an alkenyl group, a cyano group, a carboxyl group, a carboxylate group, a sulfonic group, an acyl group or a heterocyclic group, R₃ and R₄ may bond to each other to form a ring, and R₅ is a hydrogen atom, an alkyl group, an aryl group or a heterocyclic group, with the proviso that one of R₃ and R₄ is a hydrogen atom, and the other is a heterocyclic group represented by the following general formula (XI)

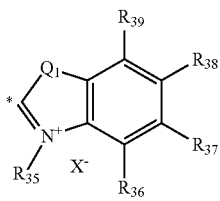
(XI)

wherein in the general formula (XI), R₃₅ is an alkyl group or an aryl group, R₃₆ to R₃₉ are, independently of one another, a hydrogen atom, an alkyl group, an aryl group, an alkoxy group, a carboxyl group, a sulfonic group, a heterocyclic group, an amino group or a halogen atom, R₃₆ and R₃₇, R₃₇ and R₃₈, or R₃₈ and R₃₉ may bond to each other to form a ring, X⁻ is an anionic group, and Q₁ is a sulfur atom, oxygen atom, —C(R₄₀)(R₄₁)—, —CH=CH— or —N(R₄₂)—, in which R₄₀ to R₄₂ are individually a hydrogen atom, an alkyl group or an aryl group, and R₄₀ and R₄₁ may bond to each other to form a ring, and wherein the ring formed by bonding R₃ and R₄ in the general formula (II) to each other is represented by any one of the following general formulae (XII), (XIII) and (XV)

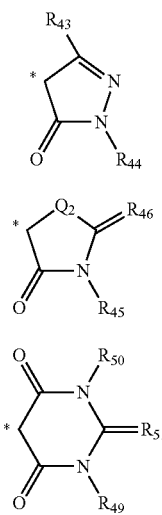

wherein in the general formula (XII), R₄₃ is a hydrogen atom, an alkyl group, an aryl group or a heterocyclic group, and R₄₄ is an alkyl group, an aryl group, a carboxyl group, a carboxylate group, a hydroxyl group or an amino group, in the general formula (XIII), Q₂ is an oxygen atom, a sulfur atom or —N(R₅₂)—, R₄₅ is a hydrogen atom, an alkyl group, an aryl group or a heterocyclic group, R₄₆ is a sulfur atom, an oxygen atom, =NR₅₃, a heterocyclic group or a dicyanomethylene group, and R₅₂ and R₅₃ are individually a hydrogen atom, an alkyl group, an aryl group or a heterocyclic group, and in the general formula (XV), R₄₉ and R₅₀ are, independently of each other, a hydrogen atom, an alkyl group or an aryl group, and R₅₁ is an oxygen atom or a sulfur atom, and B is a structure represented by any one of the following general formulae (XVI) to (XVIV) and (XVII')

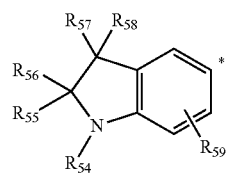
(XVI)

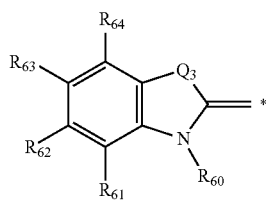
(XVII)

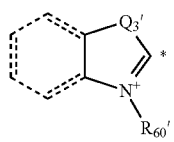
(XVII')

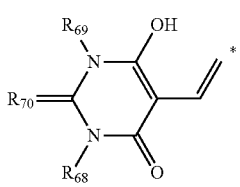
(XVIII)

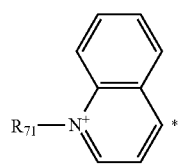
(XVIV)

wherein in the general formula (XVI), R₅₄ is a hydrogen atom, an alkyl group, an aralkyl group, an alkenyl group, an aryl group, a heterocyclic group or an acyl group, R₅₅ to R₅₈ are, independently of one another, a hydrogen atom, an alkyl group, an aryl group, a carboxyl group, a carboxylate group or an acyl group, R₅₅ and R₅₇ may bond to each other to form a ring, and R₅₉ is a hydrogen atom, an alkyl group, an alkoxy group or a halogen atom, in the general formula (XVII), R₆₀ is a hydrogen atom, an alkyl group or an aryl group, R₆₁ to R₆₄ are, independently of one another, a hydrogen atom, an alkyl group, an aryl group, an alkoxy group, a carboxyl group, a sulfonic group, a heterocyclic group, an amino group or a halogen atom, R₆₁ and R₆₂, R₆₂ and R₆₃, or R₆₃ and R₆₄ may bond to each other to form a ring, and Q₃ is a sulfur atom, an oxygen atom, —C(R₆₅)(R₆₆)— or —CH=CH—, in which R₆₅ and R₆₆ bond to each other to form a ring, in the general formula (XVII'), R₆₀' is a hydrogen atom, an alkyl group or an aryl group, Q₃' is a sulfur atom or an oxygen atom, and dotted lines in the general formula (XVII') represent the case where a benzene ring is present or absent, in the general formula (XVIII), R₆₈ and R₆₉ are, independently of each other, a hydrogen atom, an alkyl group or an aryl group, and $R_{70}$ is an oxygen atom or a sulfur atom, and in the general formula (XVIV), $R_{71}$ is an alkyl group, further wherein B and $R_5$ may bond to each other to form a benzothiophen-3-one ring, and at that time, $R_3$ and $R_4$ bond to each other to form a benzothiophen-3-one ring.

The present invention also provides a labeling composition for labeling an intraocular tissue of a living individual, which comprises a compound capable of labeling at least a photoreceptor cell layer of the retina.

The present invention further provides a staining agent for an intraocular tissue, which comprises the above-described labeling composition for the intraocular tissue.

The present invention still further provides a diagnostic composition comprising, as an active agent, the above-described labeling composition or staining agent for the intraocular tissue.

The present invention yet still further provides a staining method of an ocular tissue, which comprises a step of bringing the above-described labeling composition or staining agent for the intraocular tissue into contact with the ocular tissue.

The present invention yet still further provides a multiple staining method of an ocular tissue, which comprises using plural kinds of labeling compositions including at least one of the above-described labeling composition and staining agent for the intraocular tissue.

The present invention yet still further provides an imaging method of an intraocular tissue, which comprises a step of irradiating the intraocular tissue with excitation light to observe fluorescence, and comprises staining by the above-described staining method.

The present invention yet still further provides an evaluating method of the condition of the retina, which comprises using the above-described imaging method of the intraocular tissue.

The present invention yet still further provides a screening method comprising using a model animal labeled with the above-described labeling composition for the intraocular tissue.

The present invention yet still further provides a screening method of a disease curing medicine or disease preventing medicine, which comprises a step of administering a test substance to a model animal, a step of administering the above-described labeling composition for the intraocular tissue to the model animal, and a step of checking the condition of the labeling of the intraocular tissue of the model animal with the labeling composition for the intraocular tissue.

EFFECTS OF THE INVENTION

The present invention provides a labeling composition for an intraocular tissue, whereby noninvasive labeling of the intraocular tissue, which has heretofore been impossible to conduct, becomes feasible, and so it is possible to image the condition of a layer structure of the intraocular tissue and the cell morphology thereof in a simple and easy way and with high definition. It is thereby possible to conduct evaluation and analysis of the intraocular tissue with high precision. In addition, the labeling composition for the intraocular tissue according to the present invention is combined with an observing and analyzing apparatus for intraocular tissues, whereby the condition of an intraocular tissue, or the retina in particular, of a living individual, which has heretofore been difficult to be observed, can be grasped with accuracy and high sensitivity, and so a new tool effective for researches and diagnoses in an ophthalmic field can be provided.

BEST MODE FOR CARRYING OUT THE INVENTION

Figure 1:
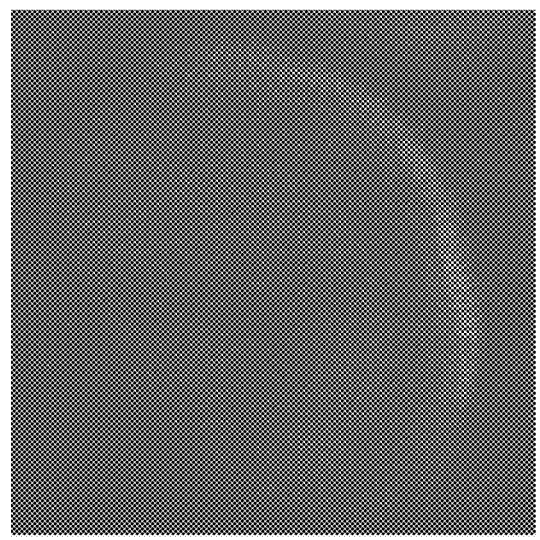
FIG. 1 illustrates labeling of a retinal tissue observed in Example 4.
Figure 2:
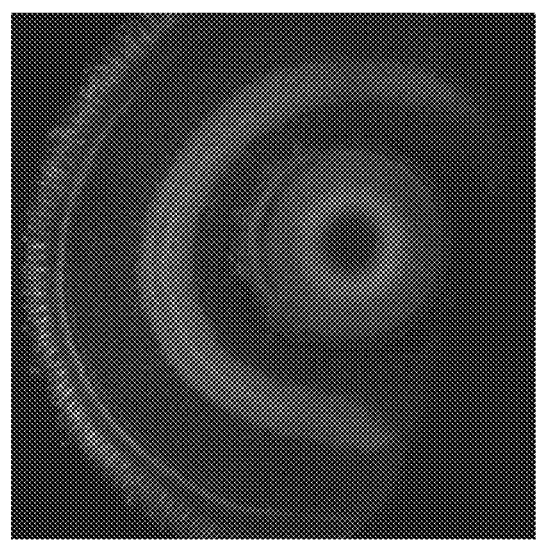
FIG. 2 illustrates labeling of a retinal tissue observed in Example 2.
Figure 3:
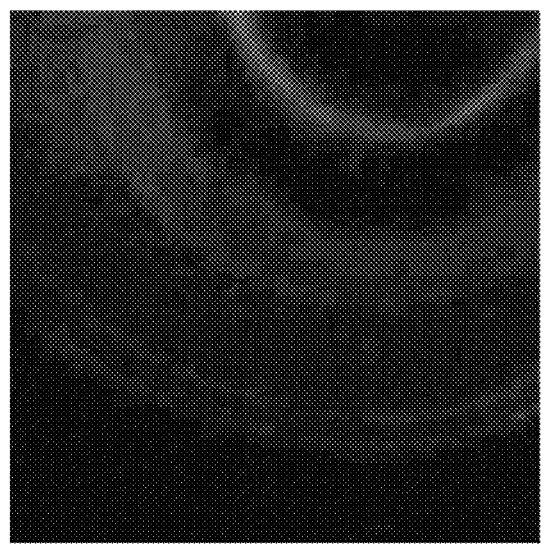
FIG. 3 illustrates a fluorescent observation image of a retinal tissue observed in Comparative Example 1.

The present invention will hereinafter be described in detail.
<Labeling of Intraocular Tissue>
Definition of Labeling In the present invention, the labeling of an intraocular tissue means that a pigment composition, which is an active agent in the above-described composition, is held in an intraocular tissue, or on the surface thereof, or at the periphery thereof, thereby becoming a state capable of detecting at least one of the form, position and function of the intraocular tissue. Detections include a method of acquiring a fluorescent image or labeled image by an image acquiring unit, which will be described subsequently, and a visually observing method.

A typical example of the labeling is staining, and the labeling composition for the intraocular tissue, by which the so-called cell staining or tissue staining becomes feasible, is provided by the present invention.
Labeling Mechanism A detailed mechanism by which the labeling composition for the intraocular tissue according to the present invention labels a specific intraocular tissue is not known. However, it is inferred that the group of compounds provided by the present invention is easy to permeate a cell membrane and migrate because they are stable compounds with a low molecular weight and have a structure easy to be held in a specific cell, thereby being held in the specific tissue of the cell.

In addition, the labeling composition for the intraocular tissue according to the present invention favorably labels the intraocular tissue immediately after administration to a living body. However, it may take a certain period of time to label the intraocular tissue according to a method of administration. From this point of view, the composition favorably contains a staining compound capable of labeling within several minutes or several hours after the administration.

In the case where one wished to observe a change with time, it is favorable to select a staining compound remaining for a long period of time after being labeled. However, it is favorable to select a staining compound easy to be discharged by metabolism after the administration for reducing an influence on the living body.

<Living Sample>

No particular limitation is imposed on a living individual, the intraocular tissue of which can be labeled with the labeling composition for the intraocular tissue according to the present invention. However, examples of vertebrate animals include bony fishes such as *T. rubripes, T. niphobles, T. nigrovirides*, Japanese killifish and Zebrafish; Amphibia such as *X. laevis*; birds such as domestic fowl and quail; small animals such as rat, mouse and hamster; large animals such as goat, pig, dog, cat, cattle and horse; monkey; chimpanzee; and human. In particular, the intraocular tissues of these living individuals can be labeled in a living state. The human may be excluded from the living samples.

In Zebrafish, main organs are formed in 6 and 7 days after fertilization, and the histological form of an eyeball is also almost completed. Therefore, the use of a 7-day-old embryo makes it possible to conduct a test almost without having an influence of individual differences. In Zebrafish, at least about 200 fertilized ova are obtained in one spawning, and so there is a merit of obtaining Zebrafishes having the same genetic background to be a good convenience to screening.

<Intraocular Tissue>

No particular limitation is imposed on an intraocular tissue, which can be labeled with the labeling composition for the intraocular tissue according to the present invention, so far as it is an intraocular tissue forming an intraocular structure being in no direct contact with the outside in an eyeball and is a tissue present in the eye, excluding tissues on the surface of the eyeball. Examples thereof include a retinal tissue comprising retinal pigment epithelium layer, photoreceptor cell layer, outer limiting membrane, outer granular layer, outer reticular layer, internal granular layer, internal reticular layer, ganglion cell layer and internal limiting membrane, iris, ciliary body, choroid, lens, vitreous body, lacrimal gland, optic nerve, optic disk, optic tract, retinal blood vessel, diseased-condition tissues of these tissues, and neogenetic tissues and cancer tissues caused by diseases. When intraocular tissues different from the above-described tissues are present according to the kind of a living body or development stage or due to developmental anomaly or a disease, their tissues may also be included.

The labeling composition for the intraocular tissue according to the present invention is favorably used in staining of a retinal tissue in particular. In the staining of the retinal tissue, one or more tissues including the photoreceptor cell layer among the above-described plural layers forming the retinal tissue or cells thereof may be stained, so that availability becomes high in uses such as visualization of a retinal disease.

No particular limitation is imposed on the cells included in the above-described retinal tissue. However, examples thereof include amacrine cells, horizontal cells, bipolar cells, interplexiform cells, cone cells, rod cells, fibroblasts, Muller glia cells, and tumor cells and undifferentiated cells (stem cells) thereof. The labeling composition for the intraocular tissue according to the present invention can favorably stain one or more cells of the rod cells and plural kinds of cone cells different in the sensitivity to a wavelength region.

In the present invention, to stain the cell morphology of the retina means that at least one of cells making up the retinal cells is stained to become a state that the cell morphology can be clearly determined one by one.

<Administering Method>

In the present invention, to label the intraocular tissue without damaging the ocular tissue or the nerve tissue linking to the ocular tissue means labeling the intraocular tissue with the labeling composition for the intraocular tissue without applying a surgical damage such as incision of the ocular tissue or needling into the ocular tissue or the nerve tissue linking to the ocular tissue to the ocular tissue.

No particular limitation is imposed on the labeling method without the surgical damage. However, examples thereof include a method of exposing a part or the whole of a living individual to the labeling composition for the intraocular tissue, a method by oral contact, a method by pneumonic contact, a method by nasal contact, a method by transgastrointestinal contact, a method by transmucosal contact, a method by transhumoral contact, a method by hypoglossal contact, a method by intravascular contact such as intravenous or intra-arterial contact, a method by intra-abdominal contact, an intra-abdominal, subcutaneous, intracutaneous, intravesical or endotracheal (intrabronchial) injection method, and a method by contact with the interior of a living body by a device such as spraying or coating.

In the present invention, the nerve tissue linking to the ocular tissue means a nerve tissue histologically linking to the ocular tissue. Specifically, examples thereof include an optic nerve tissue and a cranial nerve tissue though not particularly limited thereto.

In the case of administration to an animal, the administering form, administering route and dose thereof are suitably selected according to the body weight and condition of the subject animal.

<Compound>

The compound contained in the labeling composition for the intraocular tissue according to the present invention includes a compound capable of labeling at least a photoreceptor cell layer of the retina. Favorably, the compound includes a compound selectively labeling one or more cells selected from rod cells present in the photoreceptor cell layer of the retina and plural kinds of cone cells or a part of the cell bodies of these cells. "Selective labeling" in the present invention means a state that at least a specific cell or a part thereof is labeled, and unlabeled cells or a part thereof exist in the retinal tissue.

The compound contained in the labeling composition for the intraocular tissue according to the present invention is favorably a low-molecular weight compound because the compound is caused to migrate to the intraocular tissue as an object of labeling, in particular, the retinal tissue, and so a compound having a molecular weight of 2,000 or less is selected. The compound is favorably a compound having a molecular weight of favorably 1,500 or less, particularly 1,000 or less.

The compound of the present invention is favorably a fluorescent compound having fluorescence. Since the fluorescent compound is high in sensitivity, labeling becomes feasible at a low concentration, and so a necessary amount of the compound can be relatively reduced. Compounds different in labeling sites and fluorescent spectrum are combined and selected, whereby multiple labeling of plural tissues becomes feasible, so that information on a plurality of tissues can be obtained in one observation, and so availability becomes high.

The compound used in the labeling composition for the intraocular tissue according to the present invention is favorably a staining compound having a structure represented by the following general formula (I) or general formula (II) as a partial structure thereof.

(I)

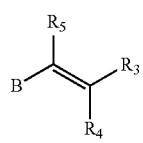
(II)

In the general formula (I), $R_1$ and $R_2$ are, independently of each other, a hydrogen atom, an alkyl group or an aryl group, and $R_1$ and $R_2$ may bond to each other to form a ring.

No particular limitation is imposed on the alkyl group in $R_1$ and $R_2$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

No particular limitation is imposed on the aryl group in $R_1$ and $R_2$. However, examples thereof include 6- to 14-membered monocyclic or polycyclic aryl groups such as phenyl, naphthyl, phenanthryl and anthracenyl groups.

$R_1$ and $R_2$ may additionally have substituent(s), and no particular limitation is imposed on the substituent(s) so far as the storage stability of the staining compound is not markedly impaired. Examples thereof include alkyl groups such as methyl, ethyl, n-propyl, isopropyl, n-butyl, isobutyl, sec-butyl and tert-butyl groups; aryl groups such as phenyl and naphthyl groups; alkoxy groups such as methoxy, ethoxy and butoxy groups; aryloxy groups such as phenoxy and naphtyloxy groups; alkylsulfanyl groups such as thiomethyl, thioethyl, thiopropyl, thiobutyl and thiophenyl groups; mono-substituted amino groups such as methylamino and butylamino groups; di-substituted amino groups such as dimethylamino, N-ethyl-N-phenylamino and diphenylamino groups; acyl groups such as acetyl, benzoyl, carboxyl, carboxylate and carbamoyl groups; sulfonyl groups such as sulfonic, sulfonate and sulfamoyl groups; heterocyclic groups such as pyridyl, triazinyl and benzothiazolyl groups; a nitro group; halogen atoms such as fluorine, chlorine, bromine and iodine atoms; a polyethylene glycol groups; and salts such as quaternary ammonium salts, carboxylates and sulfonates. The groups favorably have a substituent having such a nature that the water solubility is improved, among these substituents. Particularly favorable examples of such a substituent include carboxyl, sulfonic, polyethylene glycol, carboxylate and sulfonate groups though not limited thereto. Description of these substituents exemplified above is hereinafter omitted as described as "favorable examples of additional substituents" in the present specification.

No particular limitation is imposed on the ring formed by bonding $R_1$ and $R_2$ to each other. However, examples thereof include heterocycles such as pyridine, piperazine, morpholine, thiomorpholine and pyridinium rings.

Description of A in General Formula (I)

A is a structure represented by any one of the following general formulae (III) to (IX) and (VIII').

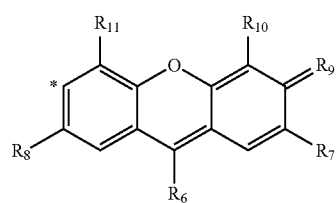
(III)

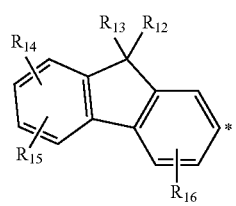
(IV)

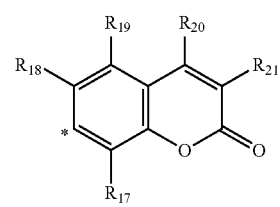
(V)

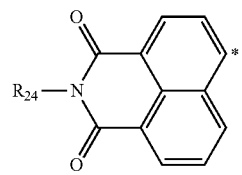
(VI)

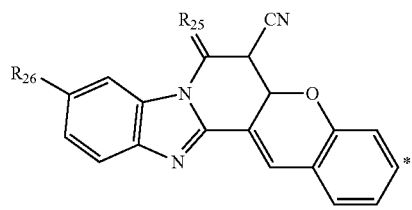
(VII)

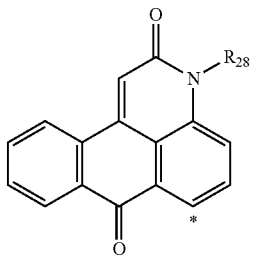
(VIII)

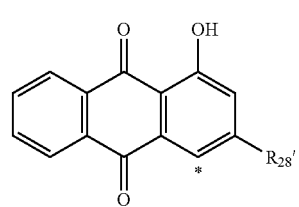
(VIII')

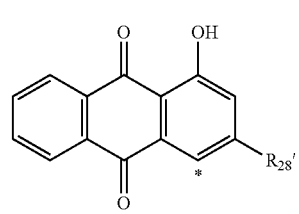
(VIII')

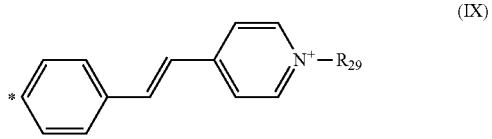

(IX)

Each structure will hereinafter be described in detail.
Description of General Formula (III)

In the general formula (III), $R_6$ is an aryl group. $R_7$, $R_8$, $R_{10}$ and $R_{11}$ are, independently of one another, a hydrogen atom, an alkyl group, an aryl group or a halogen atom. $R_9$ is an ammonium salt group having a counter anion.

No particular limitation is imposed on the aryl group in $R_6$. However, examples thereof include 6- to 14-membered monocyclic or polycyclic aryl groups such as phenyl, naphthyl, phenanthryl and anthracenyl groups. The ring may additionally have substituent(s), and no particular limitation is imposed on the substituent(s) so far as the storage stability of the staining compound is not markedly impaired. Examples thereof include substituents described as "favorable examples of additional substituents" above.

The group favorably has a substituent having such a nature that the water solubility is improved, among these substituents. Particularly favorable examples of such a substituent include carboxyl, sulfonic, polyethylene glycol, carboxylate and sulfonate groups though not limited thereto.

$R_6$ is favorably a phenyl or naphthyl group. In particular, a phenyl group having a water-soluble substituent such as a carboxyl, sulfonic, polyethylene glycol, carboxylate or sulfonate group is favorable from the viewpoint of improving the water solubility of the compound.

No particular limitation is imposed on the alkyl group in $R_7$, $R_8$, $R_{10}$ and $R_{11}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

No particular limitation is imposed on the aryl group in $R_7$, $R_8$, $R_{10}$ and $R_{11}$. However, examples thereof include 6- to 14-membered monocyclic or polycyclic aryl groups such as phenyl, naphthyl, phenanthryl and anthracenyl groups.

Examples of the halogen atom in $R_7$, $R_8$, $R_{10}$ and $R_{11}$ include fluorine, chlorine, bromine and iodine atoms.

$R_7$, $R_8$, $R_{10}$ and $R_{11}$ are each favorably a hydrogen atom, an alkyl group or a halogen atom, and the hydrogen atom is particularly favorable from the viewpoint of stability of the compound.

No particular limitation is imposed on the ammonium salt group having a counter anion in $R_9$. However, examples thereof include amino groups obtained by converting an amino group to a quaternary salt. No particular limitation is imposed on the counter anion. However, examples thereof include halide ions such as fluoride, chloride, bromide and iodide ions; inorganic acid ions such as sulfate, phosphate, nitrate, tetrafluoroborate and hexafluorophosphate ions; Lewis-acid-containing ions such as tetrachloroaluminate ion; and organic acid ions such as acetate, lactate, methanesulfonate, benzenesulfonate, p-toluenesulfonate, trifluoroacetate, trifluoromethanesulfonate and tetraphenylborate ions.

When $R_6$ in the molecular structure represented by the general formula (III) is an aromatic ring having a sulfonic or carboxyl group at an ortho position, a tautomer of the following general formula (III') or (III'') exists. The structure represented by the general formula (III) that the staining compound according to the present invention has also includes a structure represented by the following general formula (III') or (III'').

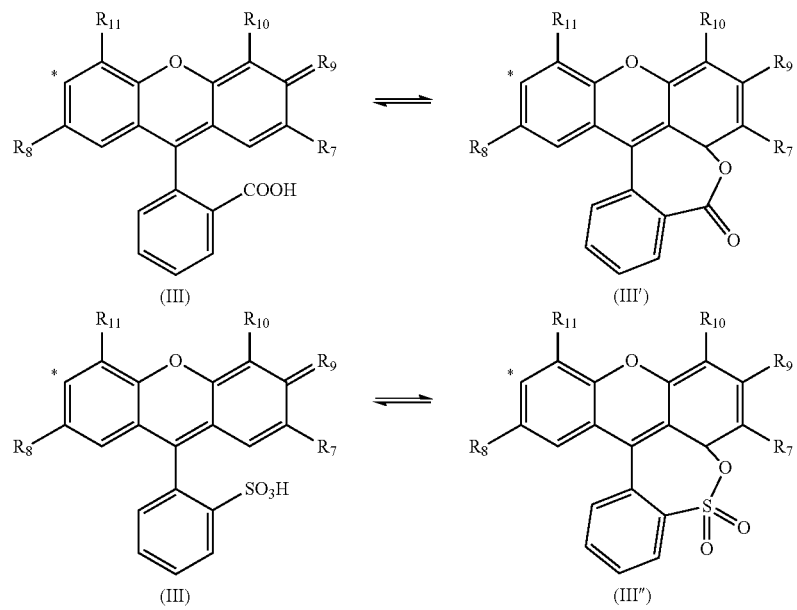

wherein $R_7$ to $R_{11}$ in the general formulae (III') and (III'') have the same meanings as $R_7$ to $R_{11}$ in the general formulae (III).

Description of General Formula (IV)

In the general formula (IV), $R_{12}$ and $R_{13}$ are, independently of each other, a hydrogen atom, an alkyl group, an aryl group or a heterocyclic group. $R_{14}$ to $R_{16}$ are, independently of one another, a hydrogen atom, an alkyl group, an aryl group, a heterocyclic group, a halogen atom or an amino group.

No particular limitation is imposed on the alkyl group in $R_{12}$, $R_{13}$, and $R_{14}$ to $R_{16}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

No particular limitation is imposed on the aryl group in $R_{12}$, $R_{13}$, and $R_{14}$ to $R_{16}$. However, examples thereof include 6- to 14-membered monocyclic or polycyclic aryl groups such as phenyl, naphthyl, phenanthryl and anthracenyl groups.

No particular limitation is imposed on the heterocyclic group in $R_{12}$, $R_{13}$, and $R_{14}$ to $R_{16}$. However, examples thereof include 4- to 10-membered monocyclic or bicyclic heterocyclic groups containing 1 to 4 atoms selected from nitrogen, oxygen and sulfur. Examples of these groups include pyridyl, pyrazinyl, pyrimidinyl, pyrrolyl, thienyl, furyl, pyranyl, oxazolyl, thiazolyl, triazolyl, tetrazolyl, imidazolyl, pyrazolyl, morpholinyl, thiomorpholinyl, piperidinyl, piperazinyl, quinolyl, isoquinolyl, indolyl, isoindolyl, benzofuryl and benzothienyl groups.

$R_{12}$ and $R_{13}$ are each favorably an alkyl group, with a methyl, ethyl, propyl or butyl group being particularly favorable.

Examples of the halogen atom in $R_{14}$ to $R_{16}$ include fluorine, chlorine, bromine and iodine atoms.

No particular limitation is imposed on the amino group in $R_{14}$ to $R_{16}$. However, examples thereof include an unsubstituted amino group; mono-substituted amino groups such as N-methylamino, N-butylamino, N-hexylamino, N-tetradecylamino, N-phenylamino and N-naphthylamino groups; di-substituted amino groups such as N,N-dimethylamino, N,N-diethylamino, N,N-diphenylamino and N,N-methylpropylamino groups; carbonylamino groups such as acetylamino, ethylcarbonylamino, tert-butylcarbonylamino, benzoylamino, naphthoylamino and methoxycarbonylamino groups; and sulfonylamino groups such methylsulfonylamino, ethylsulfonylamino, tert-butylsulfonylamino and isopropoxysulfonylamino groups.

$R_{14}$ to $R_{16}$ are each favorably a hydrogen atom, an alkyl group, a halogen atom or an amino group, with the hydrogen atom being particularly favorable.

Description of General Formula (V)

In the general formula (V), $R_{17}$ and $R_{18}$ are, independently of each other, a hydrogen atom, an alkyl group or an alkoxy group. $R_{19}$ and $R_{20}$ are, independently of each other, a hydrogen atom, an alkyl group, an alkoxy group, a hydroxyl group or a cyano group. $R_{21}$ is a heterocyclic group or —CH=C($R_{22}$)($R_{23}$). $R_{22}$ and $R_{23}$ are, independently of each other, a hydrogen atom, a cyano group, a heterocyclic group, a carboxyl group or a carboxylate group. $R_1$ and $R_{17}$, $R_2$ and $R_{18}$, and $R_{22}$ and $R_{23}$ may, independently of one another, bond to each other to form a ring.

No particular limitation is imposed on the alkyl group in $R_{17}$ to $R_{20}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

No particular limitation is imposed on the alkoxy group in $R_{17}$ to $R_{20}$. However, examples thereof include alkoxy groups having 1 to 20 carbon atoms, such as methoxy, ethoxy, propoxy, butoxy, pentyloxy, hexyloxy, heptyloxy, octyloxy, nonyloxy, decyloxy, dodecyloxy and octadecyloxy groups.

$R_{17}$ to $R_{20}$ are each favorably a hydrogen atom or an alkoxy group, with the hydrogen atom being particularly favorable from the viewpoint of stability of the compound.

No particular limitation is imposed on the heterocyclic group in $R_{21}$ to $R_{23}$. However, examples thereof include 4- to 10-membered monocyclic or bicyclic heterocyclic groups containing 1 to 4 atoms selected from nitrogen, oxygen and sulfur. Examples of these groups include pyridyl, pyrazinyl, pyrimidinyl, pyrrolyl, thienyl, furyl, pyranyl, oxazolyl, thiazolyl, triazolyl, tetrazolyl, imidazolyl, pyrazolyl, morpholinyl, thiomorpholinyl, piperidinyl, piperazinyl, quinolyl, isoquinolyl, indolyl, isoindolyl, benzofuryl and benzothienyl groups.

The heterocyclic group in $R_{21}$ is favorably an oxazolyl, thiazolyl or imidazolyl group, with the oxazolyl group being particularly favorable from the viewpoint of staining ability.

No particular limitation is imposed on the carboxylate group in $R_{21}$ to $R_{23}$. However, examples thereof include methyl carboxylate, ethyl carboxylate, propyl carboxylate and butyl carboxylate groups.

$R_{21}$ to $R_{23}$ are each favorably a pyridyl, pyrazinyl, pyrimidinyl, oxazolyl, thiazolyl, triazolyl, tetrazolyl, imidazolyl or pyrazolyl group, with the oxazolyl, thiazolyl or imidazolyl group being particularly favorable from the viewpoint of stability of the compound.

No particular limitation is imposed on the ring formed by bonding, independently of one another, $R_1$ and $R_{17}$, $R_2$ and $R_{18}$, and $R_{22}$ and $R_{23}$ to each other. However, examples thereof include aromatic rings having 3 to 10 carbon atoms, such as benzene and naphthalene rings; saturated rings such as cyclooctane, cycloheptane, cyclohexane, cyclopentane and cyclobutane rings; partially saturated rings such as cyclopentene and cyclohexene rings; and heterocycles such as pyridine, tetrahydropyridine and pyrimidine rings. These rings may additionally have substituent(s), and no particular limitation is imposed on the substituent(s) so far as the storage stability of the staining compound is not markedly impaired. Examples thereof include substituents described as "favorable examples of additional substituents" above.

The ring favorably has a substituent having such a nature that the water solubility is improved, among these substituents. Particularly favorable examples of such a substituent include carboxyl, sulfonic, polyethylene glycol, carboxylate and sulfonate groups though not limited thereto.

The ring formed by bonding, independently of one another, $R_1$ and $R_{17}$, $R_2$ and $R_{18}$, and $R_{22}$ and $R_{23}$ to each other is favorably a heterocycle, with a tetrahydropyridine ring being particularly favorable.

Description of General Formula (VI)

In the general formula (VI), $R_{24}$ is a hydrogen atom, an alkyl group, an aryl group or a heterocyclic group.

No particular limitation is imposed on the alkyl group in $R_{24}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups. The group may additionally have substituent(s), and no particular limitation is imposed on the substituent(s) so far as the storage stability of the staining compound is not markedly impaired. Examples thereof include substituents described as "favorable examples of additional substituents" above.

The group favorably has a substituent having such a nature that the water solubility is improved, among these substituents. Particularly favorable examples of such a substituent include carboxyl, sulfonic, polyethylene glycol, carboxylate and sulfonate groups though not limited thereto.

No particular limitation is imposed on the aryl group in $R_{24}$. However, examples thereof include 6- to 14-membered monocyclic or polycyclic aryl groups such as phenyl, naphthyl, phenanthryl and anthracenyl groups.

No particular limitation is imposed on the heterocyclic group in $R_{24}$. However, examples thereof include 4- to 10-membered monocyclic or bicyclic heterocyclic groups containing 1 to 4 atoms selected from nitrogen, oxygen and sulfur. Examples of these groups include pyridyl, pyrazinyl, pyrimidinyl, pyrrolyl, thienyl, furyl, pyranyl, oxazolyl, thiazolyl, triazolyl, tetrazolyl, imidazolyl, pyrazolyl, morpholinyl, thiomorpholinyl, piperidinyl, piperazinyl, quinolyl, isoquinolyl, indolyl, isoindolyl, benzofuryl and benzothienyl groups.

$R_{24}$ is favorably an alkyl group, with a methyl, ethyl, propyl, butyl, pentyl or hexyl group being particularly favorable from the viewpoint of stability of the compound.

Description of General Formula (VII)

In the general formula (VII), $R_{25}$ is an oxygen atom, a sulfur atom or $N(R_{27})$. $R_{26}$ is a hydrogen atom, an alkyl group, an alkoxy group or a sulfonic group. $R_{27}$ is a hydrogen atom, an alkyl group or an aryl group.

$R_{25}$ is favorably an oxygen atom or $N(R_{27})$, with NH being particularly favorable from the viewpoint of staining ability.

No particular limitation is imposed on the alkyl group in $R_{26}$ and $R_{27}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

No particular limitation is imposed on the alkoxy group in $R_{26}$. However, examples thereof include alkoxy groups having 1 to 20 carbon atoms, such as methoxy, ethoxy, propoxy, butoxy, pentyloxy, hexyloxy, heptyloxy, octyloxy, nonyloxy, decyloxy, dodecyloxy and octadecyloxy groups.

$R_{26}$ is favorably a hydrogen atom or a sulfonic group, with the hydrogen atom being particularly favorable.

No particular limitation is imposed on the aryl group in $R_{27}$. However, examples thereof include 6- to 14-membered monocyclic or polycyclic aryl groups such as phenyl, naphthyl, phenanthryl and anthracenyl groups.

Description of General Formula (VIII)

In the general formula (VIII), $R_{28}$ is a hydrogen atom, an alkyl group or an aryl group.

No particular limitation is imposed on the alkyl group in $R_{28}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups. The group may additionally have substituent(s), and no particular limitation is imposed on the substituent(s) so far as the storage stability of the staining compound is not markedly impaired. Examples thereof include substituents described as "favorable examples of additional substituents" above.

The group favorably has a substituent having such a nature that the water solubility is improved, among these substituents. Particularly favorable examples of such a substituent include carboxyl, sulfonic, polyethylene glycol, carboxylate and sulfonate groups though not limited thereto.

No particular limitation is imposed on the aryl group in $R_{28}$. However, examples thereof include 6- to 14-membered monocyclic or polycyclic aryl groups such as phenyl, naphthyl, phenanthryl and anthracenyl groups.

Description of General Formula (VIII')

In the general formula (VIII'), $R_{28}'$ is a halogen atom, an alkoxy group or an aryloxy group.

The halogen atom in $R_{28}'$ is a chlorine, bromine or iodine atom.

No particular limitation is imposed on the alkoxy group in $R_{28}'$. However, examples thereof include alkoxy groups having 1 to 20 carbon atoms, such as methoxy, ethoxy, propoxy, butoxy, pentyloxy, decyloxy, hexyloxy, heptyloxy, octyloxy, nonyloxy, decyloxy, dodecyloxy and octadecyloxy groups. The group may additionally have substituent(s), and no particular limitation is imposed on the substituent(s) so far as the storage stability of the staining compound is not markedly impaired. Examples thereof include substituents described as "favorable examples of additional substituents" above.

The group favorably has a substituent having such a nature that the water solubility is improved, among these substituents. Particularly favorable examples of such a substituent include carboxyl, sulfonic, polyethylene glycol, carboxylate and sulfonate groups though not limited thereto.

No particular limitation is imposed on the aryl group in $R_{28}'$. However, examples thereof include 6- to 14-membered monocyclic or polycyclic aryl groups such as phenyl, naphthyl, phenanthryl and anthracenyl groups.

Description of General Formula (IX)

In the general formula (IX), $R_{29}$ is a hydrogen atom, an alkyl group or an aryl group.

No particular limitation is imposed on the alkyl group in $R_{29}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups. The group may additionally have substituent(s), and no particular limitation is imposed on the substituent(s) so far as the storage stability of the staining compound is not markedly impaired. Examples thereof include substituents described as "favorable examples of additional substituents" above.

The group favorably has a substituent having such a nature that the water solubility is improved, among these substituents. Particularly favorable examples of such a substituent include carboxyl, sulfonic, polyethylene glycol, carboxylate and sulfonate groups though not limited thereto.

No particular limitation is imposed on the aryl group in $R_{29}$. However, examples thereof include 6- to 14-membered monocyclic or polycyclic aryl groups such as phenyl, naphthyl, phenanthryl and anthracenyl groups.

Another Mode of A in the General Formula (I)

When A is a structure represented by the following general formula (X), $R_1$ and $R_2$ in the general formula (I) bond to each other to form one substituent group: $=N-R_{30}$. $R_{30}$ is an aryl group or a heterocyclic group.

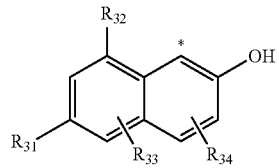

(X)

In the general formula (X), $R_{31}$ and $R_{32}$ are individually a sulfonic group or a salt thereof. $R_{33}$ and $R_{34}$ are individually a hydrogen atom, an alkyl group, an alkoxy group or a halogen atom.

No particular limitation is imposed on the alkyl group in $R_{33}$ and $R_{34}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

No particular limitation is imposed on the alkoxy group in $R_{33}$ to $R_{34}$. However, examples thereof include alkoxy groups having 1 to 20 carbon atoms, such as methoxy, ethoxy, propoxy, butoxy, pentyloxy, decyloxy, hexyloxy, heptyloxy, octyloxy, nonyloxy, decyloxy, dodecyloxy and octadecyloxy groups.

Examples of the halogen atom in $R_{33}$ and $R_{34}$ include fluorine, chlorine, bromine and iodine atoms.

$R_{33}$ to $R_{34}$ are each favorably a hydrogen atom, an alkoxy group or a halogen atom, with the hydrogen atom being particularly favorable.

No particular limitation is imposed on the aryl group in $R_{30}$. However, examples thereof include 6- to 14-membered monocyclic or polycyclic aryl groups such as phenyl, naphthyl, phenanthryl and anthracenyl groups.

$R_{30}$ is favorably an aryl group, with a naphthyl group being particularly favorable.

Description of General Formula (II)

In addition, in the general formula (II), $R_3$ and $R_4$ are, independently of each other, a hydrogen atom, an alkenyl group, a cyano group, a carboxyl group, a carboxylate group, a sulfonic group, an acyl group or a heterocyclic group. $R_3$ and $R_4$ may bond to each other to form a ring. $R_5$ is a hydrogen atom, an alkyl group, an aryl group or a heterocyclic group.

No particular limitation is imposed on the alkenyl group in $R_3$ and $R_4$ of the general formula (II). However, examples thereof include alkenyl groups having 2 to 20 carbon atoms, such as vinyl, 2,2-diphenylvinyl, 3-butenyl and cyclohexenyl groups.

No particular limitation is imposed on the carboxylate group in $R_3$ and $R_4$. However, examples thereof include methyl carboxylate, ethyl carboxylate, propyl carboxylate and butyl carboxylate groups.

No particular limitation is imposed on the acyl group in $R_3$ and $R_4$. However, examples thereof include acetyl, propionyl, butyryl, pentanoyl, benzoyl, 1-naphthoyl and 2-naphthoyl groups.

No particular limitation is imposed on the heterocyclic group in $R_3$ and $R_4$. However, examples thereof include 4- to 10-membered monocyclic or bicyclic heterocyclic groups containing 1 to 4 atoms selected from nitrogen, oxygen and sulfur. Examples of these groups include pyridyl, pyrazinyl, pyrimidinyl, pyrrolyl, thienyl, furyl, pyranyl, oxazolyl, thiazolyl, triazolyl, tetrazolyl, imidazolyl, pyrazolyl, morpholinyl, thiomorpholinyl, piperidinyl, piperazinyl, quinolyl, isoquinolyl, indolyl, isoindolyl, benzofuryl and benzothienyl groups.

Either one of $R_3$ and $R_4$ is favorably a cyano, carboxyl or heterocyclic group from the viewpoint of ease of synthesis of the compound, and either one of $R_3$ and $R_4$ is particularly favorably a cyano group.

Description of the Case where One of $R_3$ and $R_4$ in General Formula (II) is Hydrogen Atom, and the Other is Heterocyclic Group of General Formula (XI)

$R_3$ and $R_4$ are favorably such that one of them is a hydrogen atom and the other is a heterocyclic group of the general formula (XI).

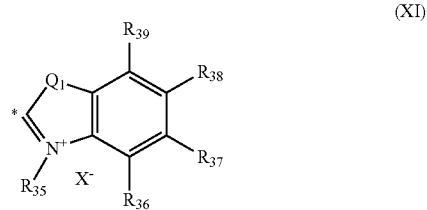

wherein in the general formula (XI), $R_{35}$ is an alkyl group or an aryl group, $R_{36}$ to $R_{39}$ are, independently of one another, a hydrogen atom, an alkyl group, an aryl group, an alkoxy group, a carboxyl group, a sulfonic group, a heterocyclic group, an amino group or a halogen atom, $R_{36}$ and $R_{37}$, $R_{37}$ and $R_{38}$, or $R_{38}$ and $R_{39}$ may bond to each other to form a ring, $X^-$ is an anionic group, and $Q_1$ is a sulfur atom, an oxygen atom, $-C(R_{40})(R_{41})-$, $-CH=CH-$ or $-N(R_{42})-$, in which $R_{40}$ to $R_{42}$ are individually a hydrogen atom, an alkyl group or an aryl group, and $R_{40}$ and $R_{41}$ may bond to each other to form a ring.

No particular limitation is imposed on the alkyl group in $R_{35}$, and $R_{36}$ to $R_{39}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

No particular limitation is imposed on the aryl group in $R_{35}$, and $R_{36}$ to $R_{39}$. However, examples thereof include 6- to 14-membered monocyclic or polycyclic aryl groups such as phenyl, naphthyl, phenanthryl and anthracenyl groups.

$R_{35}$ may additionally have substituent(s), and no particular limitation is imposed on the substituent(s) so far as the storage stability of the staining compound is not markedly impaired. Examples thereof include substituents described as "favorable examples of additional substituents" above.

The group favorably has a substituent having such a nature that the water solubility is improved, among these substituents. Particularly favorable examples of such a substituent include carboxyl, sulfonic, polyethylene glycol, carboxylate and sulfonate groups though not limited thereto.

$R_{35}$ is favorably an alkyl group, and it is favorable that the alkyl group additionally has a substituent such as a carboxyl, sulfonic, polyethylene glycol, carboxylate or sulfonate group, since the water solubility of the resulting compound is increased, and the fluorescence intensity thereof is also increased.

No particular limitation is imposed on the alkoxy group in $R_{36}$ to $R_{39}$. However, examples thereof include alkoxy groups having 1 to 20 carbon atoms, such as methoxy, ethoxy, propoxy, butoxy, pentyloxy, decyloxy, hexyloxy, heptyloxy, octyloxy, nonyloxy, decyloxy, dodecyloxy and octadecyloxy groups.

No particular limitation is imposed on the heterocyclic group in $R_{36}$ to $R_{39}$. However, examples thereof include 4- to 10-membered monocyclic or bicyclic heterocyclic groups containing 1 to 4 atoms selected from nitrogen, oxygen and sulfur. Examples of these groups include pyridyl, pyrazinyl, pyrimidinyl, pyrrolyl, thienyl, furyl, pyranyl, oxazolyl, thiazolyl, triazolyl, tetrazolyl, imidazolyl, pyrazolyl, morpholinyl, thiomorpholinyl, piperidinyl, piperazinyl, quinolyl, isoquinolyl, indolyl, isoindolyl, benzofuryl and benzothienyl groups.

No particular limitation is imposed on the amino group in $R_{36}$ to $R_{39}$. However, examples thereof include an unsubstituted amino group; mono-substituted amino groups such as N-methylamino, N-butylamino, N-hexylamino, N-tetradecylamino, N-phenylamino and N-naphthylamino groups; di-substituted amino groups such as N,N-dimethylamino, N,N-diethylamino, N,N-diphenylamino and N,N-methylpropylamino groups; carbonylamino groups such as acetylamino, ethylcarbonylamino, tert-butylcarbonylamino, benzoylamino, naphthoylamino and methoxycarbonylamino groups; and sulfonylamino groups such methylsulfonylamino, ethylsulfonylamino, tert-butylsulfonylamino and isopropoxysulfonylamino groups.

Examples of the halogen atom in $R_{36}$ to $R_{39}$ include fluorine, chlorine, bromine and iodine atoms.

$R_{36}$ to $R_{39}$ are each favorably a hydrogen atom, a carboxyl group, a sulfonic group, an amino group or a halogen atom, and a hydrogen atom or a sulfonic group is particularly favorable because the water solubility of the resulting compound is improved.

No particular limitation is imposed on the ring formed by bonding $R_{36}$ and $R_{37}$, $R_{37}$ and $R_{38}$, or $R_{38}$ and $R_{39}$ to each other. However, examples thereof include aromatic rings having 3 to 10 carbon atoms, such as benzene and naphthalene rings; saturated rings such as cyclooctane, cycloheptane, cyclohexane, cyclopentane and cyclobutane rings; partially saturated rings such as cyclopentene and cyclohexene rings; and heterocycles such as pyridine and pyrimidine rings. The ring may additionally have substituent(s), and no particular limitation is imposed on the substituent(s) so far as the storage stability of the staining compound is not markedly impaired. Examples thereof include substituents described as "favorable examples of additional substituents" above.

The ring favorably has a substituent having such a nature that the water solubility is improved, among these substituents. Particularly favorable examples of such a substituent include carboxyl, sulfonic, polyethylene glycol, carboxylate and sulfonate groups though not limited thereto.

The ring formed by bonding $R_{36}$ and $R_{37}$, $R_{37}$ and $R_{38}$, or $R_{38}$ and $R_{39}$ to each other is favorably a benzene ring because the storage stability of the resulting compound is improved.

Description of $X^-$ in General Formula (XI)

In the general formula (XI), $X^-$ is an anionic group. No particular limitation is imposed on the anionic group. However, examples thereof include halide ions such as fluoride, chloride, bromide and iodide ions; inorganic acid ions such as sulfate, phosphate, nitrate, tetrafluoroborate and hexafluorophosphate ions; Lewis-acid-containing ions such as tetrachloroaluminate ion; and organic acid ions such as acetate, lactate, methanesulfonate, benzenesulfonate, p-toluenesulfonate, trifluoroacetate, trifluoromethanesulfonate and tetraphenylborate ions.

The anionic group of $X^-$ is favorably a chloride, bromide, iodide, sulfate, nitrate or methanesulfonate ion and more favorably a bromide or iodide ion from the viewpoint of ease of synthesis of the compound.

Description of $Q_1$ in General Formula (XI)

In the general formula (XI), $Q_1$ is a sulfur atom, oxygen atom, $-C(R_{40})(R_{41})-$, $-CH=CH-$ or $-N(R_{42})-$.

No particular limitation is imposed on the alkyl group in $R_{40}$ to $R_{42}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

No particular limitation is imposed on the aryl group in $R_{40}$ to $R_{42}$. However, examples thereof include 6- to 14-membered monocyclic or polycyclic aryl groups such as phenyl, naphthyl, phenanthryl and anthracenyl groups.

$R_{40}$ and $R_{41}$ in $Q_1$ may bond to each other to form a ring, and examples thereof include cyclohexane, piperidine and piperidinium rings.

$Q_1$ is particularly favorably an oxygen atom, sulfur atom or $-C(CH_3)(CH_3)-$ because the storage stability of the compound is improved.

It is also favorable that $Q_1$ is $-C(CH_2)_5-$, since the staining ability of the compound becomes excellent.

Description of Ring Formed by Bonding $R_3$ and $R_4$ in General Formula (II) to Each Other The ring formed by bonding $R_3$ and $R_4$ in the general formula (II) to each other is represented by any one of the following general formulae (XII), (XIII) and (XV).

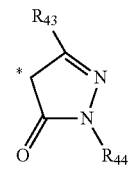

(XII)

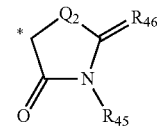

(XIII)

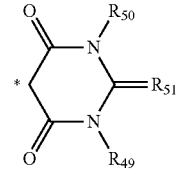

(XV)

In the general formula (XII), $R_{43}$ is a hydrogen atom, an alkyl group, an aryl group or a heterocyclic group, and $R_{44}$ is an alkyl group, an aryl group, a carboxyl group, a carboxylate group, a hydroxyl group or an amino group.

No particular limitation is imposed on the alkyl group in $R_{43}$ and $R_{44}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

No particular limitation is imposed on the aryl group in $R_{43}$ and $R_{44}$. However, examples thereof include 6- to 14-membered monocyclic or polycyclic aryl groups such as phenyl, naphthyl, phenanthryl and anthracenyl groups.

The ring may additionally have substituent(s), and no particular limitation is imposed on the substituent(s) so far as the storage stability of the staining compound is not markedly impaired. Examples thereof include substituents described as "favorable examples of additional substituents" above.

The ring favorably has a substituent having such a nature that the water solubility is improved, among these substituents. Particularly favorable examples of such a substituent include carboxyl, sulfonic, polyethylene glycol, carboxylate and sulfonate groups though not limited thereto.

No particular limitation is imposed on the heterocyclic group in $R_{43}$. However, examples thereof include 4- to 10-membered monocyclic or bicyclic heterocyclic groups containing 1 to 4 atoms selected from nitrogen, oxygen and sulfur. Examples of these groups include pyridyl, pyrazinyl, pyrimidinyl, pyrrolyl, thienyl, furyl, pyranyl, oxazolyl, thiazolyl, triazolyl, tetrazolyl, imidazolyl, pyrazolyl, morpholinyl, thiomorpholinyl, piperidinyl, piperazinyl, quinolyl, isoquinolyl, indolyl, isoindolyl, benzofuryl and benzothienyl groups.

$R_{43}$ is favorably an aryl group from the viewpoint of stability of the compound. It is also favorable that the aryl group has a water-soluble substituent such as a carboxyl group, since the water solubility of the compound is improved.

No particular limitation is imposed on the carboxylate group in $R_{44}$. However, examples thereof include methyl carboxylate, ethyl carboxylate, propyl carboxylate and butyl carboxylate groups.

No particular limitation is imposed on the amino group in $R_{44}$. However, examples thereof include an unsubstituted amino group; mono-substituted amino groups such as N-methylamino, N-butylamino, N-hexylamino, N-tetradecylamino, N-phenylamino and N-naphthylamino groups; di-substituted amino groups such as N,N-dimethylamino, N,N-diethylamino, N,N-diphenylamino and N,N-methylpropylamino groups; carbonylamino groups such as acetylamino, ethylcarbonylamino, tert-butylcarbonylamino, benzoylamino, naphthoylamino and methoxycarbonylamino groups; and sulfonylamino groups such methylsulfonylamino, ethylsulfonylamino, tert-butylsulfonylamino and isopropoxysulfonylamino groups.

$R_{44}$ is favorably an alkyl, aryl, carboxyl or amino group from the viewpoint of easy of synthesis of the compound, with the alkyl or carboxyl group being particularly favorable.

Description of General Formula (XIII)

In the general formula (XIII), $Q_2$ is an oxygen atom, a sulfur atom or —N($R_{52}$)—. $R_{45}$ is a hydrogen atom, an alkyl group, an aryl group or a heterocyclic group, $R_{46}$ is a sulfur atom, an oxygen atom, =NR$_{53}$, a heterocyclic group or a dicyanomethylene group, and $R_{52}$ and $R_{53}$ are individually a hydrogen atom, an alkyl group, an aryl group or a heterocyclic group.

No particular limitation is imposed on the alkyl group in $R_{45}$, $R_{52}$ and $R_{53}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups. The group may additionally have substituent(s), and no particular limitation is imposed on the substituent(s) so far as the storage stability of the staining compound is not markedly impaired. Examples thereof include substituents described as "favorable examples of additional substituents" above.

The group favorably has a substituent having such a nature that the water solubility is improved, among these substituents. Particularly favorable examples of such a substituent include carboxyl, sulfonic, polyethylene glycol, carboxylate and sulfonate groups though not limited thereto.

No particular limitation is imposed on the aryl group in $R_{45}$, $R_{52}$ and $R_{53}$. However, examples thereof include 6- to 14-membered monocyclic or polycyclic aryl groups such as phenyl, naphthyl, phenanthryl and anthracenyl groups.

No particular limitation is imposed on the heterocyclic group in $R_{45}$, $R_{52}$ and $R_{53}$. However, examples thereof include 4- to 10-membered monocyclic or bicyclic heterocyclic groups containing 1 to 4 atoms selected from nitrogen, oxygen and sulfur. Examples of these groups include pyridyl, pyrazinyl, pyrimidinyl, pyrrolyl, thienyl, furyl, pyranyl, oxazolyl, thiazolyl, triazolyl, tetrazolyl, imidazolyl, pyrazolyl, morpholinyl, thiomorpholinyl, piperidinyl, piperazinyl, quinolyl, isoquinolyl, indolyl, isoindolyl, benzofuryl and benzothienyl groups.

$R_{45}$ is favorably an alkyl group, and it is favorable that the alkyl group additionally has a substituent such as a carboxyl, sulfonic, polyethylene glycol, carboxylate or sulfonate group, since the water solubility of the resulting compound is increased, and the fluorescence intensity thereof is also increased.

$R_{46}$ is favorably a sulfur atom, oxygen atom or heterocycle.

It is favorable that $R_{46}$ is a sulfur atom, since the compound tends to improve the staining ability thereof, and that $R_{46}$ is 2-thioxothiazolidin-4-one having a substituent at the 3-position, since detection of a maximum fluorescence wavelength is often conducted in such a larger wavelength region as a near-infrared wavelength region, so that the compound can be used in near-infrared applications.

Description of General Formula (XV)

In the general formula (XV), $R_{49}$ and $R_{50}$ are, independently of each other, a hydrogen atom, an alkyl group or an aryl group, and $R_{51}$ is an oxygen atom or a sulfur atom.

No particular limitation is imposed on the alkyl group in $R_{49}$ and $R_{50}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

No particular limitation is imposed on the aryl group in $R_{49}$ and $R_{50}$. However, examples thereof include 6- to 14-membered monocyclic or polycyclic aryl groups such as phenyl, naphthyl, phenanthryl and anthracenyl groups.

(Description of B in General Formula (II))

B is a structure represented by any one of the following general formulae (XVI) to (XVIV) and (XVII')

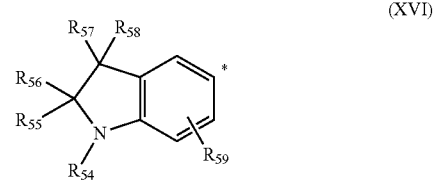

(XVI)

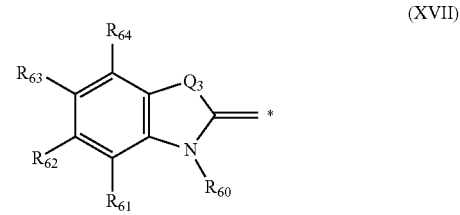

(XVII)

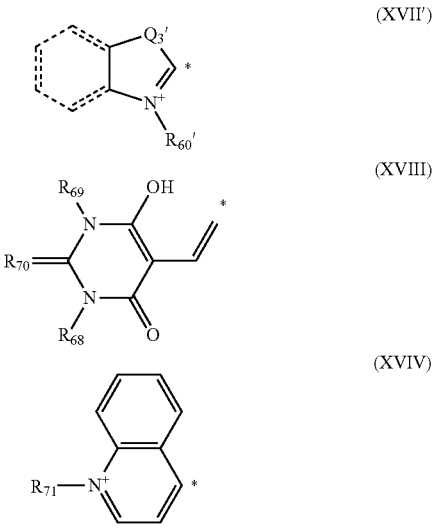

Each structure will hereinafter be described in detail.

Description of General Formula (XVI)

In the general formula (XVI), $R_{54}$ is a hydrogen atom, an alkyl group, an aralkyl group, an alkenyl group, an aryl group, a heterocyclic group or an acyl group. $R_{55}$ to $R_{58}$ are, independently of one another, a hydrogen atom, an alkyl group, an aryl group, a carboxyl group, a carboxylate group or an acyl group, and $R_{55}$ and $R_{57}$ may bond to each other to form a ring. $R_{59}$ is a hydrogen atom, an alkyl group, an alkoxy group or a halogen atom.

No particular limitation is imposed on the alkyl group in $R_{54}$, $R_{55}$ to $R_{58}$, and $R_{59}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

No particular limitation is imposed on the aralkyl group in $R_{54}$. However, examples thereof include benzyl and phenethyl groups.

No particular limitation is imposed on the alkenyl groups in $R_{54}$. However, examples thereof include alkenyl groups having 2 to 20 carbon atoms, such as vinyl, 2,2-diphenylvinyl, 3-butenyl and cyclohexenyl groups.

No particular limitation is imposed on the aryl group in $R_{54}$, and $R_{55}$ to $R_{58}$. However, examples thereof include 6- to 14-membered monocyclic or polycyclic aryl groups such as phenyl, naphthyl, phenanthryl and anthracenyl groups.

No particular limitation is imposed on the heterocyclic group in $R_{54}$. However, examples thereof include 4- to 10-membered monocyclic or bicyclic heterocyclic groups containing 1 to 4 atoms selected from nitrogen, oxygen and sulfur. Examples of these groups include pyridyl, pyrazinyl, pyrimidinyl, pyrrolyl, thienyl, furyl, pyranyl, oxazolyl, thiazolyl, triazolyl, tetrazolyl, imidazolyl, pyrazolyl, morpholinyl, thiomorpholinyl, piperidinyl, piperazinyl, quinolyl, isoquinolyl, indolyl, isoindolyl, benzofuryl and benzothienyl groups.

No particular limitation is imposed on the acyl group in $R_{54}$, and $R_{55}$ to $R_{58}$. However, examples thereof include acetyl, propionyl, butyryl, pentanoyl, benzoyl, 1-naphthoyl and 2-naphthoyl groups.

$R_{54}$, and $R_{55}$ to $R_{58}$ may additionally have substituent(s), and no particular limitation is imposed on the substituent(s) so far as the storage stability of the staining compound is not markedly impaired. Examples thereof include substituents described as "favorable examples of additional substituents" above.

The groups favorably have a substituent having such a nature that the water solubility is improved, among these substituents. Particularly favorable examples of such a substituent include carboxyl, sulfonic, polyethylene glycol, carboxylate and sulfonate groups though not limited thereto.

$R_{54}$, and $R_{55}$ to $R_{58}$ may be selected independently of one another and arbitrarily from the substituents mentioned above. However, as a favorable mode, the aralkyl, alkenyl or aryl group is favorable because the fluorescence intensity of the resulting compound becomes strong. Favorable specific examples thereof include phenyl, bromophenyl, benzyl, bromobenzyl, methylthiophenyl, methoxyphenyl, methoxynaphthyl, benzylphenyl, 2,2-diphenylvinyl and 2,2-diphenylvinylphenyl groups. More favorable examples thereof include phenyl, bromophenyl, benzyl, methylthiophenyl, methoxyphenyl and methoxynaphthyl groups, with the methylthiophenyl group being particularly favorable because a tendency for a Stokes shift (a difference between maximum excitation wavelength and maximum fluorescence wavelength) to remarkably become large is recognized.

No particular limitation is imposed on the carboxylate group in $R_{55}$ to $R_{58}$. However, examples thereof include methyl carboxylate, ethyl carboxylate, propyl carboxylate and butyl carboxylate groups.

No particular limitation is imposed on the ring formed by bonding $R_{55}$ and $R_{57}$ to each other. However, examples thereof include saturated aliphatic rings such as cyclooctane, cycloheptane, cyclohexane, cyclopentane and cyclobutane rings; and partially saturated aliphatic rings such as cyclopentene and cyclohexene rings. These rings may additionally have substituent(s), and no particular limitation is imposed on the substituent(s) so far as the storage stability of the staining compound is not markedly impaired. Examples thereof include substituents described as "favorable examples of additional substituents" above.

The ring favorably has a substituent having such a nature that the water solubility is improved, among these substituents. Particularly favorable examples of such a substituent include carboxyl, sulfonic, polyethylene glycol, carboxylate and sulfonate groups though not limited thereto.

It is favorable that $R_{55}$ to $R_{58}$ are, independently of each other, a hydrogen atom, alkyl group or aryl group, and $R_{55}$ and $R_{57}$ bond to each other to form a ring. It is more favorable that $R_{55}$ and $R_{57}$ bond to each other to form a ring, since the resulting compound becomes stable in chemical structure. Specific examples of the ring include cyclooctane, cycloheptane, cyclohexane, cyclopentane and cyclobutane rings, and the cyclopentane ring is more favorable from the viewpoint of storage stability.

No particular limitation is imposed on the alkoxy group in $R_{59}$. However, examples thereof include alkoxy groups having 1 to 20 carbon atoms, such as methoxy, ethoxy, propoxy, butoxy, pentyloxy, hexyloxy, heptyloxy, octyloxy, nonyloxy, decyloxy, dodecyloxy and octadecyloxy groups.

Examples of the halogen atom in $R_{59}$ include fluorine, chlorine, bromine and iodine atoms.

$R_{59}$ is favorably a hydrogen atom, a halogen atom or an alkoxy group, with the hydrogen or halogen atom being more favorable.

Description of General Formula (XVII)

In the general formula (XVII), $R_{60}$ is a hydrogen atom, an alkyl group or an aryl group. $R_{61}$ to $R_{64}$ are, independently of one another, a hydrogen atom, an alkyl group, an aryl group, an alkoxy group, a carboxyl group, a sulfonic group, a heterocyclic group, an amino group or a halogen atom. $R_{61}$ and $R_{62}$, $R_{62}$ and $R_{63}$, or $R_{63}$ and $R_{64}$ may bond to each other to form a ring.

No particular limitation is imposed on the alkyl group in $R_{60}$, and $R_{61}$ to $R_{64}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

No particular limitation is imposed on the aryl group in $R_{60}$, and $R_{61}$ to $R_{64}$. However, examples thereof include 6- to 14-membered monocyclic or polycyclic aryl groups such as phenyl, naphthyl, phenanthryl and anthracenyl groups.

$R_{60}$ may additionally have substituent(s), and no particular limitation is imposed on the substituent(s) so far as the storage stability of the staining compound is not markedly impaired. Examples thereof include substituents described as "favorable examples of additional substituents" above.

The group favorably has a substituent having such a nature that the water solubility is improved, among these substituents. Particularly favorable examples of such a substituent include carboxyl, sulfonic, polyethylene glycol, carboxylate and sulfonate groups though not limited thereto.

$R_{60}$ is favorably an alkyl group, and it is favorable that the alkyl group additionally has a substituent such as a carboxyl, sulfonic, polyethylene glycol, carboxylate or sulfonate group, since the water solubility of the resulting compound is increased, and the fluorescence intensity thereof is also increased.

No particular limitation is imposed on the alkoxy group in $R_{61}$ to $R_{64}$. However, examples thereof include alkoxy groups having 1 to 20 carbon atoms, such as methoxy, ethoxy, propoxy, butoxy, pentyloxy, hexyloxy, heptyloxy, octyloxy, nonyloxy, decyloxy, dodecyloxy and octadecyloxy groups.

No particular limitation is imposed on the heterocyclic group in $R_{61}$ to $R_{64}$. However, examples thereof include 4- to 10-membered monocyclic or bicyclic heterocyclic groups containing 1 to 4 atoms selected from nitrogen, oxygen and sulfur. Examples of these groups include pyridyl, pyrazinyl, pyrimidinyl, pyrrolyl, thienyl, furyl, pyranyl, oxazolyl, thiazolyl, triazolyl, tetrazolyl, imidazolyl, pyrazolyl, morpholinyl, thiomorpholinyl, piperidinyl, piperazinyl, quinolyl, isoquinolyl, indolyl, isoindolyl, benzofuryl and benzothienyl groups.

No particular limitation is imposed on the amino group in $R_{61}$ to $R_{64}$. However, examples thereof include an unsubstituted amino group; mono-substituted amino groups such as N-methylamino, N-butylamino, N-hexylamino, N-tetradecylamino, N-phenylamino and N-naphthylamino groups; di-substituted amino groups such as N,N-dimethylamino, N,N-diethylamino, N,N-diphenylamino and N,N-methylpropylamino groups; carbonylamino groups such as acetylamino, ethylcarbonylamino, tert-butylcarbonylamino, benzoylamino, naphthoylamino and methoxycarbonylamino groups; and sulfonylamino groups such methylsulfonylamino, ethylsulfonylamino, tert-butylsulfonylamino and isopropoxysulfonylamino groups.

Examples of the halogen atom in $R_{61}$ to $R_{64}$ include fluorine, chlorine, bromine and iodine atoms.

$R_{61}$ to $R_{64}$ are each favorably a hydrogen atom, a carboxyl group, a sulfonic group, an amino group or a halogen atom, and a hydrogen atom or a sulfonic group is particularly favorable because the water solubility of the resulting compound is improved.

No particular limitation is imposed on the ring formed by bonding $R_{61}$ and $R_{62}$, $R_{62}$ and $R_{63}$, or $R_{63}$ and $R_{64}$ to each other. However, examples thereof include aromatic rings having 3 to 10 carbon atoms, such as benzene and naphthalene rings; saturated rings such as cyclooctane, cycloheptane, cyclohexane, cyclopentane and cyclobutane rings; partially saturated rings such as cyclopentene and cyclohexene rings; and heterocycles such as pyridine and pyrimidine rings. The ring may additionally have substituent(s), and no particular limitation is imposed on the substituent(s) so far as the storage stability of the staining compound is not markedly impaired. Examples thereof include substituents described as "favorable examples of additional substituents" above.

The ring favorably has a substituent having such a nature that the water solubility is improved, among these substituents. Particularly favorable examples of such a substituent include carboxyl, sulfonic, polyethylene glycol, carboxylate and sulfonate groups though not limited thereto.

The ring formed by bonding $R_{61}$ and $R_{62}$, $R_{62}$ and $R_{63}$, or $R_{63}$ and $R_{64}$ to each other is favorably a benzene ring because the storage stability of the resulting compound is improved.

Description of $Q_3$ in General Formula (XVII)

In the general formula (XVII), $Q_3$ is a sulfur atom, an oxygen atom, —C($R_{65}$)($R_{66}$)— or —CH=CH—, in which $R_{65}$ and $R_{66}$ bond to each other to form a ring.

Examples of the ring formed by bonding $R_{65}$ and $R_{66}$ in $Q_3$ to each other include cyclohexane, piperidine and piperidinium rings.

$Q_3$ is favorably a sulfur atom, oxygen atom or —C($R_{65}$)($R_{66}$)—, and particularly favorably an oxygen atom or sulfur atom.

It is also favorable that $Q_3$ is —C(CH$_2$)$_5$—, since the staining ability of the compound becomes excellent.

Description of General Formula (XVII')

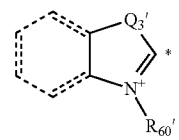

(XVII')

In the general formula (XVII'), $R_{60}$' is a hydrogen atom, an alkyl group or an aryl group, $Q_3$' is a sulfur atom or an oxygen atom. Dotted lines in the general formula (XVII') represent the case where a benzene ring is present or absent.

No particular limitation is imposed on the alkyl group in $R_{60}$'. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

No particular limitation is imposed on the aryl group in $R_{60}$'. However, examples thereof include 6- to 14-membered monocyclic or polycyclic aryl groups such as phenyl, naphthyl, phenanthryl and anthracenyl groups.

$R_{60}$' may additionally have substituent(s), and no particular limitation is imposed on the substituent(s) so far as the storage stability of the staining compound is not markedly impaired. Examples thereof include substituents described as "favorable examples of additional substituents" above.

The group favorably has a substituent having such a nature that the water solubility is improved, among these substituents. Particularly favorable examples of such a substituent include carboxyl, sulfonic, polyethylene glycol, carboxylate and sulfonate groups though not limited thereto.

$R_{60}'$ is favorably an alkyl group, and it is favorable that the alkyl group additionally has a substituent such as a carboxyl, sulfonic, polyethylene glycol, carboxylate or sulfonate group, since the water solubility of the resulting compound is increased, and the fluorescence intensity thereof is also increased.

Description of General Formula (XVIII)

In the general formula (XVIII), $R_{68}$ and $R_{69}$ are, independently of each other, a hydrogen atom, an alkyl group or an aryl group. $R_{70}$ is an oxygen atom or a sulfur atom.

No particular limitation is imposed on the alkyl group in $R_{68}$ and $R_{69}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

No particular limitation is imposed on the aryl group in $R_{68}$ and $R_{69}$. However, examples thereof include 6- to 14-membered monocyclic or polycyclic aryl groups such as phenyl, naphthyl, phenanthryl and anthracenyl groups.

$R_{68}$ and $R_{69}$ may additionally have substituent(s), and no particular limitation is imposed on the substituent(s) so far as the storage stability of the staining compound is not markedly impaired. Examples thereof include substituents described as "favorable examples of additional substituents" above.

The groups favorably have a substituent having such a nature that the water solubility is improved, among these substituents. Particularly favorable examples of such a substituent include carboxyl, sulfonic, polyethylene glycol, carboxylate and sulfonate groups though not limited thereto.

Description of General Formula (XVIV)

In the general formula (XVIV), $R_{71}$ is an alkyl group.

No particular limitation is imposed on the alkyl group in $R_{71}$. However, examples thereof include linear, branched or cyclic alkyl groups having 1 to 20 carbon atoms, such as methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, cyclopropyl, cyclobutyl and cyclopentyl groups.

Description of General Formulae (I) to (XVIV), (VIII'), and (XVII')

It is favorable that a compound of the general formulae (I) to (XVIV), (VIII'), and (XVII') has at least one of carboxyl, sulfonic and polyethylene glycol groups, since the water solubility of the compound is improved. A salt of the carboxyl or sulfonic group is also usable in the present invention. No particular limitation is imposed on the salt of the carboxyl or sulfonic group. Specific examples thereof include alkali metal salts such as sodium and potassium salts; alkaline earth salts such as magnesium and calcium salts; amine salts such as ammonium, pyridinium, piperidinium and triethylammonium salts; and amino acid salts such as tryptophan, lysine, leucine, phenylalanine, valine and arginine salts. Favorable examples thereof include sodium, potassium, ammonium, pyridinium and piperidinium salts.

<Synthetic Examples>

The staining compound s according to the present invention, which are represented by any one of the general formulae (I) to (XVIV), (VIII'), and (XVII'), may be commercially available and can be obtained with ease. The compounds can also be easily synthesized according to publicly known respective processes. For example, a staining compound in which A in the general formula (I) is represented by the general formula (III) can be easily synthesized by referring to, for example, Japanese Patent Application Laid-Open No. 2008-94897. A staining compound in which A in the general formula (I) is represented by the general formula (V) or (VII) can be synthesized according to the process described in, for example, Japanese Patent Application Laid-Open 2001-315437. On the other hand, a staining compound in which B in the general formula (II) is represented by the general formula (XVI) can be easily synthesized by referring to, for example, Chem. Comm., Vol. 24, pp. 3036-3037 (2003).

An aspect about a production process of the staining compound in which A in the general formula (I) is represented by the general formula (III) will hereinafter be described, but the synthetic process is not limited thereto. An exemplary synthetic scheme will hereinafter be shown.

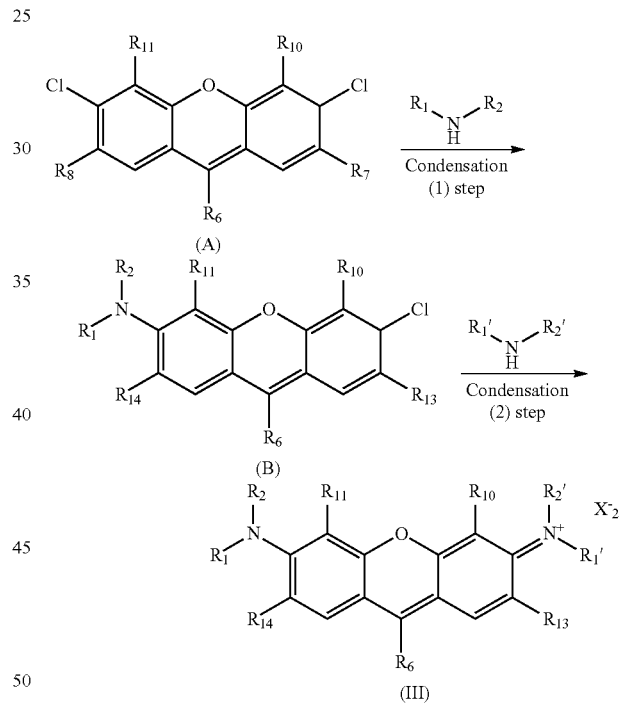

$R_1$, $R_2$, and $R_6$ to $R_{11}$ in the above scheme have the same meanings as described above.

First, in Condensation (1) step, a compound (A) and an amine derivative are heated and condensed in the presence of a condensing agent (or in the absence of the condensing agent) in an organic solvent (or in the absence of a solvent) to obtain a compound (B). The compound (B) is then heated and condensed again with the above-described amine derivative. As a result, a staining compound (III) according to the present invention is obtained.

No particular limitation is imposed on a favorable organic solvent usable in the condensation reaction of the above-illustrated synthetic scheme so far as the solvent does not participate in the reaction in Condensation (1) step. However, for example, methanol, ethanol, n-propanol, isopropanol and n-butanol may be used either singly or in any combination thereof. No particular limitation is imposed on a favorable organic solvent usable in Condensation (2) step so far as the solvent does not participate in the reaction. However, examples thereof include ethylene glycol, N-methylpyrrolidone, N,N-dimethyl-acetamide, N,N-dimethylformamide, dimethyl sulfoxide, sulfolane, chlorobenzene, dichlorobenzene, trichlorobenzene and nitrobenzene.

The reaction in Condensation (1) step is conducted in a temperature range of from 0 to 200° C., favorably from 10 to 150° C., more favorably from 20 to 100° C. The reaction in Condensation (2) step is conducted in a temperature range of from 50 to 250° C., favorably from 100 to 230° C., more favorably from 150 to 220° C.

In the case of compounds in which $R_1$ and $R_2$, and $R_1'$ and $R_2'$ in the substituents of the amine derivatives to be reacted are the same substituents, the same amine derivatives may be used, so that the staining compound of the general formula (III) can be obtained through a one-stage condensation step. In this case, the reaction temperature follows the condition of Condensation (2) step.

No particular limitation is imposed on the condensing agent used in the condensation step so far as it does not participate in the reaction. However, the condensing agent may be chosen for use from, for example, magnesium oxide, zinc chloride and aluminum chloride.

The resultant staining compound (III) may be subjected to an ordinary isolation/purification process for organic compounds. For example, a reaction mixture is acidified with hydrochloric acid and subjected to aciding-out, thereby separating solids by filtration, and then subjected to neutralization with sodium hydroxide or the like and concentration, thereby obtaining a crude product. The crude product is further purified by recrystallization with acetone or methanol, column purification using silica gel, or the like. These methods may be used singly or in combination of two or more methods thereof to conduct purification, thereby obtaining the compound with higher purity.

Specific Exemplified Compounds (1) to (122) according to the present invention will be shown below. However, compounds according to the present invention are not limited thereto.

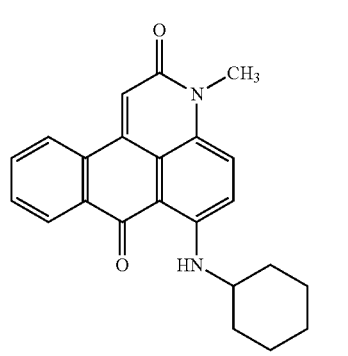
(1)

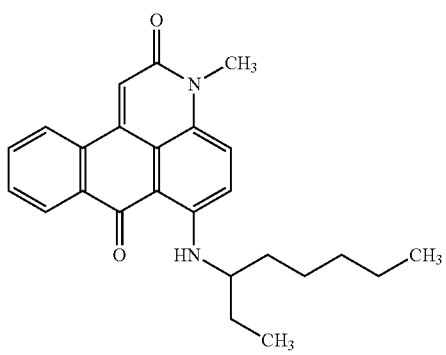
(2)

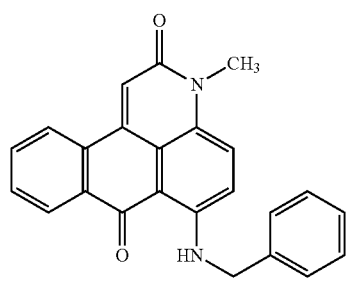
(3)

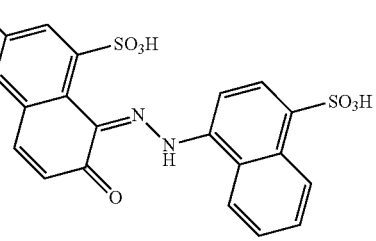
(4)

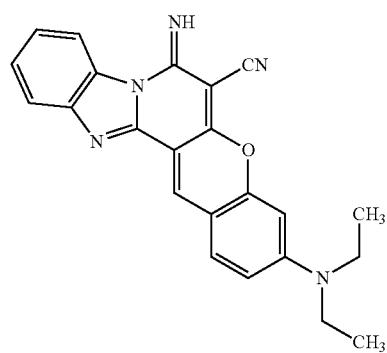
(5)

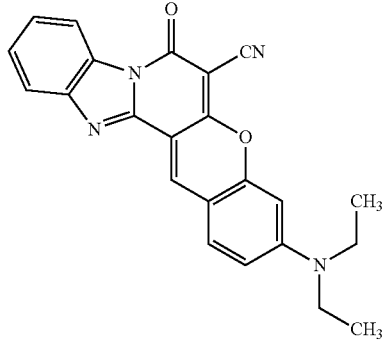
(6)

-continued
(7) 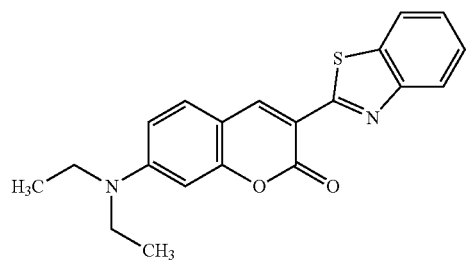
(8) 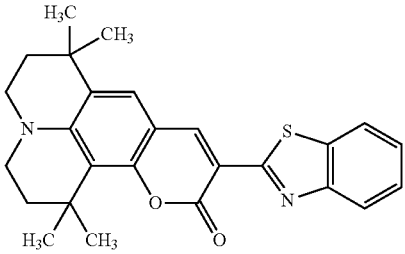
(9) 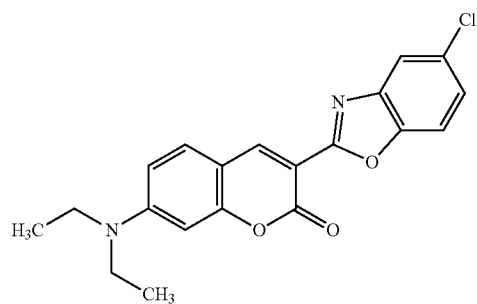
(10) 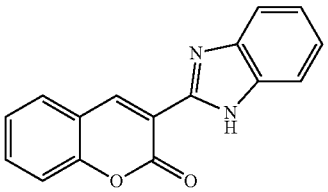
(11) 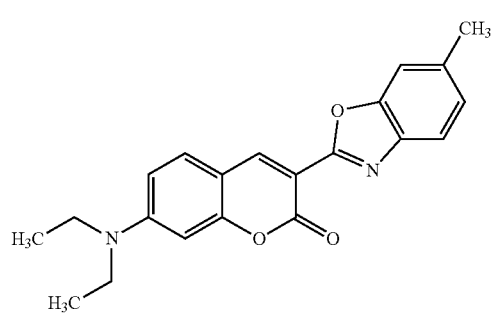
(12)
(13) 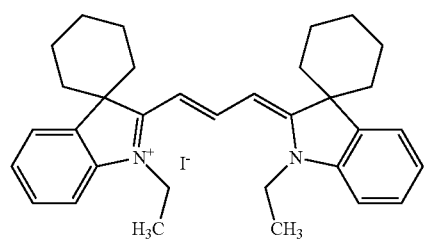
(14) 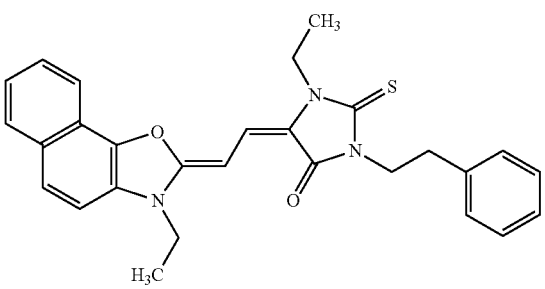
(15)
(16)

-continued
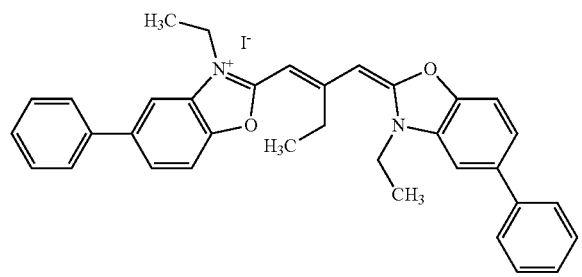 (17)
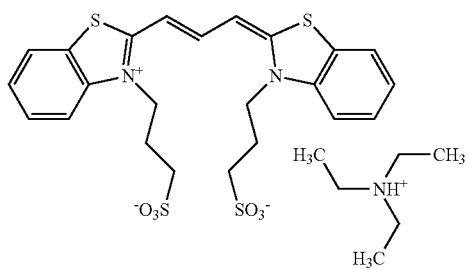 (19)
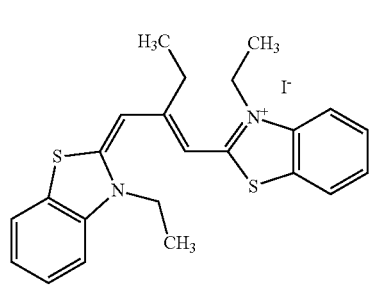 (20)
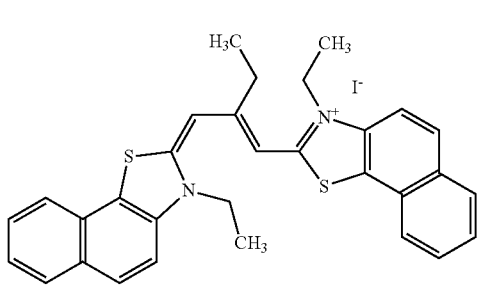 (21)
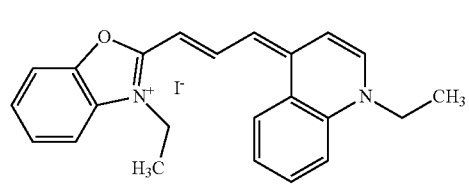 (22)
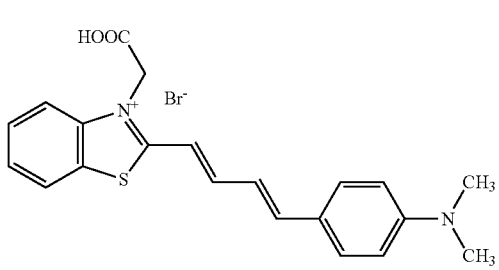 (24)
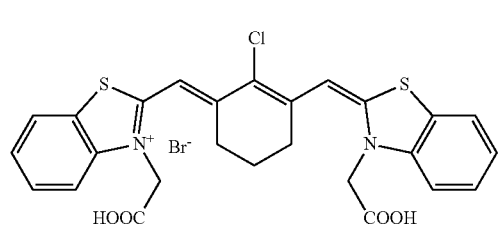 (25)
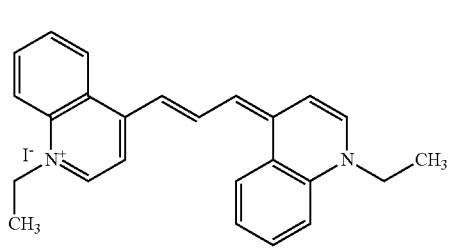 (26)
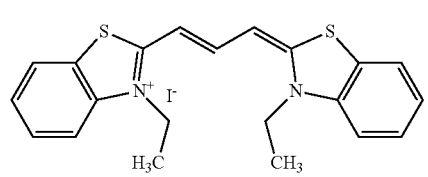 (27)
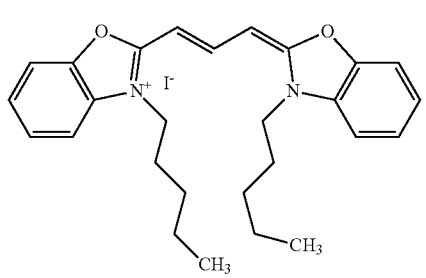 (29)

-continued
(30)
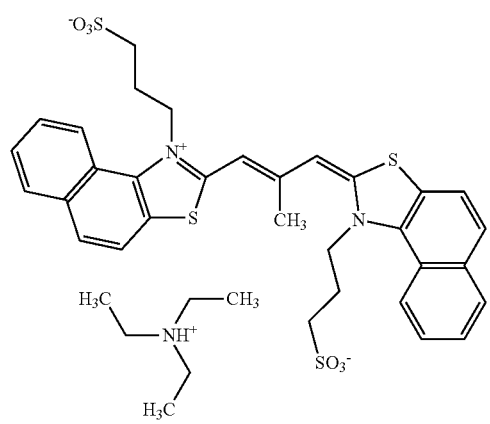
(31)
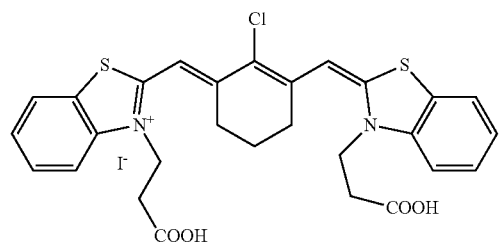
(32)
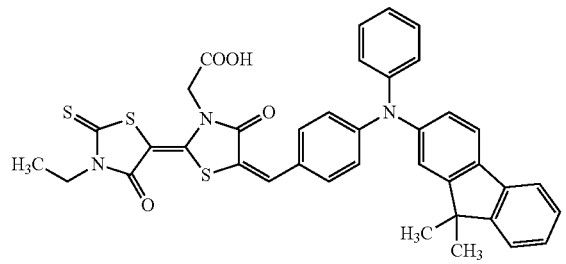
(33)
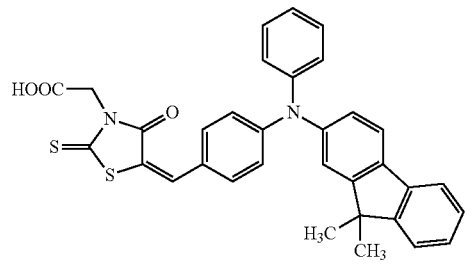
(34)
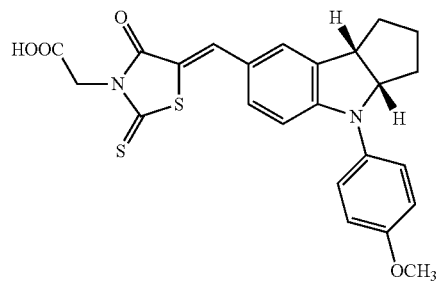
(35)
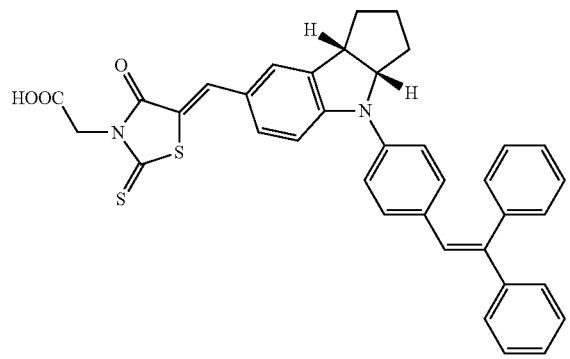
(36)
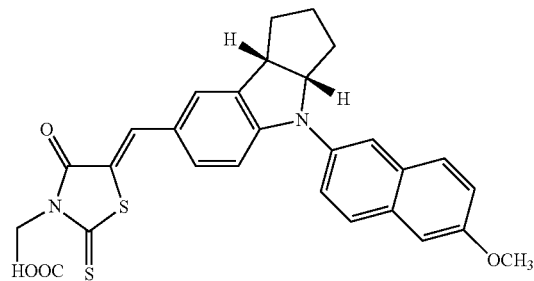
(37)
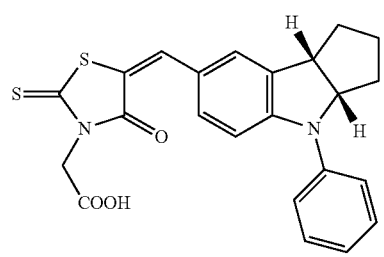

-continued
(38)
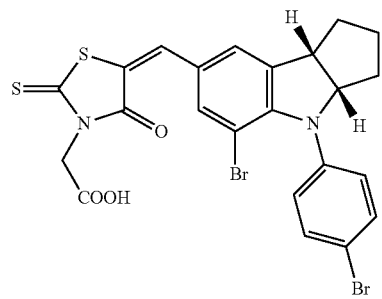
(39)
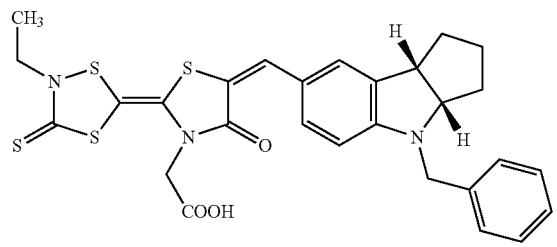
(40)
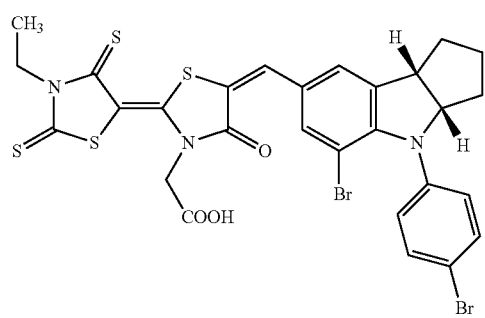
(41)
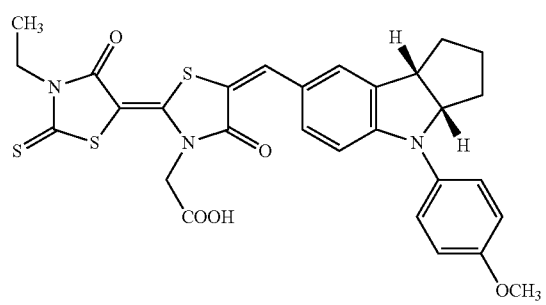
(42)
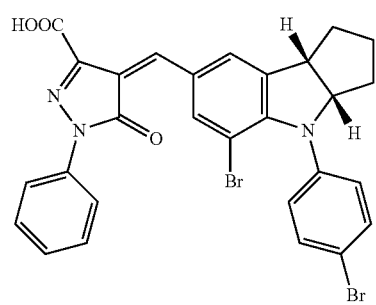
(43)
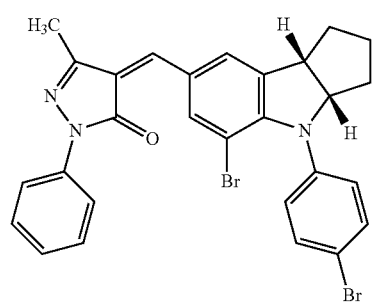
(44)
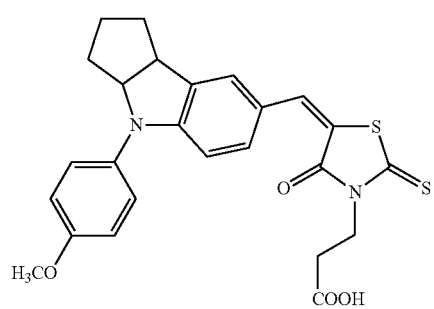
(45)
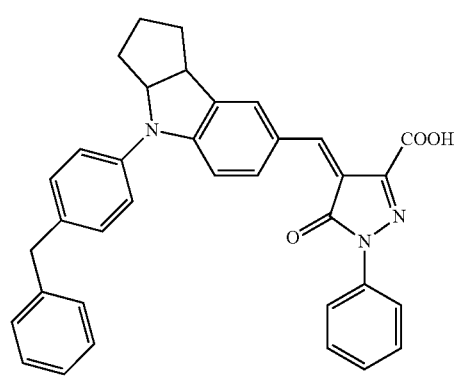

-continued
(46)
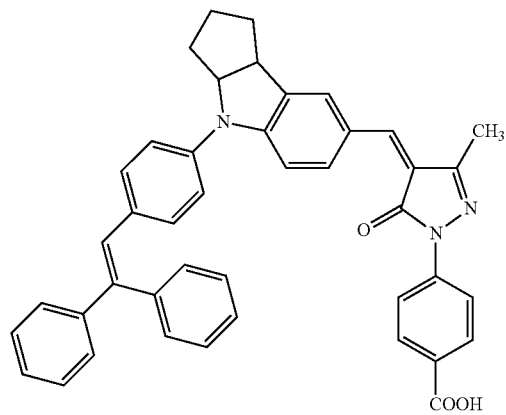
(47)
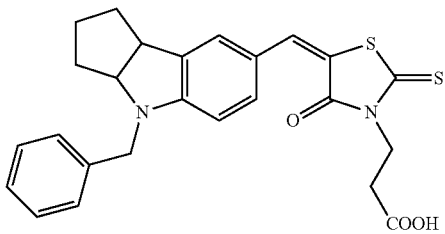
(48)
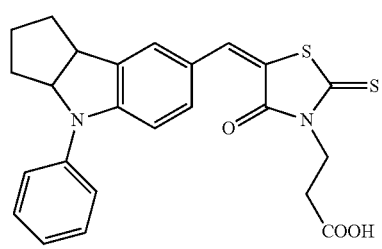
(49)
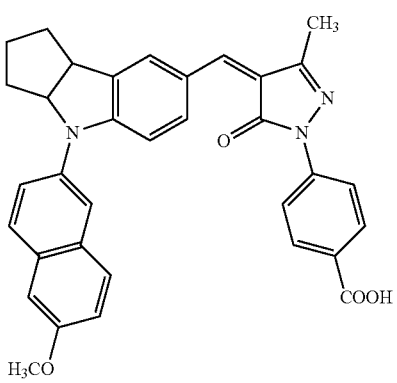
(50)
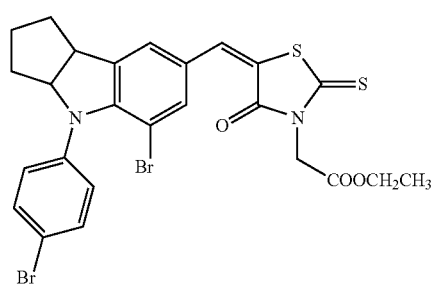
(51)
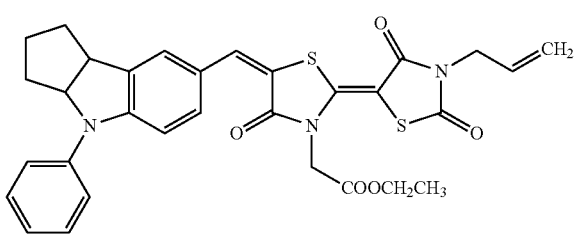
(52)
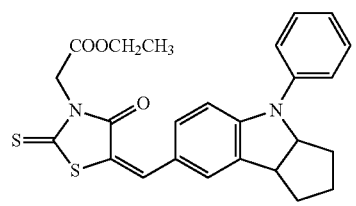
(53)
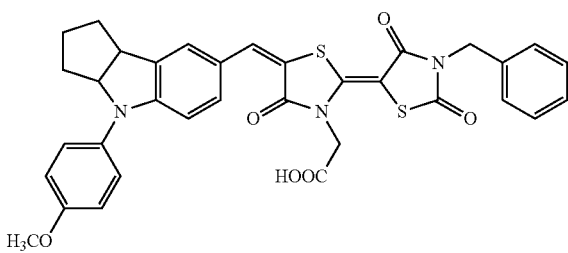

-continued
(54)
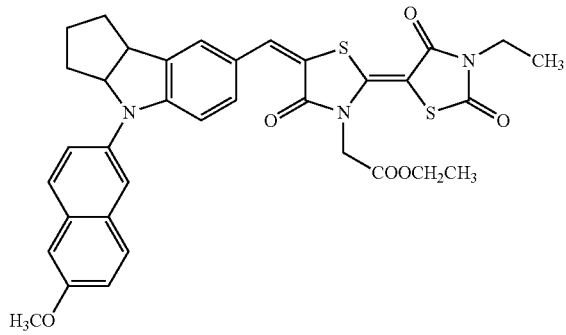
(55)
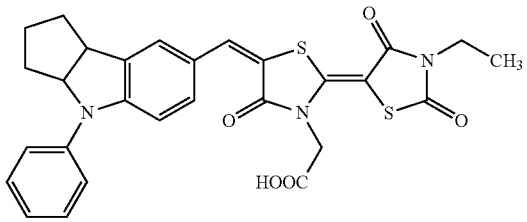
(56)
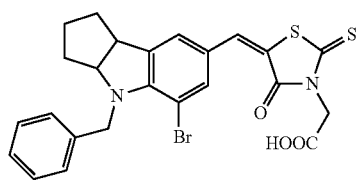
(57)
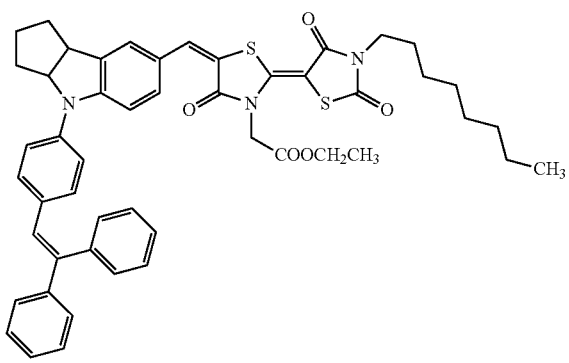
(58)
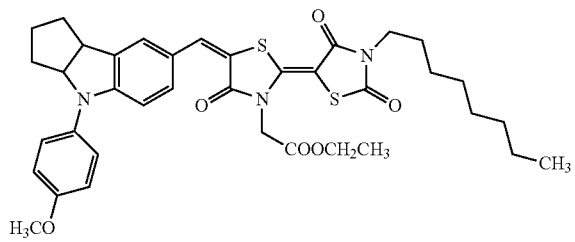
(59)
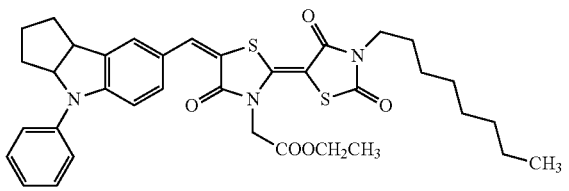
(60)
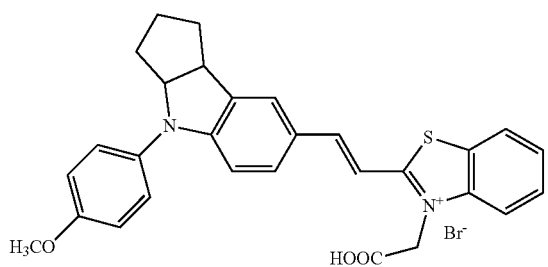
(61)
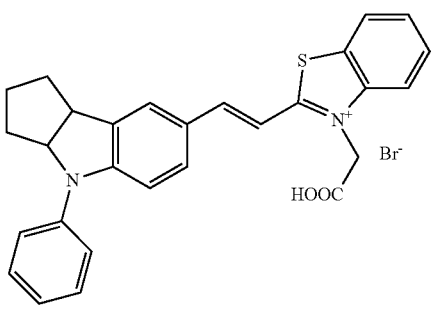
(62)
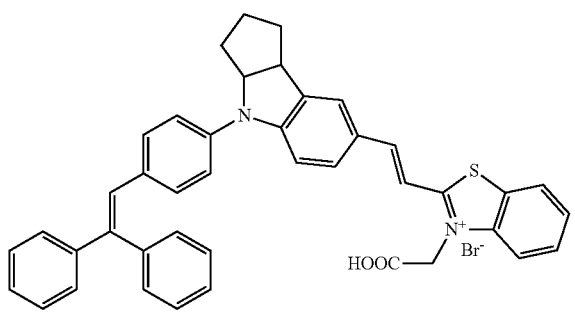
(63)
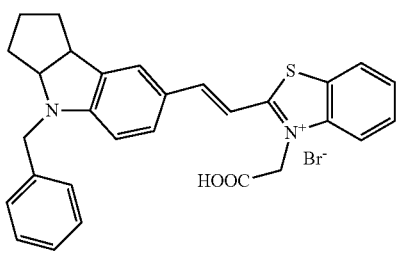

-continued
(64)
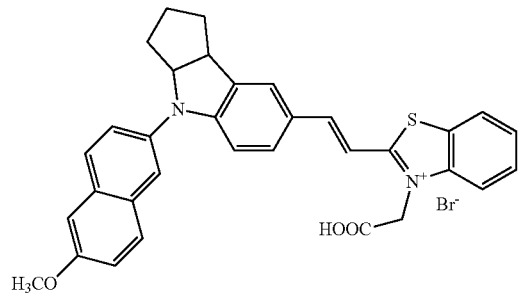
(65)
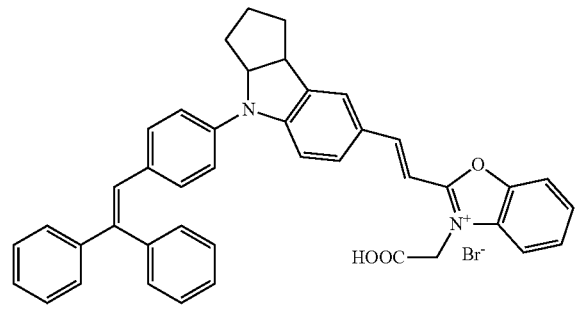
(66)
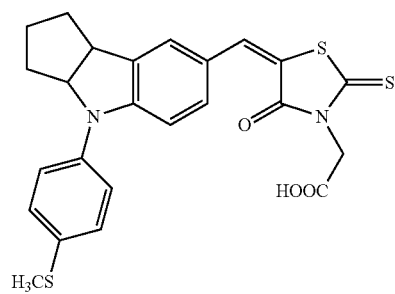
(67)
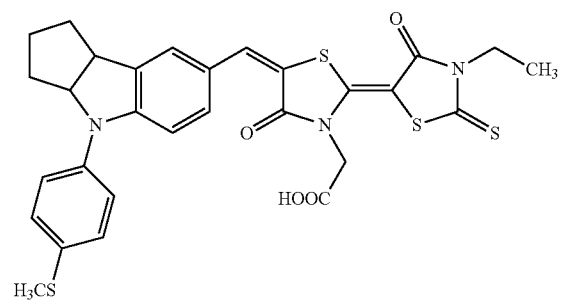
(68)
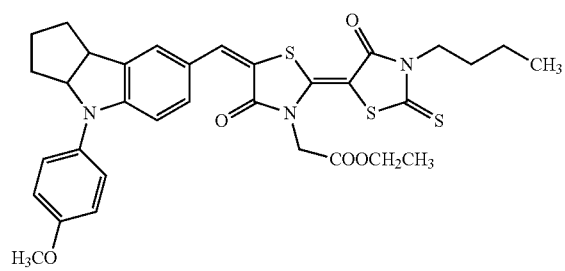
(69)
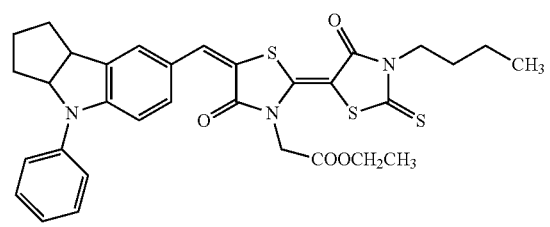
(70)
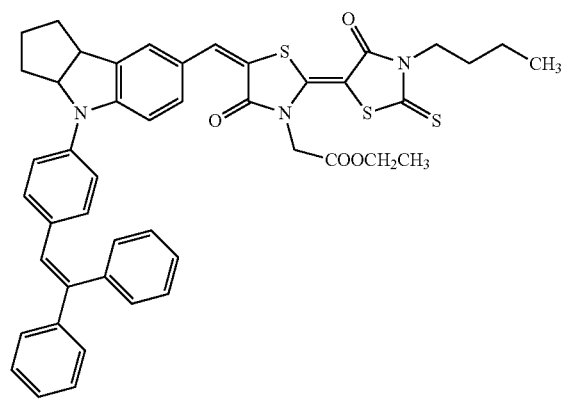
(71)
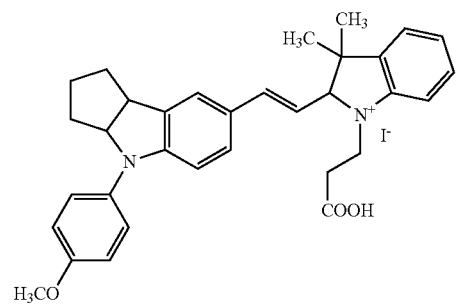

-continued
(72)
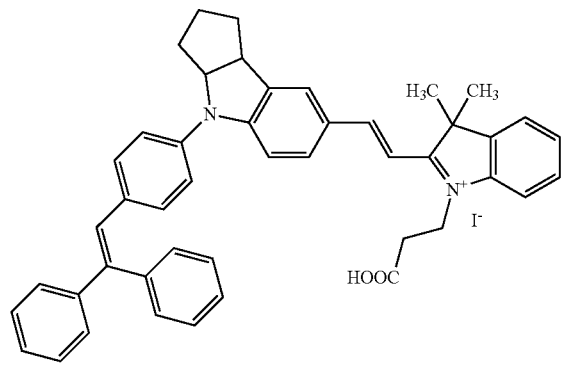
(73)
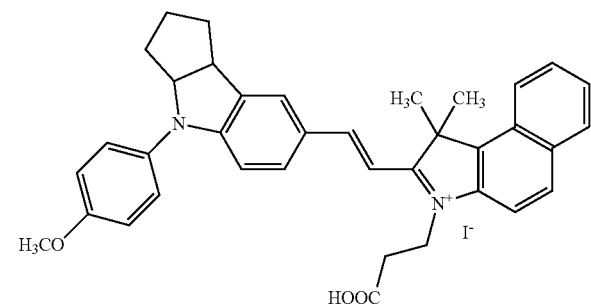
(74)
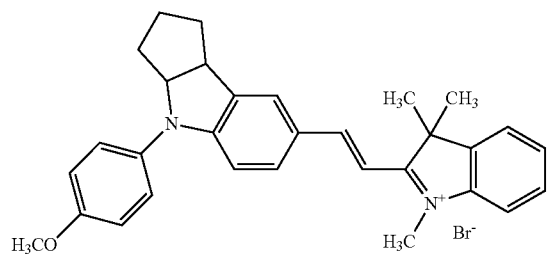
(75)
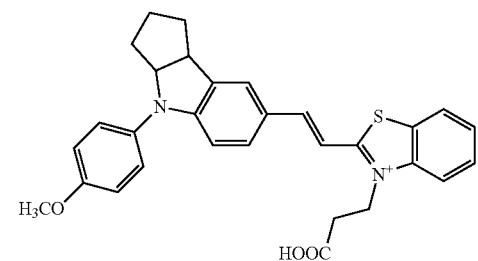
(76)
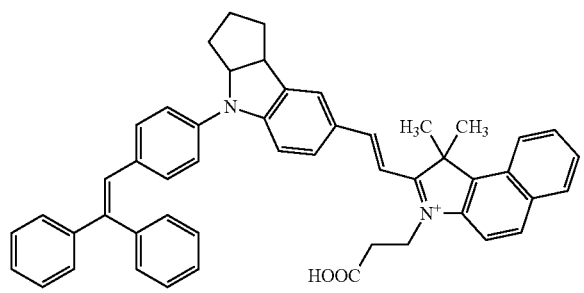
(77)
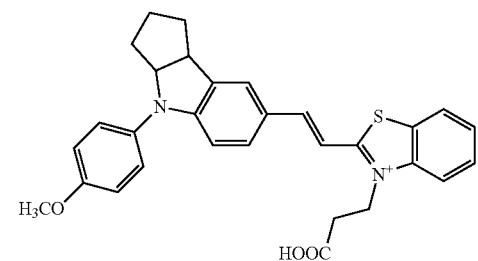
(78)
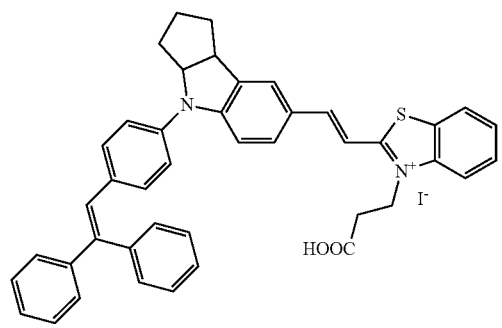
(79)
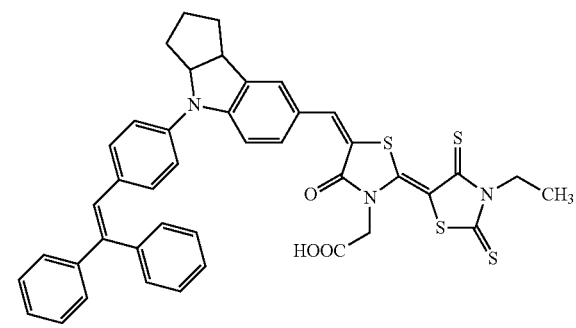

-continued
(80)
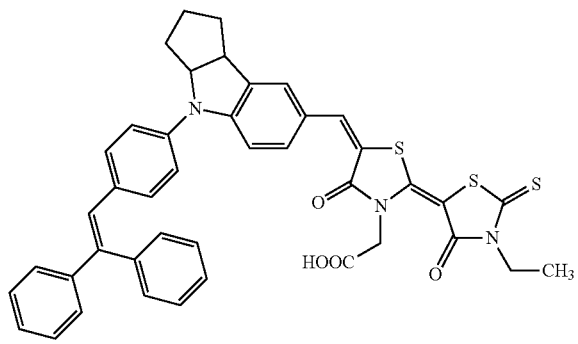
(81)
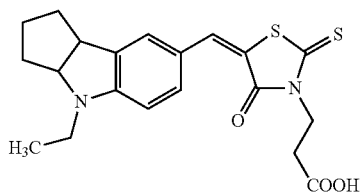
(82)
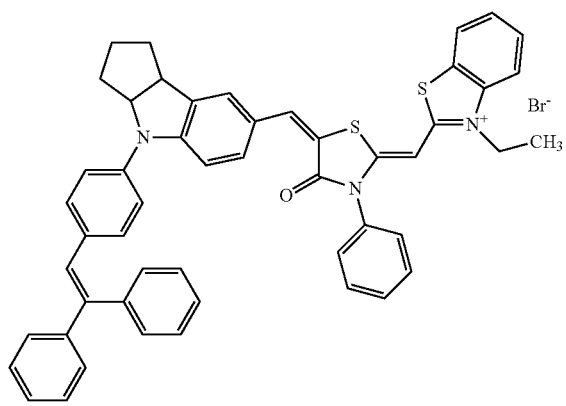
(83)
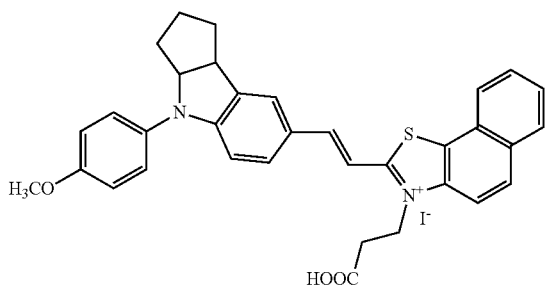
(84)
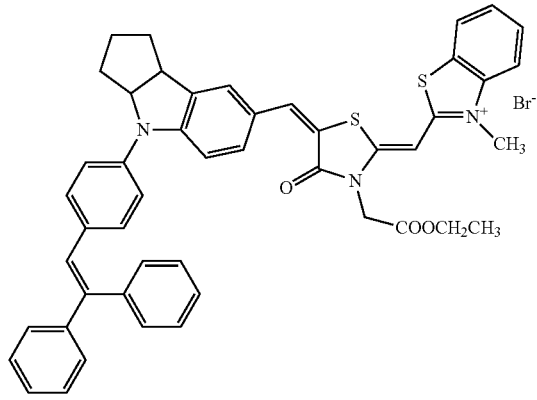
(85)
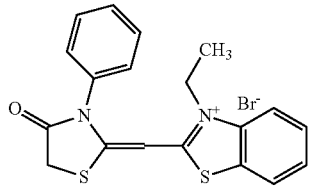
(86)
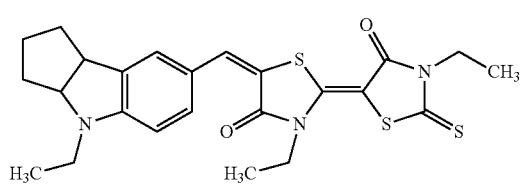
(87)
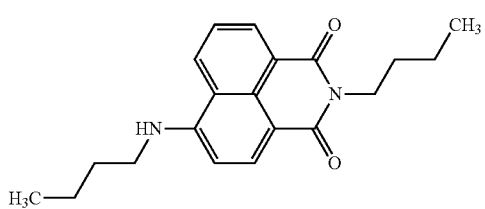

-continued
(88)
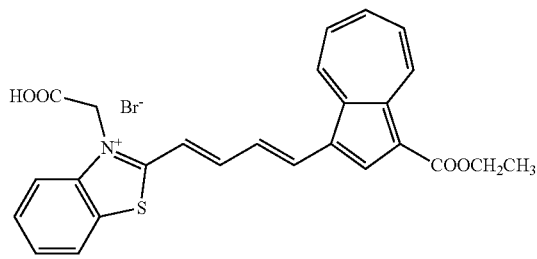
(89)
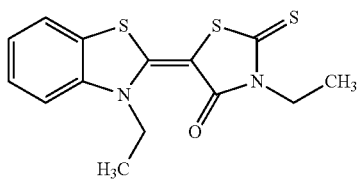
(90)
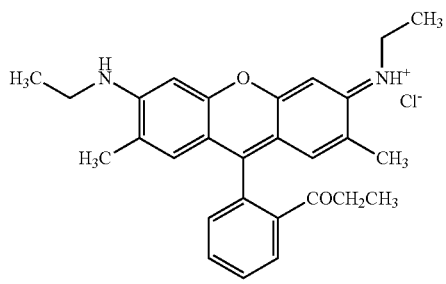
(91)
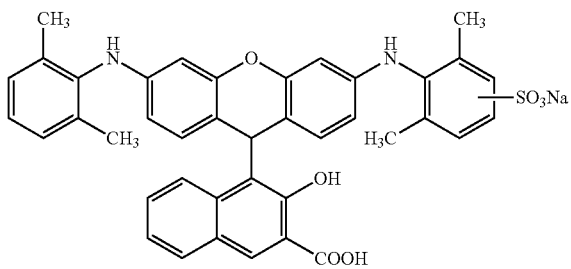
(92)
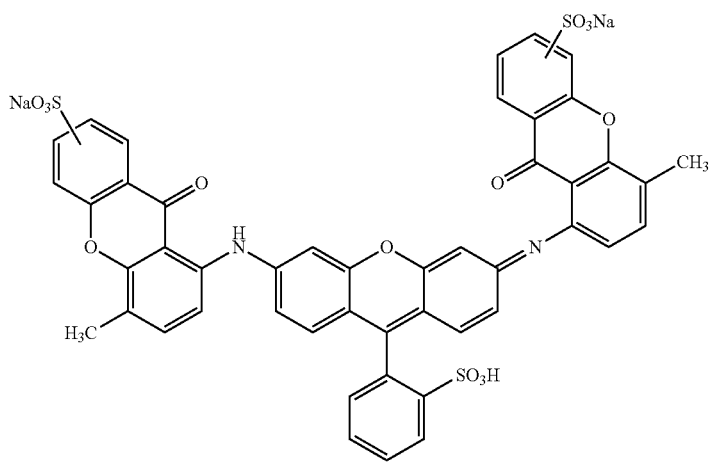
(93)
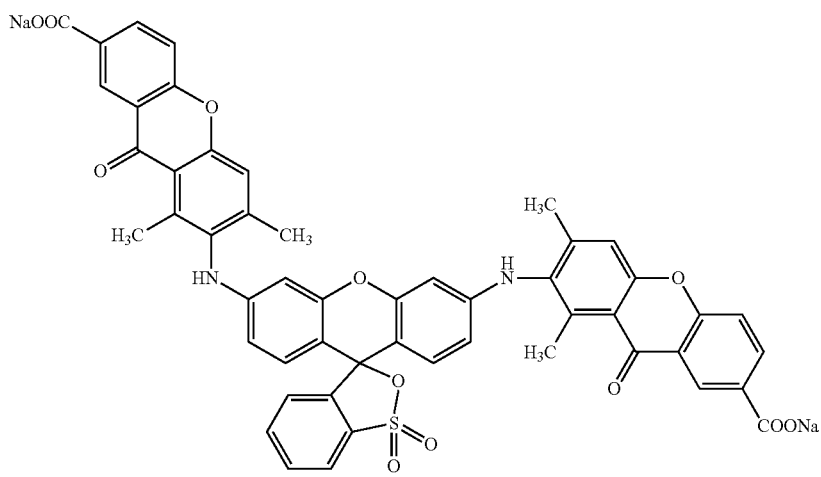

-continued
(94)
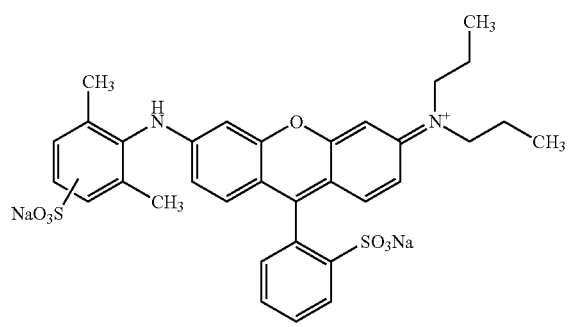
(95)
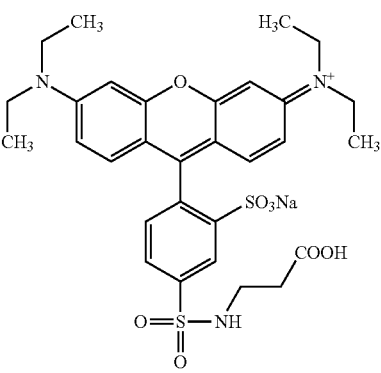
(96)
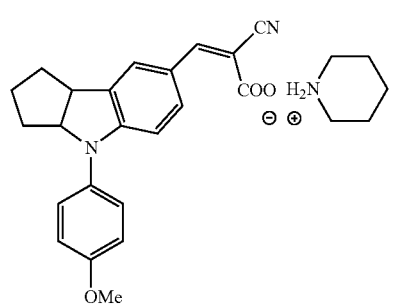
(97)
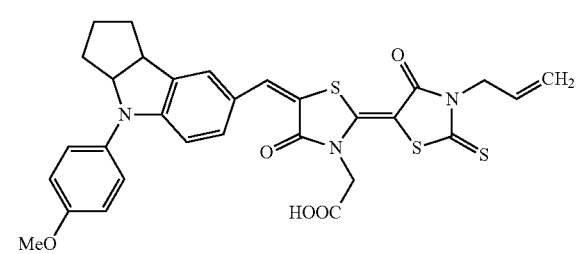
(98)
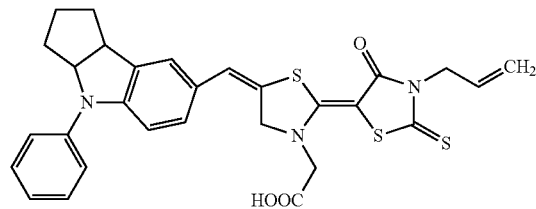
(99)
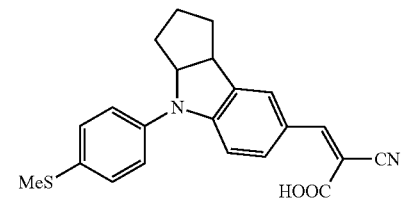
(100)
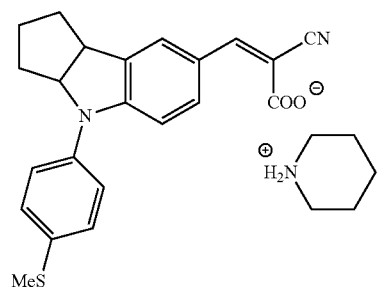
(101)
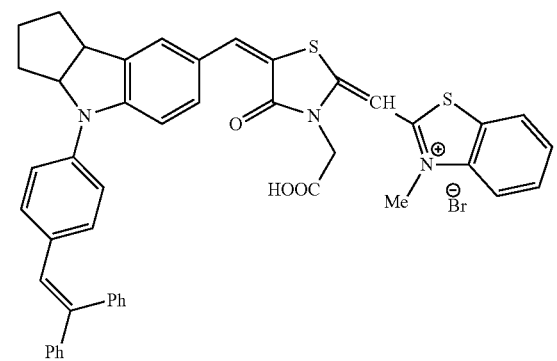
(102)
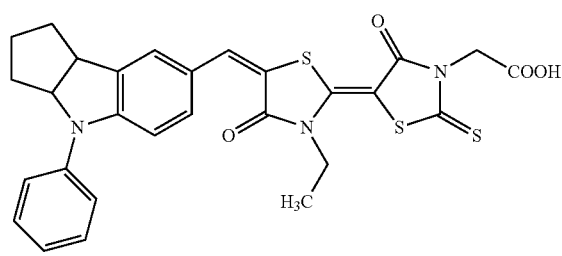
(103)
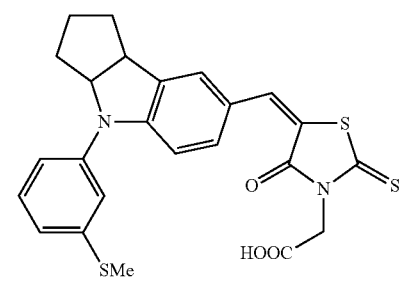

-continued
(104)
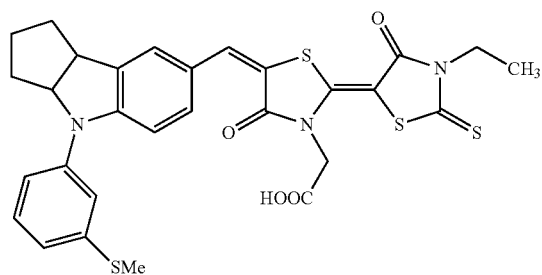
(105)
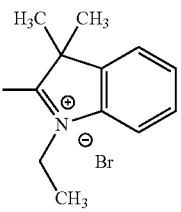
(106)
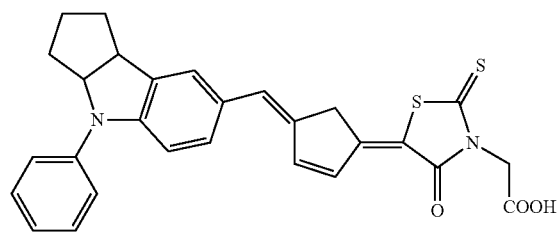
(107)
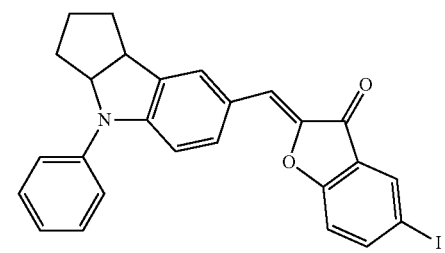
(108)
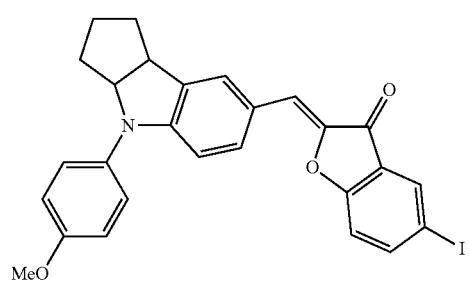
(109)
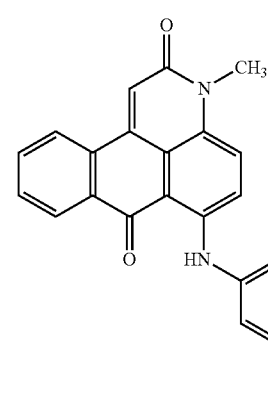
(110)
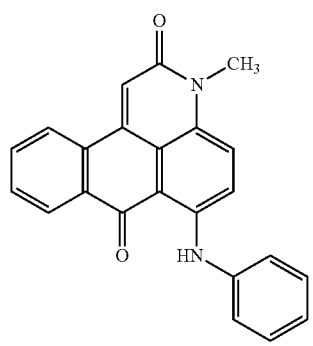
(111)
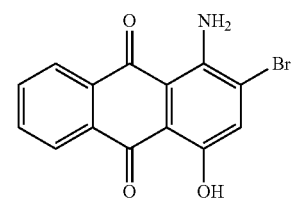
(112)
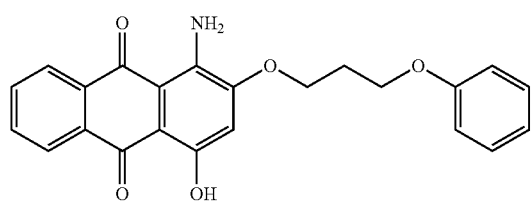
(113)
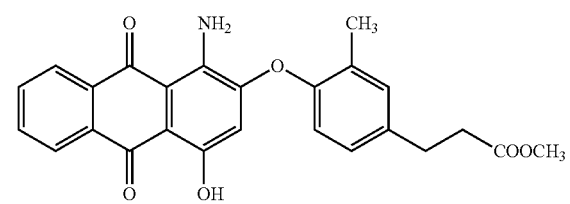

(114) 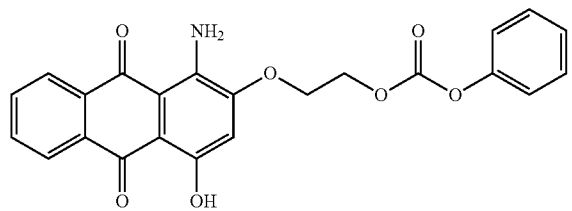
(115) 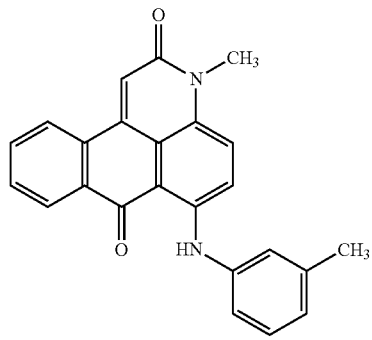
(116) 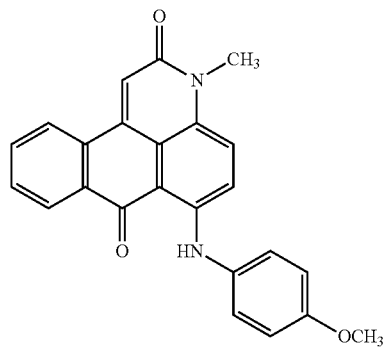
(117) 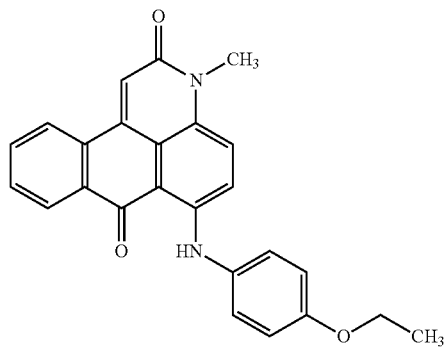
(118) 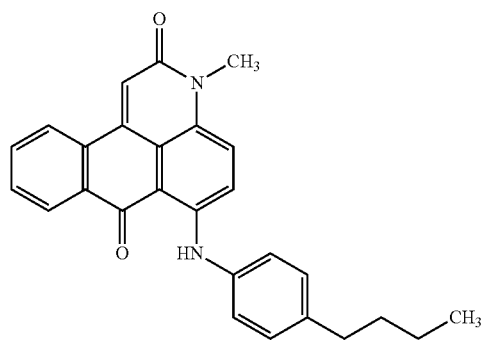
(119) 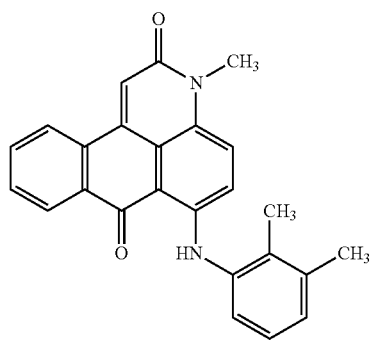
(120) 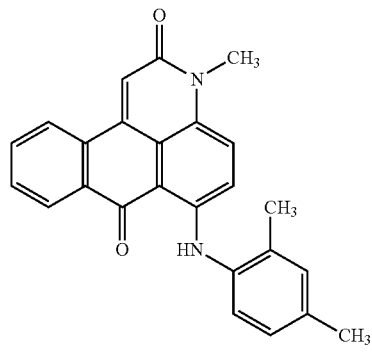
(121) 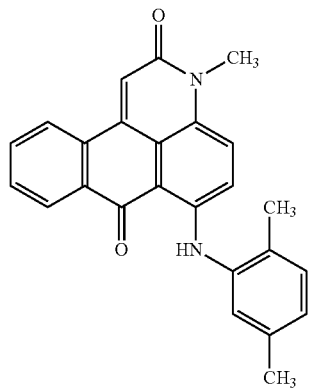

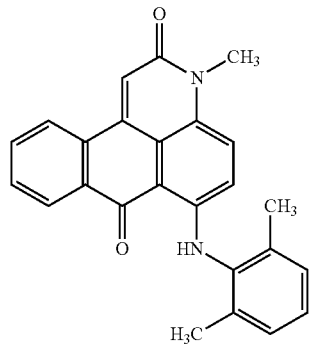

(122)

<Radiation Labeling>

The labeling composition for the intraocular tissue according to the present invention may also be used as a probe labeled with a radioactive nuclide.

No particular limitation is imposed on the kind of the radioactive nuclide used in labeling, and it may be suitably selected according to the mode of use.

The labeling composition for the intraocular tissue labeled with the radioactive nuclide may be used in imaging by, for example, autoradiography, positron emission tomography (PET) using a positron emission nuclide, or single photon emission computed tomography (SPECT) using various kinds of gamma-ray emission nuclides. Detection may also be made by magnetic resonance imaging (MRI) making good use of an MR signal derived from a fluorine atomic nucleus, or $^{13}C$. In addition, imaging may also be conducted by a Compton camera (GREI) capable of coincidently imaging a plurality of molecules as a next-generation molecular imaging apparatus. It may also be possible to quantify a probe for a retinal tissue using, for example, a liquid scintillation counter, X-ray film or imaging plate.

A labeling composition for the intraocular tissue labeled with a radioactive isotope such as $^{14}C$ permits measuring a concentration in blood (or urine or feces) by an accelerator mass spectrometry (AMS) or the like to obtain pharmacokinetic information (area under the blood concentration-time curve (AUC), blood concentration half-life period ($T_{1/2}$), maximum drug concentration ($C_{max}$), maximum drug concentration time ($T_{max}$), distribution volume, first-pass effect, biological utilization factor, excretion rates in feces and urine, etc.) of the parent compound and metabolite of the substance labeled.

No particular limitation is imposed on the radioactive nuclide, and it may be suitably selected according to the mode of use.

Specifically, in the case of measurement by PET, a positron emission nuclide of, for example, $^{11}C$, $^{14}C$, $^{13}N$, $^{15}O$, $^{18}F$, $^{19}F$, $^{62}Cu$, $^{68}Ga$ or $^{78}Br$ may be used. $^{11}C$, $^{13}N$, $^{15}O$ or $^{18}F$ is favorable, with $^{11}C$ or $^{18}F$ being particularly favorable.

In the case of measurement by SPECT, a γ-ray emission nuclide of, for example, $^{99m}Tc$, $^{111}In$, $^{67}Ga$, $^{201}Tl$, $^{123}I$ or $^{133}Xe$ may be used. $^{99m}Tc$ or $^{123}I$ is favorable.

In the case of measuring another animal than human, a radioactive nuclide longer in half-life period, such as, for example, $^{125}I$ may be used.

In the case of measurement by GREI, for example, $^{131}I$, $^{85}Sr$ or $^{65}Zn$ may be used.

The radioactive nuclide may be either contained in or bonded to the compound represented by any one of the general formulae (I) to (XVIV), (VIII'), and (XVII').

No particular limitation is imposed on the labeling method with the radioactive nuclide, and a generally used method may be used. At least part of the elements forming the compound represented by any one of the general formulae (I) to (XVIV), (VIII'), and (XVII') may be substituted by the radioactive nuclide or bonded thereto.

When the compound represented by any one of the general formulae (I) to (XVIV), (VIII'), and (XVII') is labeled with the radioactive nuclide, the compound favorably has a radioactivity of about 1 to 100 µCi per mM.

At this time, no particular limitation is imposed on the dose of the labeling composition for the intraocular tissue used, and it may be suitably selected according to the kind of the compound and the kind of the radioactive nuclide used in labeling.

<Preparation of Labeling Composition for Intraocular Tissue>

No particular limitation is imposed on the concentration of the compound contained in the labeling composition for the intraocular tissue according to the present invention so far as the intraocular tissue can be detected. However, the concentration may be suitably adjusted according to the target site and the compound used. The compound is used at a concentration of generally 0.001 ng/mL or more and 100 µg/mL or less, favorably 0.001 ng/mL or more and 10 µg/mL or less, more favorably 0.001 ng/mL or more and 5 µm/mL or less.

The labeling composition for the intraocular tissue according to the present invention is used by dissolving at least one of the staining compound s represented by any one of the general formulae (I) to (XVIV), (VIII'), and (XVII') in a proper solvent. No particular limitation is imposed on the solvent so far as it does not affect a living body. However, an aqueous liquid high in affinity for the living body is favorable. Examples thereof include water; physiological saline; buffer solutions such as phosphate buffer solution (PBS) and Tris; alcoholic solvents such as methanol, ethanol, isopropanol, butanol, ethylene glycol and glycerol; organic solvents such as N,N-dimethyl sulfoxide (hereinafter abbreviated as DMSO) and N,N-dimethylformamide (hereinafter abbreviated as DMF); cell culture media such as D-MEM and HBSS; and infusions such as lactate Ringer solution. It is particularly favorable to contain at least 50% of water. These solvents may also be used in combination of two or more thereof.

No particular limitation is imposed on a preparation method of the labeling composition for the intraocular tissue according to the present invention. For example, the composition may be prepared by diluting a thick solution of the compound dissolved in such a solvent as described above. In the case where the water solubility of the compound is low, the compound may be dissolved in a proper solvent and then diluted with purified water to use it. The proper solvent is particularly favorably methanol, ethanol or DMSO.

If it is necessary to control the salt concentration or pH to be suitable for the living body, additives may be added to the labeling composition for the intraocular tissue according to the present invention either singly or in combination of two or more thereof.

No particular limitation is imposed on the additives used in the present invention so far as they do not affect the labeling composition for the intraocular tissue. However, examples thereof include humectants, surface tension adjustors, thickeners, salts such as sodium chloride, various kinds of pH adjustors, pH buffers, preservatives, antibacterial agents, sweetening agents, and perfume bases.

The pH adjustors favorably adjust the pH to be 5 to 9, and no particular limitation is imposed on the pH adjustors. However, examples thereof include hydrochloric acid, acetic acid, phosphoric acid, citric acid, malic acid, sodium hydroxide and sodium hydrogencarbonate.

<Testing Method>

The compound contained in the labeling composition for the intraocular tissue in the present invention is favorably a compound with a maximum luminance ratio (La/Lb) of 3 or more when the following testing method is performed. Details of the testing method for selecting the compound used in the present invention are described below.

An aqueous solution of a test compound is prepared to give a concentration of 1 μg/mL, and three Zebrafish 7-day-old embryos are exposed to the aqueous solution for one hour. Thereafter, the embryos are washed twice with purified water and immobilized with a 4% paraformaldehyde solution to provide immobilized sections a1 to a3 of one eyeball of the respective Zebrafishes. On the other hand, three untreated Zebrafish 7-day-old embryos are immobilized with a 4% paraformaldehyde solution to provide immobilized sections b1 to b3 of one eyeballs of the respective Zebrafishes. In this testing method, an immobilized section containing the entire layer structures of at least vitreous body and retina is used.

The immobilized sections a1 to a3 are used to adjust the magnification of an observation apparatus to a magnification capable of observing a retinal section of each eyeball, thereby setting the excitation wavelength and the fluorescence wavelength to those at which the fluorescence intensity in the retinal tissue becomes maximum. The magnification capable of observing the retinal section is not required to be strictly adjusted so far as the layer structures of the vitreous body and retina can be identified. However, the magnification is favorably such that the whole tissue section of the eye is included. Specifically, the structure of the retinal tissue can be visualized by setting the magnification to from 10 times to 400 times, favorably from 40 times to 200 times. On the other hand, the average value of maximum luminance values in arbitrarily-sized retinal regions between the retinal pigment epithelium and vitreous body of the immobilized sections b1 to b3 is regarded as Lb to set the intensity of excitation light and photographic sensitivity such that the value Lb falls within a range of from 2 to 6.

Under the thus-set observation conditions, the average value of maximum luminance values in arbitrarily-sized retinal regions between the retinal pigment epithelium and vitreous body of the immobilized sections a1 to a3 is regarded as La to calculate the value La/Lb.

No particular limitation is imposed on the strain of Zebrafishes used in this testing method. However, for example, a wild type having no genetic variation, or a strain having no genetic variation relating to eyes in particular is favorably used. Specifically, RIKEN WT (RW), AB strain or TU strain is favorably used.

The exposure to the solution of the test compound can be conducted by putting a Zebrafish 7-day-old embryo in an arbitrary well in, for example, a 24-well plate together with breeding water, and taking the breeding water out of the well to be replaced by the solution of the test compound, thereby bringing the solution into contact with the embryo. A method of adding a proper amount of a thick solution of the test compound to a Zebrafish embryo put in a well together with distilled water in such a manner that the final concentration is 1 μg/mL may also be used.

In general, the compound migrating to the intraocular tissue without damaging the ocular tissue or the nerve tissue linking to the ocular tissue can label the intraocular tissue by exposing the Zebrafish 7-day-old embryo to the solution of the test compound for 1 hour. No particular limitation is imposed on the observation of the intraocular tissue. However, for example, observation can be made by observing an immobilized section of an ocular tissue of Zebrafish, which has been exposed to the solution of the test compound.

No particular limitation is imposed on preparation of the immobilized section of an eyeball of Zebrafish. However, for example, the section can be prepared by embedding Zebrafish in a low-temperature fused agarose gel and slicing it by a commercially available microtome.

No particular limitation is imposed on the commercially available microtome so far as a section can be prepared. However, examples thereof include Vibratome and Linear Slicer. In particular, Linear Slicer is favorably used because a section is prepared more satisfactorily. The immobilized section prepared by such a microtome is placed on a slide glass to observe it.

It may also be possible to embed Zebrafish in a compound for a frozen tissue section, rapidly freeze it with liquid nitrogen, and then prepare a section by a cryostat microtome. No particular limitation is imposed on the cryostat microtome. However, a commercially available Cryostat may be favorably used. The frozen section prepared in such a manner is placed on a slide glass and then dried to observe it.

No particular limitation is imposed on the thickness of a section upon preparation of the section so far as the thickness is fixed upon testing. However, for example, a thickness of 5 μm or more is favorable because its morphology is easily kept upon its transfer to a slide glass.

The control to the excitation wavelength and fluorescence wavelength at which the fluorescence intensity in the retinal tissue becomes maximum can be made by changing the set of fluorescent light filters in such a manner that when a section sample exposed to an aqueous solution containing a test compound is observed, the sample is irradiated with excitation light of an arbitrary wavelength, and fluorescence of a wavelength longer by at least 10 nm or more, favorably 20 nm or more than the excitation wavelength is detected, the excitation light is scarcely visible and the fluorescence intensity becomes highest.

For the measurement of the maximum luminance value in the region including the retinal tissue, it is necessary to set the excitation wavelength and fluorescence wavelength of the observation apparatus according to the test compound used.

No particular limitation is imposed on the observation apparatus used so far as it permits fluorescence observation. However, examples thereof include a stereoscopic fluorescence microscope, a fluorescence microscope and a confocal laser-scanning fluorescence microscope.

In this testing method, an image containing the retinal region of the immobilized section b is obtained, and a maximum luminance value in an arbitrary region of the image thus obtained is measured.

The maximum luminance value is measured by means of a software or the like. It is favorable to measure the value by converting the image to a gray scale. No particular limitation is imposed on the software used in the measurement of the maximum luminance value so far as the maximum luminance value in the arbitrary region is determined. However, examples thereof may include NIH Image, Scion Image and Image J.

Such software is used to control the intensity of excitation light and photographic sensitivity in such a manner that the maximum luminance values of the immobilized sections b1 to b3 fall within a range of from 2 to 6, thereby obtaining the average value Lb of the maximum luminance values of the immobilized sections b1 to b3.

An image containing the retinal region of each of the immobilized sections a1 to a3 is then obtained under the conditions set above, whereby the average value La of the maximum luminance values of the immobilized sections a1 to a3 can be obtained in the same manner as described above.

The compound contained in the labeling composition for intraocular tissue according to the present invention is favorably such that the ratio (La/Lb) of La to Lb obtained in the above-described testing method is 3 or more. The compound that the ratio La/Lb is 3 or more can clearly label the intraocular tissue without damaging the ocular tissue or the nerve tissue linking to the ocular tissue. The ratio La/Lb is favorably 5 or more, more favorably 10 or more, because the intraocular tissue is stained in a clearly distinguishable state even when the concentration of the compound is low.

<Labeling Method>

The labeling method for the intraocular tissue according to the present invention can be conducted by using the labeling composition for the intraocular tissue containing at least one of the staining compound s represented by any one of the general formulae (I) to (XVIV), (VIII'), and (XVII'). The method for labeling the intraocular tissue of a living individual is to label with the labeling composition without causing a surgical damage such as incision of an ocular tissue or needling into the ocular tissue or a nerve tissue linking to the ocular tissue.

No particular limitation is imposed on the labeling method without the surgical damage. However, examples thereof include a method of exposing a part or the whole of a living individual to the labeling composition for the intraocular tissue, a method by oral contact, a method by pneumonic contact, a method by nasal contact, a method by transgastrointestinal contact, a method by transmucosal contact, a method by transhumoral contact, a method by hypoglossal contact, a method by intravascular contact such as intravenous or intra-arterial contact, a method by intra-abdominal contact, an intra-abdominal, subcutaneous, intracutaneous, intravesical or endotracheal (intrabronchial) injection method, and a method by contact with the interior of a living body by a device such as spraying or coating.

The labeling composition for the intraocular tissue according to the present invention may also be injected directly into an eye to label the intraocular tissue. No particular limitation is imposed on the method of injecting directly into the eye. However, for example, the method is performed by making a hole by sclerotomy, filling a posterior portion of a vitreous body with air and then injecting several drops, generally 1 mL or less, of the labeling composition for the intraocular tissue according to the present invention into the eye.

<Observing Method>

The observing method of the present invention uses the labeling composition for the intraocular tissue according to the present invention. The measuring and detecting methods thereof are performed by methods publicly known by a person with ordinary skill in the art.

No particular limitation is imposed on the observing method used in the present invention so far as the intraocular tissue is not affected. The method is a method for capturing the condition and change of a living sample as images. Examples thereof include visible light observation, near-infrared light observation and infrared light observation performed by irradiating an ocular tissue with visible light, near-infrared light and infrared light, respectively, and observing the ocular tissue by a camera or CCD; laser microscope observation; fluorescence observation, fluorescence microscope observation, fluorescence endoscope observation, confocal microscope observation, multiple photon-excited fluorescence microscope observation, and narrow-band light observation performed by irradiating a living sample with excitation light from an excitation light source like a fluorescence endoscope to observe fluorescence of the living sample causing emission; optical coherence tomographic (OCT) observation; and observation by a soft X-ray microscope.

No particular limitation is imposed on the wavelength for excitation used in the present invention. However, it varies according to the staining compound represented by any one of the general formulae (I) to (XVIV), (VIII'), and (XVII'), and no particular limitation is imposed thereon so far as the staining compound represented by any one of the general formulae (I) to (XVIV), (VIII'), and (XVII') efficiently emits fluorescence. The wavelength is generally from 200 to 1,010 nm, favorably from 400 to 900 nm, more favorably from 480 to 800 nm. In the case of using light in a near-infrared region, a wavelength of generally from 600 to 1,000 nm, favorably from 680 to 900 nm, is used.

No particular limitation is imposed on the light source for fluorescence excitation used in the present invention. However, various kinds of laser beam sources may be used. Examples thereof include dye lasers, semiconductor lasers, ion lasers, fiber lasers, halogen lamps, xenon lamps and tungsten lamps. Various kinds of optical filters may be used to obtain a favorable wavelength for excitation or to detect fluorescence alone.

When an intraocular tissue is imaged in a state of causing emission in the interior of an ocular tissue by irradiating a living individual with excitation light in the above-described manner, an emitting site can be easily detected. The intraocular tissue can be observed in more detail by combining a bright field image obtained by irradiation of visible light with a fluorescent image obtained by irradiation of excitation light by an image processing unit.

<Screening Method>

According to the labeling composition for the intraocular tissue according to the present invention, general characteristics with respect to staining of an intraocular tissue can be screened in a living state, i.e., in vivo, by using a living individual, for example, Zebrafish that is a small bony fish. In addition, since Zebrafish that is a living individual is used, the safety of the labeling composition for the intraocular tissue may also be screened at the same time.

Zebrafish has been acknowledged as the third model animal following mouse and rat in the United States and Britain in recent years, and it has been found that compared with human the whole genome sequence thereof has 80% homology, the number of genes is also almost the same, and the geneses and structures of the main organs and tissues are also well similar. The Zebrafish is characterized in that the processes of differentiating from a fertilized ovum to form respective parts (viscera and organs such as heart, liver, kidney and alimentary canal) can be observed through a transparent body, so that it is particularly favorable to use Zebrafish in screening as a model animal.

As a specific example, is mentioned such a screening method that the labeling composition for the intraocular tissue is brought into contact with Zebrafish to observe an influence of the labeling composition for the intraocular tissue on Zebrafish.

No particular limitation is imposed on the method for bringing Zebrafish into contact. However, examples thereof include a method of administering the labeling composition for the intraocular tissue into breeding water in the case where the labeling composition for the intraocular tissue is water-soluble, and include, in the case where the labeling composition for the intraocular tissue is water-insoluble, a method of dispersing the labeling composition for the intraocular tissue in breeding water by itself, a method of administering the composition together with a trace quantity of a surfactant or DMSO, a method of mixing the composition with a feed for Zebrafish to orally administering it, and a method of parenterally administering the composition by injection or the like. The method of administering the labeling composition for the intraocular tissue into breeding water is favorable because of its easiness. Thus, the staining compound represented by any one of the general formulae (I) to (XVIV), (VIII'), and (XVII') is desirably water-soluble, and a carboxyl group or sulfonic is desirably contained in the compound.

One or more labeling compositions for the intraocular tissue according to the present invention can be utilized as active agents to conduct in vivo screening for influence on a living body, such as effects, side effects or safety of a chemical substance in an intraocular tissue, using a living individual, for example, Zebrafish. The labeling compositions for the intraocular tissue can be selected as needed according to target sites, objects, inspection methods and/or the like. In addition, applied developments such as high-precision diagnoses of diseases and development of curing methods are expected from the staining ability of the labeling composition for the intraocular tissue, and so this composition may be used as a diagnostic composition.

The chemical substance means a generic name of a compound having chemical action and is not particularly limited. However, examples thereof include pharmaceuticals, organic compounds, curing medicines, investigational drugs, agricultural chemicals, cosmetics, environmental pollutants and endocrine disruptors.

Zebrafish is not limited to wild type Zebrafish, and Zebrafishes of various disease type models may be used according to the object of screening. In the case of using a disease type model, the effects of a proposed new medicine compound can be found by observation to apply them to conduct screening of a disease curing or preventing medicine.

The screening method according to the present invention can use small bony fishes. No particular limitation is imposed on the small bony fishes used in the screening method according to the present invention. However, examples thereof include Zebrafish, globefish, goldfish, killifish and giant rerio. The small bony fishes are favorably used because they are excellent in speed and cost compared with mouse and rat. In particular, Zebrafish is favorable because decoding of genome has been almost completed, its breeding and propagation are easy, circulation cost is also cheap, and the basic structures of main organs and tissues are formed in 48 to 72 hours after fertilization.

The labeling composition for the intraocular tissue according to the present invention can be used in measures for specifically and selectively labeling, for example, a diseased cellular tissue at ophthalmic surgery or a site of a test substance suspected to be a tumor, thereby ascertaining a difference from normal cells, or in observation of a change of a tissue by a disease.

The labeling composition for the intraocular tissue according to the present invention can specifically label an intraocular tissue of a living individual without need of an invasive operation such as exposure of an ocular tissue or injection of a staining agent into the ocular tissue or a nerve tissue linking to the ocular tissue. Accordingly, the composition can be applied to a diagnostic agent making good use of these identification abilities.

No particular limitation is imposed on the diagnostic agent, and the composition can be used as, for example, a diagnostic agent for inspecting the functions of the eyes and a diagnostic agent of ophthalmic diseases.

<Extrapolability to Human>

The labeling composition for the intraocular tissue according to the present invention may also be applied to human. The extrapolability to human is confirmed by overall approximation in recognition of analogy and points of difference of intraocular tissues between human and a laboratory animal. Examples are given below though not limited thereto.

1. Intraocular tissues of human and another living sample than human are labeled to confirm analogy therebetween. Examples of other living samples than human include mammals such as mouse, hamster, rat, guinea pig, rabbit, dog, pig, cat and monkey; and bony fishes such as Zebrafish.

2. An immobilized tissue section of said another living sample than human is used to confirm staining characteristics of intraocular tissues.

3. An immobilized tissue section of human is used to confirm staining characteristics of intraocular tissues.

By confirming the above 3 points, it can be confirmed that the labeling composition for the intraocular tissue according to the present invention may also be applied to human.

As another method for confirming the extrapolability to human, it can be confirmed by radiolabeling the labeling composition for the intraocular tissue according to the present invention, administering a trace quantity of the labeled composition into a body of human and confirming localization of the compound in an intraocular tissue. This method is called a microdosing test.

As another method, there is a method of identifying and confirming the following 4 points.

1. A target biomolecule or labeling mechanism of the labeling composition for the intraocular tissue according to the present invention is identified in an intraocular tissue of another living sample than human.

2. A human biomolecule or labeling mechanism homologous to said target biomolecule or labeling mechanism is identified.

3. Said human biomolecule or staining mechanism is introduced into another laboratory animal than human by a genetic modification.

4. The thus-obtained laboratory animal is used to confirm the fact that staining is made through the biomolecule or staining mechanism introduced.

As another living sample than human, Zebrafish may be particularly favorably used. Eyes are very well preserved anatomically, histologically and biochemically among many vertebrate animals, and the same applies to the genesis. The retina of Zebrafish is made up of 7 main cell types like many presently existing vertebrate animals (Progress in Retinal and Eye Research, 27, pp. 89-110 (2008)), and comparison of retinal tissue section images between human and Zebrafish shows very high commonality though different in scale (Current Opinion in Pharmacology, 4, 504-512 (2004)). The use of Zebrafish has high advantage of low breeding cost and small amount of the compound used compared with mouse. In addition, commonality of not only the morphology, but also the base sequence of rhodopsin that is a visual pigment is somewhat higher than mouse, thus indicating high homology to human at molecular levels. Rodent is nocturnal, while Zebrafish is diurnal and has various cone cells in addition to rod cells at the retina, so that human and Zebrafish have high homology both histologically and functionally. From the above, it is favorable that Zebrafish is used to confirm the extrapolability of the labeling composition for the intraocular tissue according to the present invention to human.

EXAMPLES

The present invention will hereinafter be described in more detail by the following Examples. These Examples are specific examples shown for understanding more deeply the present invention, and the present invention is by no means limited to these specific examples. Incidentally, "%" is based on mass unless expressly noted.

Staining of Intraocular Tissue by Labeling Composition for Intraocular Tissue

Example 1

Distilled water was added to a 1 mg/mL DMSO solution of Staining compound 1 to obtain Staining Liquid 1 containing Staining compound 1 at a concentration of 1 µg/mL. In an arbitrary well of a 24-well multiplate (product of IWAKI), were put 1 mL of Staining Liquid 1 and a fry of Zebrafish 7-day-old embryo (7 dpf), and the plate was left to stand for 1 hour. A process of removing Staining Liquid 1 in the well and replacing it by 1 mL of distilled water was then performed 3 times. Further, 1 mL of a phosphate buffer solution containing 4% paraformaldehyde was added, and the plate was left to stand for 1 hour. The fry was then taken out of the well and embedded in a 5% low-temperature fused agarose gel to prepare a section of an ocular tissue using Linear Slicer PRO 7 (manufactured by Dosaka EM Co., Ltd.). The thus-prepared ocular tissue section was placed on a slide glass to observe the ocular tissue through a confocal microscope (Pascal Exciter, manufactured by Zeiss Co.).

Examples 2 to 106

Sections were prepared by the same process as in Example 1 except that Staining compound 1 in Example 1 was changed to staining compound s described in Table 1, and observed.

Comparative Examples 1 to 3

Sections were prepared by the same process as in Example 1 except that Staining compound 1 in Example 1 was not used or changed to indocyanine green (ICG) or fluorescein (FLU) as described in Table 1, and observed.

Evaluation of Intraocular Tissue-Staining Ability

Regarding Examples 1 to 106, and Comparative Examples 1 to 3, staining ability (+++: intraocular tissue including photoreceptor cell layer being strongly stained; ++: photoreceptor cell layer being stained; −: not stained), and stained sites (1: layer structure including photoreceptor cell layer in retinal tissue being visualized by 1 to 5 layers thereof; 2: retinal tissue being wholly visualized; 3: L: vitreous body being stained) were evaluated.

The results thereof are shown in Table 1. Incidentally, the excitation wavelengths and fluorescence wavelengths of the staining compound s in Examples 1 to 106 were determined by subjecting an aqueous solution obtained by diluting a 10 mg/mL DMSO solution to 1/500 with purified water to measurement using a fluorescence spectrometer FL4500 (manufactured by Hitachi High-Technologies Corporation). Regarding the staining compound s in Examples 95 to 106, values in a chloroform solution are shown.

TABLE 1

| Ex. No. | Compound No. | $\lambda_{ex}$ | $\lambda_{em}$ | Staining ability | Stained site |
|---|---|---|---|---|---|
| 1 | 1 | 599 | 619 | ++ | 2 |
| 2 | 2 | 486 | 553 | +++ | 2 |
| 3 | 3 | 480 | 556 | ++ | 2 |
| 4 | 4 | 473 | 560 | ++ | 1 |
| 5 | 5 | 556 | 577 | +++ | 2, L |
| 6 | 6 | 555 | 576 | ++ | 2, L |
| 7 | 7 | 469 | 555 | ++ | 2, L |
| 8 | 8 | 477 | 592 | ++ | 2 |
| 9 | 9 | 464 | 514 | ++ | 1 |
| 10 | 10 | 459 | 520 | ++ | 1 |
| 11 | 11 | 422 | 476 | +++ | 2, L |
| 12 | 12 | 463 | 509 | ++ | 2, L |
| 13 | 13 | 472 | 504 | +++ | 2 |
| 14 | 14 | 588 | 617 | ++ | 2, L |
| 15 | 15 | 496 | 569 | +++ | 2, L |
| 16 | 17 | 459 | 564 | ++ | 1 |
| 17 | 19 | 545 | 576 | ++ | 1 |
| 18 | 20 | 555 | 567 | ++ | 1 |
| 19 | 21 | 334 | 377 | ++ | 2, L |
| 20 | 22 | 571 | 620 | ++ | 1 |
| 21 | 24 | 609 | 692 | ++ | 1 |
| 22 | 25 | 635 | 671 | ++ | 1 |
| 23 | 26 | 679 | 715 | ++ | 2 |
| 24 | 27 | 485 | 575 | ++ | 1 |
| 25 | 29 | 474 | 509 | ++ | 1, L |
| 26 | 30 | 353 | 481 | ++ | 1 |
| 27 | 31 | 495 | 664 | ++ | 2 |
| 28 | 32 | 558 | 640 | ++ | 2, L |
| 29 | 33 | 512 | 628 | ++ | 1, L |
| 30 | 34 | 571 | 648 | ++ | 2, L |
| 31 | 35 | 535 | 655 | ++ | 2 |
| 32 | 36 | 566 | 661 | +++ | 1 |
| 33 | 37 | 531 | 633 | +++ | 1 |
| 34 | 38 | 482 | 609 | ++ | 1 |
| 35 | 39 | 576 | 657 | ++ | 1 |

TABLE 1-continued

| | Compound No. | λex | λem | Staining ability | Stained site |
|---|---|---|---|---|---|
| 36 | 40 | 559 | 671 | ++ | 1 |
| 37 | 41 | 582 | 679 | ++ | 1 |
| 38 | 44 | 564 | 651 | ++ | 1 |
| 39 | 45 | 481 | 586 | ++ | 1 |
| 40 | 47 | 522 | 611 | ++ | 1 |
| 41 | 48 | 541 | 619 | ++ | 2 |
| 42 | 49 | 569 | 649 | ++ | 1 |
| 43 | 50 | 482 | 580 | ++ | 1 |
| 44 | 51 | 580 | 638 | ++ | 2 |
| 45 | 52 | 580 | 638 | ++ | 1 |
| 46 | 53 | 568 | 712 | ++ | 1 |
| 47 | 54 | 597 | 647 | ++ | 2 |
| 48 | 55 | 502 | 644 | ++ | 1 |
| 49 | 56 | 486 | 606 | ++ | 2 |
| 50 | 57 | 590 | 671 | ++ | 2 |
| 51 | 58 | 546 | 676 | ++ | 2 |
| 52 | 59 | 581 | 625 | ++ | 1 |
| 53 | 60 | 560 | 677 | ++ | 2 |
| 54 | 61 | 545 | 636 | ++ | 2, L |
| 55 | 62 | 610 | 675 | ++ | 2 |
| 56 | 63 | 566 | 611 | ++ | 1 |
| 57 | 64 | 401 | 516 | ++ | 2 |
| 58 | 65 | 570 | 657 | ++ | 1 |
| 59 | 66 | 527 | 636 | +++ | 2 |
| 60 | 67 | 570 | 699 | +++ | 2 |
| 61 | 68 | 450 | 527 | ++ | 2 |
| 62 | 69 | 653 | 609 | ++ | 1 |
| 63 | 70 | 556 | 659 | ++ | 1 |
| 64 | 71 | 592 | 671 | ++ | 2, L |
| 65 | 72 | 611 | 720 | ++ | 1 |
| 66 | 73 | 548 | 649 | ++ | 1 |
| 67 | 74 | 614 | 669 | ++ | 1 |
| 68 | 75 | 619 | 683 | ++ | 1 |
| 69 | 76 | 674 | 724 | ++ | 1 |
| 70 | 77 | 583 | 668 | ++ | 1 |
| 71 | 78 | 598 | 726 | ++ | 1 |
| 72 | 79 | 567 | 702 | ++ | 1 |
| 73 | 80 | 551 | 673 | ++ | 1 |
| 74 | 81 | 576 | 604 | ++ | 2, L |
| 75 | 82 | 591 | 721 | +++ | 2 |
| 76 | 83 | 605 | 682 | ++ | 2 |
| 77 | 84 | 599 | 718 | ++ | 2 |
| 78 | 85 | 353 | 503 | ++ | 2 |
| 79 | 86 | 623 | 671 | ++ | 1 |
| 80 | 87 | 466 | 551 | ++ | 2, L |
| 81 | 88 | 450 | 503 | ++ | 1 |
| 82 | 90 | 528 | 550 | ++ | 2, L |
| 83 | 95 | 509 | 578 | ++ | 2, L |
| 84 | 95 | 528 | 590 | ++ | 1 |
| 85 | 97 | 530 | 680 | ○ | 1 |
| 86 | 98 | 510 | 690 | ○ | 1 |
| 87 | 100 | 430 | 600 | ○ | 1 |
| 88 | 101 | 560 | 760 | ○ | 1 |
| 89 | 102 | 590 | 700 | ○ | 1 |
| 90 | 103 | 520 | 640 | ○ | 1 |
| 91 | 106 | 510 | 650 | ○ | 1 |
| 92 | 107 | 380 | 490 | ○ | 1 |
| 93 | 108 | 530 | 680 | ○ | 1 |
| 94 | 109 | 540 | 630 | ○ | 1 |
| 95 | 110 | 538 | 614 | ○ | 1 |
| 96 | 111 | 527 | 589 | ○ | 1 |
| 97 | 112 | 513 | 568 | ○ | 1 |
| 98 | 113 | 514 | 575 | ○ | 1 |
| 99 | 114 | 513 | 568 | ○ | 1 |
| 100 | 115 | 540 | 614 | ○ | 1 |
| 101 | 116 | 537 | 584 | ○ | 1 |
| 102 | 117 | 538 | 581 | ○ | 1 |
| 103 | 118 | 540 | 634 | ○ | 1 |
| 104 | 120 | 537 | 609 | ○ | 1 |
| 105 | 121 | 537 | 609 | ○ | 1 |
| 106 | 122 | 534 | 582 | ○ | 1 |

TABLE 1-continued

| | Compound No. | λex | λem | Staining ability | Stained site |
|---|---|---|---|---|---|
| Comp. Ex. No. | | | | | |
| 1 | Not used | | | – | — |
| 2 | ICG | 784 | 811 | – | — |
| 3 | Fluorescein | 494 | 521 | – | — |

As apparent from Table 1, the labeling compositions for the intraocular tissue according to the present invention are excellent in fluorescence sensitivity and able to stain living intraocular tissues, so that the staining ability thereof is excellent. The stained sites varied according to the staining compound s used. Some of the compositions strongly stained the photoreceptor cell layer, while some of them exhibited staining ability to the whole retinal tissue. In addition, screening can be cheaply performed by using Zebrafish as a model animal.

In Vivo Intraocular Observation

Example 107

Distilled water was added to a 1 mg/mL DMSO solution of Staining compound 5 so as to give a concentration of 1 μg/mL to obtain Staining Liquid 2. In an arbitrary well of a 24-well multiplate, were put 1 mL of Staining Liquid 2 and a fry of Zebrafish, and the plate was left to stand for 1 hour. A process of removing Staining Liquid 2 in the well and replacing it by 1 mL of distilled water was then performed 3 times.

The fry was then put in a 0.7% agarose solution and placed on a slide glass to observe the fundus of the fry through a confocal microscope.

Examples 108 to 119

Fundus of fry were observed according to the same process as in Example 107 except that the compound used in Example 107 was changed to compounds shown in Table 2.

Comparative Examples 4 to 6

Fundus of fry were observed according to the same process as in Example 107 except that the compound used in Example 107 was changed to compounds shown in Table 2.

Evaluation of In Vivo Intraocular Observation

Regarding Examples 107 to 119 and Comparative Examples 4 to 6, staining ability (+++: both photoreceptor cell layer and further inner layer structure of retina comprised of plural layers being stained; ++: only photoreceptor cell layer of retina comprised of plural layers being mainly stained; –: not observed) was evaluated.

The results thereof are shown in Table 2.

TABLE 2

| | Compound No. | Result of observation |
|---|---|---|
| Ex. No. | | |
| 107 | 5 | +++ |
| 108 | 6 | ++ |

TABLE 2-continued

| | Compound No. | Result of observation |
|---|---|---|
| 109 | 7 | +++ |
| 110 | 8 | +++ |
| 111 | 9 | ++ |
| 112 | 10 | ++ |
| 113 | 11 | +++ |
| 114 | 12 | ++ |
| 115 | 13 | +++ |
| 116 | 36 | ++ |
| 117 | 48 | ++ |
| 118 | 66 | ++ |
| 119 | 81 | +++ |
| Comp. Ex. No. | | |
| 4 | Not used | − |
| 5 | ICG | − |
| 6 | Fluorescein | − |

Figure 4:
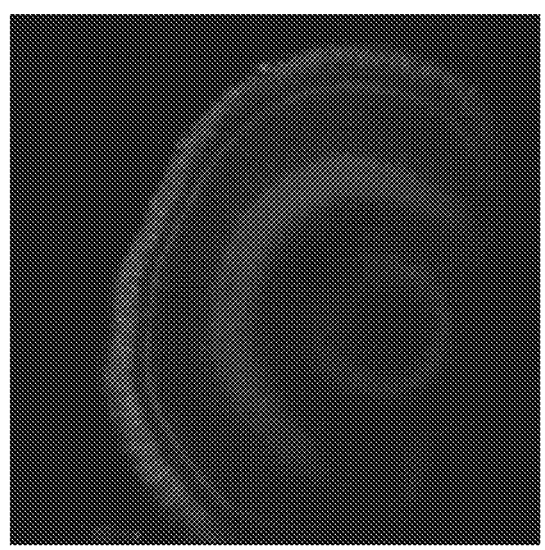
FIG. 4 illustrates an observation image of a retinal tissue in a living body observed in Example 118.

In Examples 107 to 119, fluorescence was observed at the fundus of Zebrafish. Specifically, as illustrated in, for example, FIG. 4, it is understood that the labeling compositions for the intraocular tissue according to the present invention noninvasively migrate to the intraocular tissue to clearly image the intraocular tissue.

Example 120

After an eyeball of a fry of Zebrafish 7-day-old embryo (7 dpf) was immobilized with a PBS solution of 4% paraformaldehyde (PFA), the solution was replaced by a PBS solution of 30% sucrose, and the eyeball was embedded in an OCT compound (product of Tissue-Tek Co.) and frozen with liquid nitrogen. The frozen sample was sliced into a 7-1 μm section by Cryostat (Tissue•Tek Cryo 3, manufactured by Sakura Finetek Japan Co., Ltd.) and extended on a MAS-coated slide glass (product of MATSUNAMI GLASS IND., LTD) to obtain a tissue section slide of the Zebrafish eyeball. The slide glass was treated with a blocking solution (Blocking One, product of Nakarai Co.) for 30 minutes at room temperature, and an anti-Zpr-1 antibody (which stains red and green cone cells) diluted with PBS was mounted as a primary antibody on the slide glass and treated for 12 hours at 4° C. The slide glass was then washed 3 times with PBST for 10 minutes, and a secondary antibody (Alexa 488-anti-mouse IgG antibody) and 1 μg/mL of Compound 5 were diluted with PBS and mounted on the slide glass for 1 hour at room temperature. The slide glass was washed 3 times with PBST for 10 minutes, Fluoromount G (product of Southem Biotechnology Co.) was mounted thereon, and a cover glass was placed thereon. The thus-obtained stained slide of the tissue section of the Zebrafish eye ball was observed through a confocal microscope.

Example 121

A stained slide of a tissue section of a Zebrafish eye ball was prepared according to the same process as in Example 120 except that the primary antibody used in Example 120 was changed to an anti-Zpr-3 antibody (which stains rod cells), and observed through a confocal microscope.

Example 122

A stained slide of a tissue section of a human normal retina was prepared according to the same process as in Example 120 except that the tissue section slide of the Zebrafish eyeball was changed to a tissue section slide (product of US Biomax Co.) of the human normal retina, and the primary antibody and secondary antibody were changed to anti-mGluR5 antibody (which stains cone cells) and Alexa 488-anti-rabbit IgG antibody, respectively, and observed through a confocal microscope.

Evaluation of Stained Slide

Figure 5:
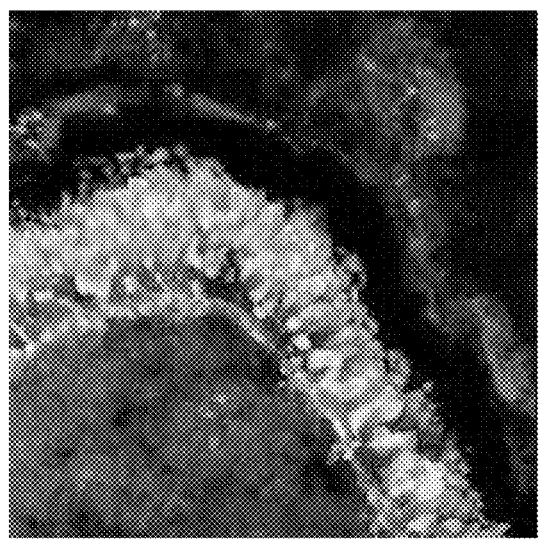
FIG. 5 illustrates a labeled image of a frozen section of a Zebrafish eyeball observed in Example 120.
Figure 6:
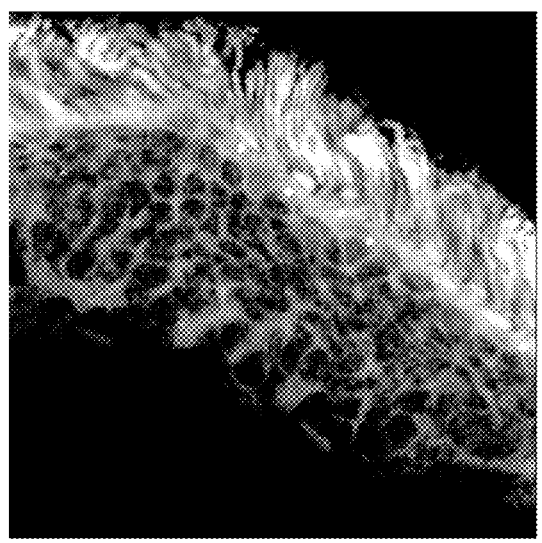
FIG. 6 illustrates a labeled image of a frozen section of a man eyeball observed in Example 122.
Figure 7:
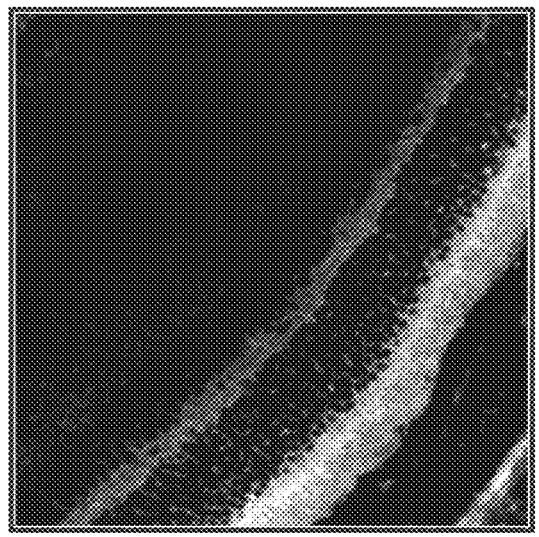
FIG. 7 illustrates a labeled image of a frozen section of a mouse eyeball observed in Example 123.

In Example 120, the stained images with Compound 5 and anti-Zpr-1 antibody in the photoreceptor cell layer did not overlap (FIG. 5), but in Example 121, the stained images with Compound 5 and anti-Zpr-3 antibody in the photoreceptor cell layer partially overlapped. This fact indicates that Compound 5 has staining ability to the photoreceptor cell layer but does not stain the red and green cone cells in the photoreceptor cell layer, or non-stained portions exist in cell bodies existing in the photoreceptor cell layer. On the other hand, the result of Example 121 reveals that Compound 5 has stained the rod cells and at least one kind of cell type of blue or ultraviolet cone cells. From this fact, it was confirmed that Compound 5 selectively stains a part of the cell types in the photoreceptor cell layer or of the cell bodies existing in the photoreceptor cell layer.

In Example 122, it was confirmed that the photoreceptor cell layer common to the retina of Zebrafish in the frozen section of the human normal retina is stained. It was also confirmed that the stained site by the anti-mGluR5 antibody is different, and so a part of the cell types in the photoreceptor cell layer or of the cell bodies existing in the photoreceptor cell layer is selectively stained even in human. From the above results, it was confirmed that the retinas of human and Zebrafish are approximate in staining characteristics, and the labeling composition for the intraocular tissue according to the present invention is high in extrapolability to human.

Staining of Mouse Intraocular Tissue

Example 123

Staining compound 81 was added to an equimolar amount of a NaOH solution so as to give a concentration of 10 mg/mL, and the resultant mixture was centrifuged for 5 minutes at 14 krpm to obtain a supernatant. To an abdominal cavity of a 3-month-old B10 mouse, was administered 0.2 mL of this supernatant at one time. After 1 hour, the thus-treated animal was sacrificed under anesthesia by diethyl ether, and an eyeball thereof was taken out. The eyeball taken was embedded in an OCT compound and frozen in isopentane chilled with liquid nitrogen. This eyeball was sliced into a thickness of about 5 μm in a cryostat chilled to −20° C., and this slice was placed on a slide glass and dried to prepare a section of an ocular tissue. The thus-prepared ocular tissue section was observed through a confocal microscope (Pascal Exciter, manufactured by Zeiss Co.). As a result, it was confirmed that Compound 81 has staining ability to the retina by administration to the abdominal cavity of the mouse.

Staining of Intraocular Tissue and Hair Cell

It was confirmed that the staining compound s used in Examples 15 to 20, 24, 53 to 58, 65, 67, 82, and 83 stain hair cells in vivo in addition to the effect of staining the intraocular tissues. In other words, it was found that the compound represented by Compound Nos. 15, 17, 19 to 22, 27, 60 to 65, 72, 74, 90, and 94 have an effect of coincidently staining both intraocular tissues and hair cells.

INDUSTRIAL APPLICABILITY

The present invention provide labeling compositions for intraocular tissues, which can stain intraocular tissues of living samples and can image cell morphologies of the intraocular tissues with high sensitivity, so that the compositions become materials essential to researches in the ophthalmic field and ophthalmologic imaging techniques. In addition, evaluation with time becomes feasible in drug discovery relating to ophthalmic diseases, high-throughput and high-precision screening can be conducted at low cost, and development of new diagnosing methods and curing methods for diseases as well as ophthalmologic researches are significantly advanced. Thus, the present invention becomes an extremely effective platform technology from industrial and practical points of view.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2008-330988, filed Dec. 25, 2008, which is hereby incorporated by reference herein in its entirety.

The invention claimed is:
1. An imaging method for an intraocular tissue comprising:
bringing a labeling composition for the intraocular tissue or a staining agent for the intraocular tissue, which comprises the labeling composition for the intraocular tissue, into contact with the ocular tissue;
irradiating the intraocular tissue with excitation light to observe fluorescence; and
acquiring a fluorescent image,
wherein the labeling composition comprises a fluorescent compound capable of labeling at least a photoreceptor cell layer of a retina, and
wherein the fluorescent compound is selected from the group consisting of compounds (1)-(9), (11)-(13), (32), (33), (87), (90)-(95), and (109)-(112):

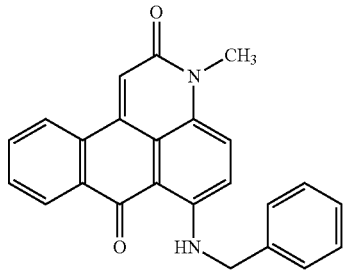
(1)

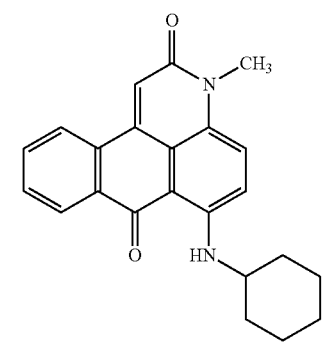
(2)

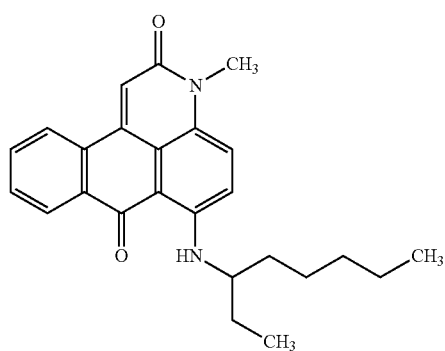

-continued

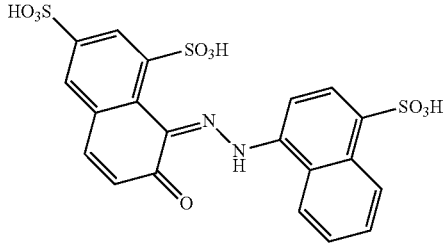
(3)

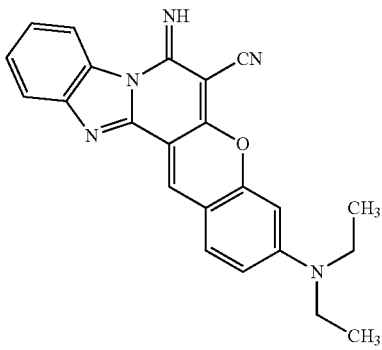
(4)

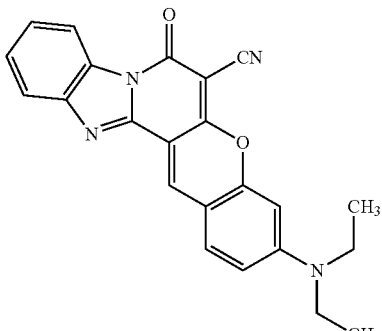
(5)

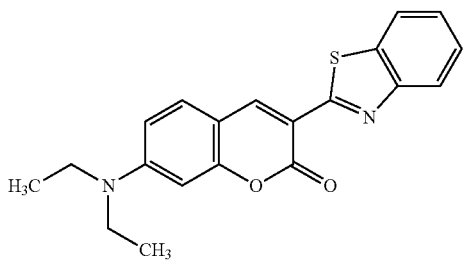
(6)

(7)

-continued
(8)
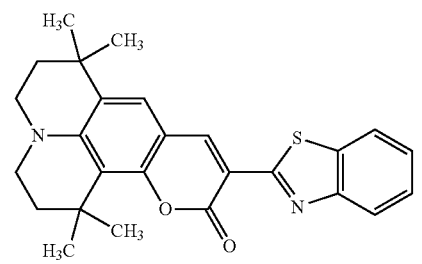
(9)
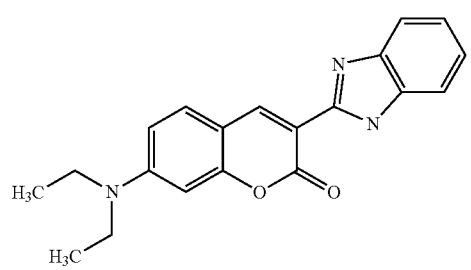
(11)
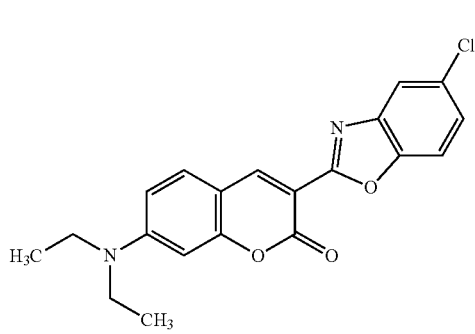
(12)
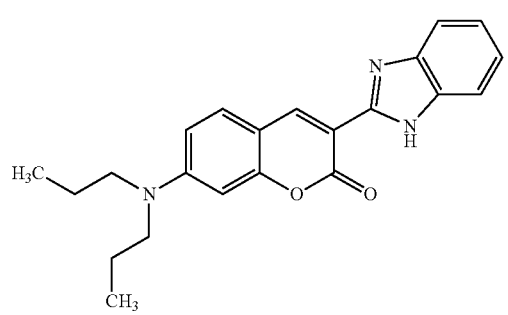
(13)
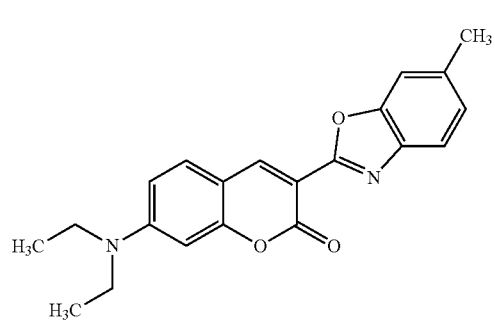
-continued
(32)
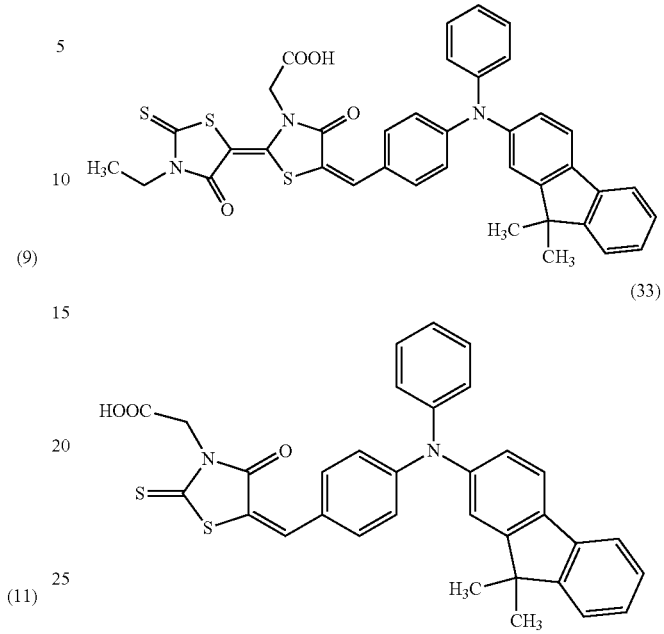
(33)
(87)
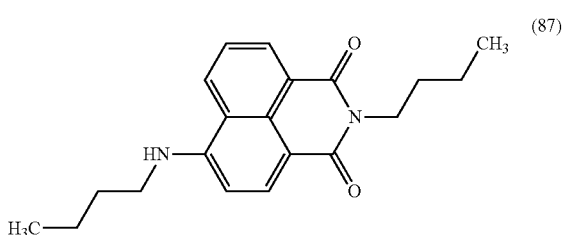
(90)
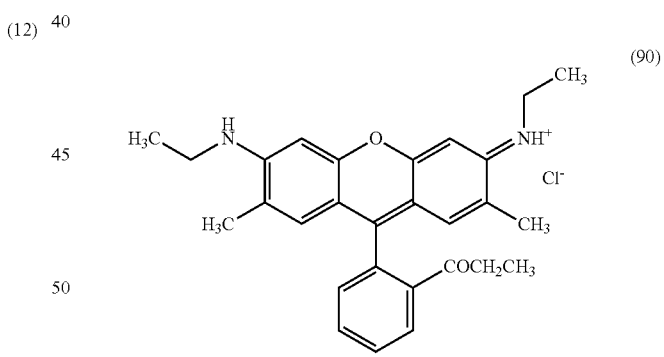
(91)
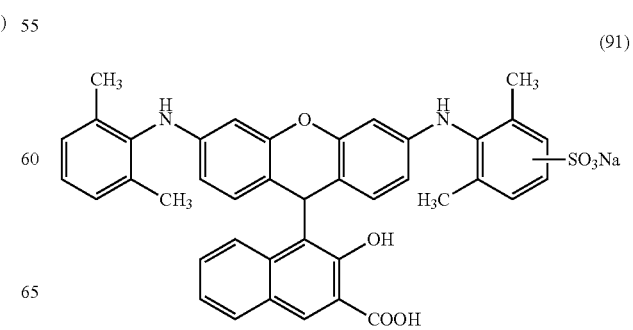

(92) 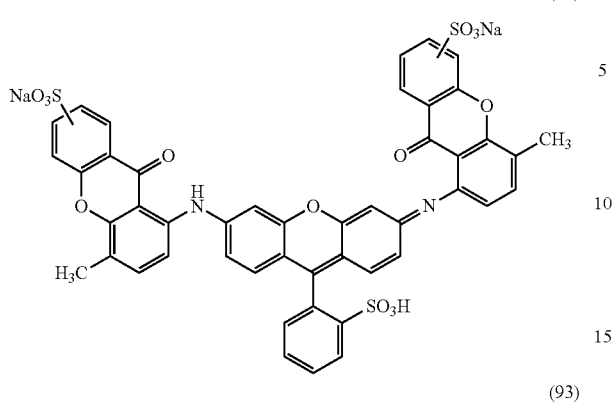
(93) 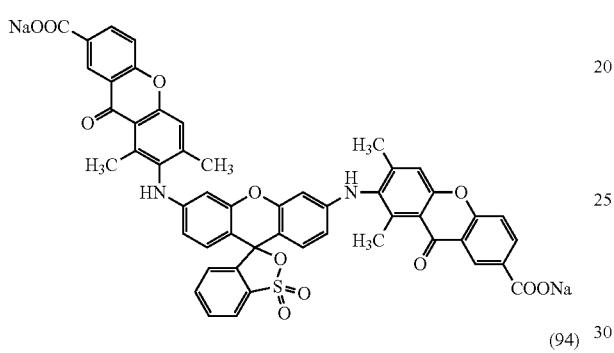
(94) 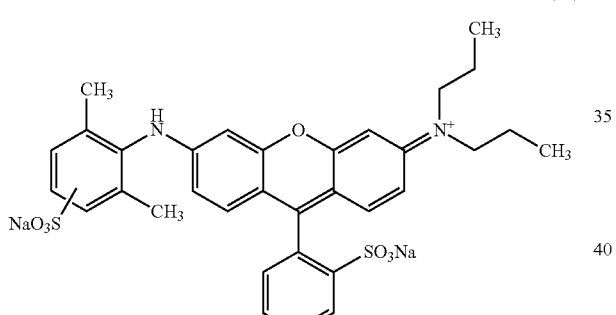
(95) 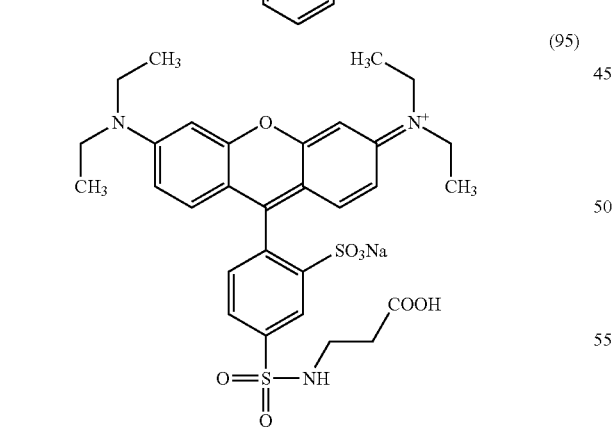
(109) 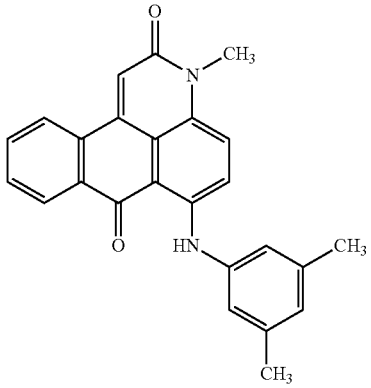
(110) 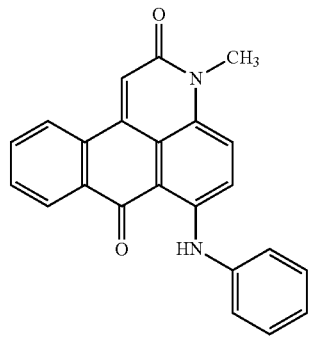
(111) 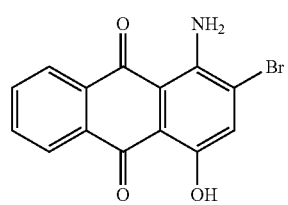
(112) 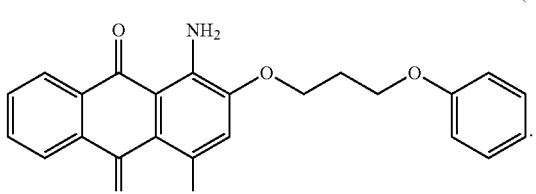
2. An evaluating method for a condition of a retina comprising:
   imaging an intraocular tissue by the imaging method according to claim 1; and
   evaluating the condition of the retina using the obtained fluorescent image.
* * * * *